(12) United States Patent
Wolozin et al.

(10) Patent No.: US 9,359,363 B2
(45) Date of Patent: Jun. 7, 2016

(54) IDENTIFICATION OF COMPOUNDS THAT DISPERSE TDP-43 INCLUSIONS

(75) Inventors: Benjamin Wolozin, Newton, MA (US); Marcie Glicksman, Winchester, MA (US); Gregory D. Cuny, Houston, TX (US); Justin Boyd, Winchester, MA (US)

(73) Assignees: AQUINNAH PHARMACEUTICALS, INC., Newton, MA (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 76 days.

(21) Appl. No.: 14/118,628

(22) PCT Filed: May 21, 2012

(86) PCT No.: PCT/US2012/038861
§ 371 (c)(1),
(2), (4) Date: Nov. 19, 2013

(87) PCT Pub. No.: WO2012/162249
PCT Pub. Date: Nov. 29, 2012

(65) Prior Publication Data
US 2014/0080780 A1 Mar. 20, 2014

Related U.S. Application Data

(60) Provisional application No. 61/488,468, filed on May 20, 2011.

(51) Int. Cl.
| | | |
|---|---|---|
| *C07D 487/04* | (2006.01) | |
| *C07D 207/36* | (2006.01) | |
| *C07D 211/26* | (2006.01) | |
| *C07D 211/52* | (2006.01) | |
| *C07D 215/227* | (2006.01) | |
| *C07D 215/36* | (2006.01) | |
| *C07D 239/52* | (2006.01) | |
| *C07D 239/94* | (2006.01) | |
| *C07D 401/04* | (2006.01) | |
| *C07D 401/12* | (2006.01) | |
| *C07D 403/06* | (2006.01) | |
| *C07D 417/04* | (2006.01) | |
| *A61P 25/28* | (2006.01) | |
| *A61K 31/4025* | (2006.01) | |
| *A61K 31/445* | (2006.01) | |
| *A61K 31/454* | (2006.01) | |
| *A61K 31/4545* | (2006.01) | |
| *A61K 31/47* | (2006.01) | |
| *A61K 31/505* | (2006.01) | |
| *A61K 31/517* | (2006.01) | |
| *A61K 31/519* | (2006.01) | |
| *A61K 31/551* | (2006.01) | |
| *A61K 31/365* | (2006.01) | |
| *A61K 31/704* | (2006.01) | |
| *C07D 211/34* | (2006.01) | |
| *G01N 33/50* | (2006.01) | |

(Continued)

(52) U.S. Cl.
CPC ............ *C07D 487/04* (2013.01); *A61K 31/365* (2013.01); *A61K 31/4025* (2013.01); *A61K 31/445* (2013.01); *A61K 31/454* (2013.01); *A61K 31/4545* (2013.01); *A61K 31/47* (2013.01); *A61K 31/505* (2013.01); *A61K 31/517* (2013.01); *A61K 31/519* (2013.01); *A61K 31/551* (2013.01); *A61K 31/704* (2013.01); *C07D 207/36* (2013.01); *C07D 211/34* (2013.01); *C07D 211/52* (2013.01); *C07D 215/227* (2013.01); *C07D 215/36* (2013.01); *C07D 239/52* (2013.01); *C07D 239/94* (2013.01); *C07D 401/04* (2013.01); *C07D 401/12* (2013.01); *C07D 403/06* (2013.01); *C07D 417/04* (2013.01); *G01N 33/5058* (2013.01)

(58) Field of Classification Search
CPC .. C07D 487/04; C07D 207/36; C07D 211/26; C07D 211/52; C07D 215/227; C07D 215/36; C07D 239/52; C07D 239/94; C07D 401/04; C07D 401/12; C07D 403/06; C07D 417/04
USPC ......... 514/312, 318, 321, 323, 331, 327, 427, 514/468, 218, 221, 267, 266.4, 269
See application file for complete search history.

(56) References Cited

U.S. PATENT DOCUMENTS

| 7,163,942 B2 | 1/2007 | Brodney et al. |
| 7,741,362 B2 | 6/2010 | Temperi et al. |

(Continued)

FOREIGN PATENT DOCUMENTS

| WO | 0215912 A1 | 2/2002 | |
| WO | 2005095334 A1 | 10/2005 | |
| WO | 2010039982 A1 | 4/2010 | |
| WO | WO 2010/111587 | * 9/2010 | ............. C07H 21/00 |

OTHER PUBLICATIONS

Boyd et al. "A High-Content Screen Identifies Novel Compounds That Inhibit Stress-Induced TDP-43 Cellular Aggregation and Associated Cytotoxicity" Journal of Biomolecular Screening (2013) published on line Sep. 9, 2013, pp. 1-13.

(Continued)

*Primary Examiner* — Shengjun Wang
*Assistant Examiner* — Irina Neagu
(74) *Attorney, Agent, or Firm* — Lando & Anastasi, LLP

(57) ABSTRACT

Herein, methods of modulating inclusion formation and stress granules in cells are described. The methods comprise contacting a cell with an inclusion inhibitor. Methods for screening for modulators of TDP-43 aggregation are also described.

15 Claims, 20 Drawing Sheets

(56) References Cited

U.S. PATENT DOCUMENTS

| | | |
|---|---|---|
| 2008/0194557 A1 | 8/2008 | Barbosa et al. |
| 2008/0274121 A1 | 11/2008 | Yao et al. |
| 2011/0034447 A1 | 2/2011 | Nonaka et al. |
| 2011/0097329 A1 | 4/2011 | Chang et al. |
| 2011/0142789 A1 | 6/2011 | Gitler et al. |

OTHER PUBLICATIONS

Duverger et al. "The anticancer drug mithramycin A sensitises tumour cells to apoptosis induced by tumour necrosis factor (TNF)" British Journal of Cancer (2014) vol. 90, pp. 2025-2031.

European Search Report for European Application No. EP12789991.2 dated Mar. 6, 2015.

Homma et al. "Expression of FSHD-related DUX4-FL alters proteostasis and induces TDP-43 agrregation" Annals of Clinical and Translational Neurology (2015) vol. 2, No. 2, pp. 151-166.

International Search Report for International Application No. PCT/US12/38861 dated Aug. 24, 2012.

Lin et al. "Mithramycin A inhibits DNA methyltransferase and metastasis potential of lung cancer cells" Anti-Cancer Drugs (2007) vol. 18, No. 10, pp. 1157-1164.

Seznec et al. "Therapeutic effects of the Sp1 inhibitor mithramycin A in glioblastoma" Journal of Neurooncology (2011) vol. 11, pp. 365-377.

Yuan et al. "Therapeutic Inhibition of Sp1 Expression in Growing Tumors by Mithramycin A Correlates Directly With Potent Antiangiogenic Effects on Human Pancreatic Cancer" Cancer (2007) vol. 110, No. 12, pp. 2682-2690.

Zhao et al. "Novel indole-3-sulfonamides as potent HIV non-nucleoside reverse transcriptase inhibitors (NNRTIs)" Bioorganic & Medicinal Chemistry Letters (2008) vol. 18, No. 2, pp. 554-559.

* cited by examiner

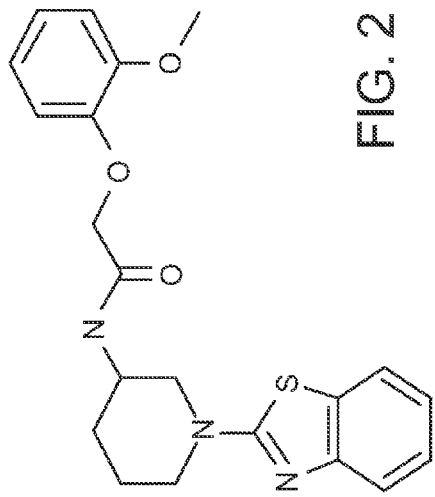
FIG. 2
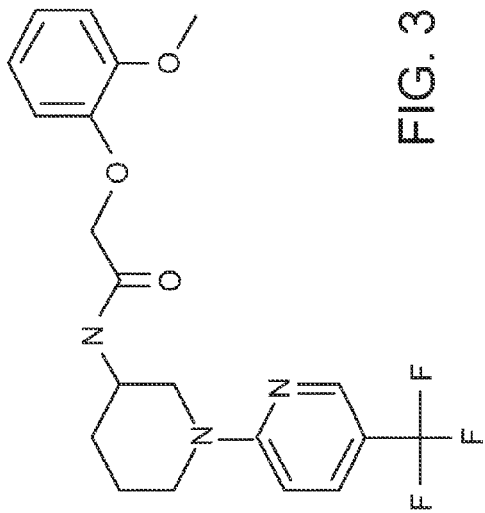
FIG. 3
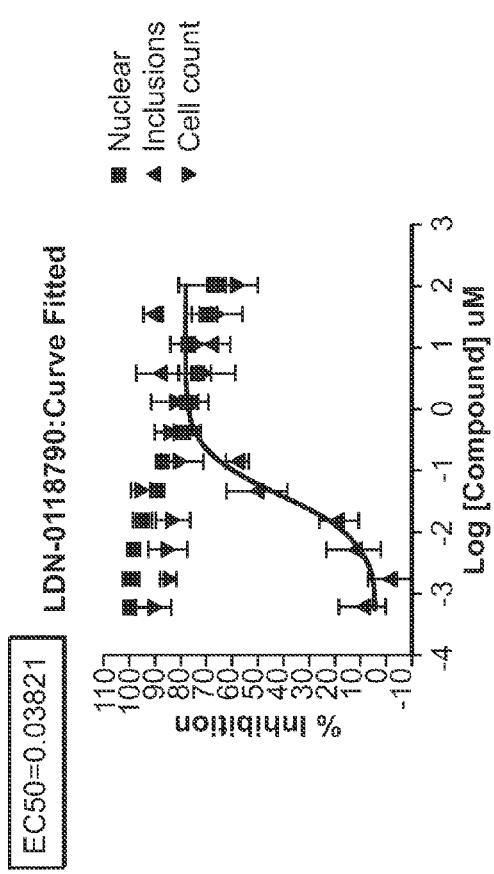
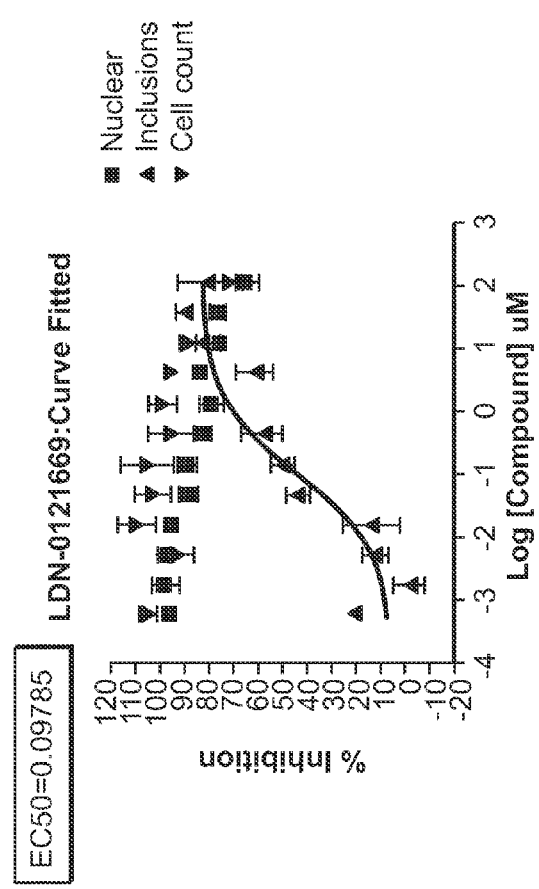

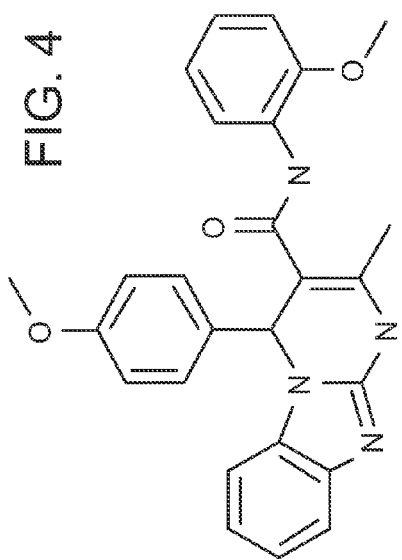
FIG. 4
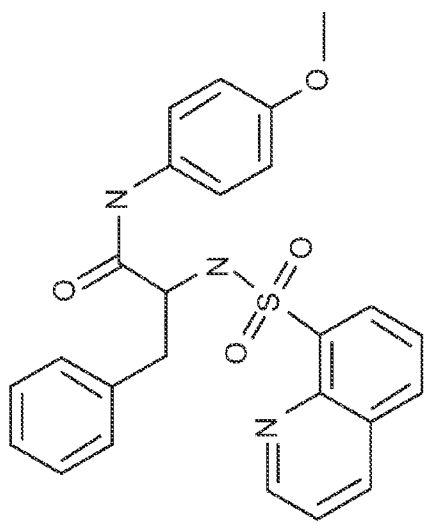
FIG. 5
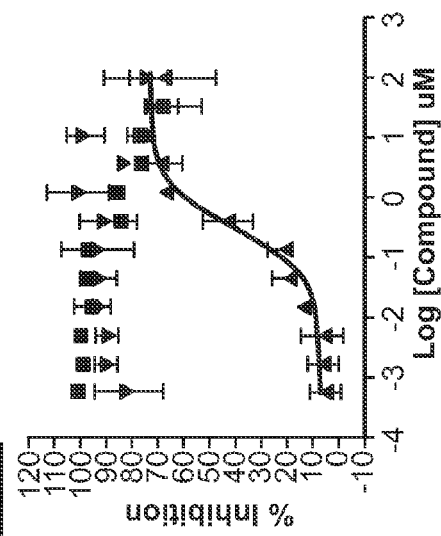
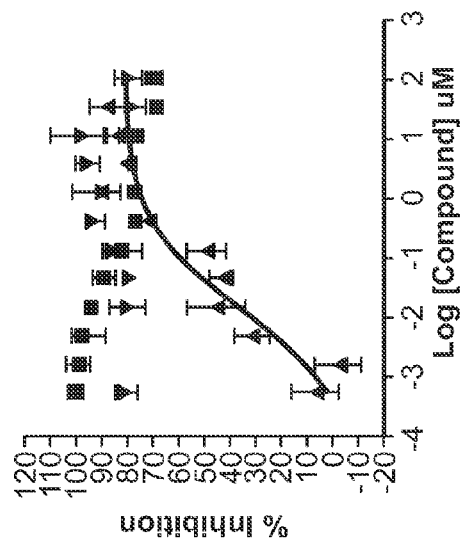

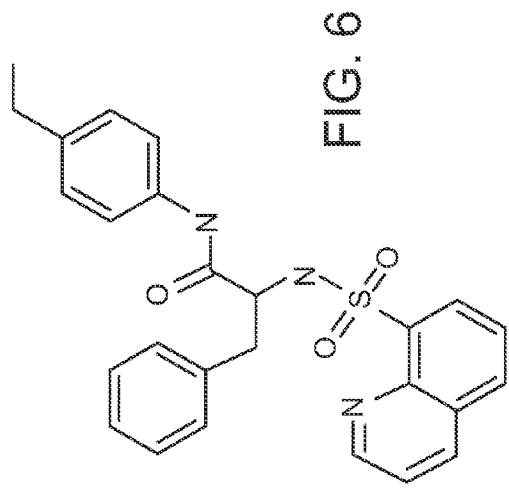
FIG. 6
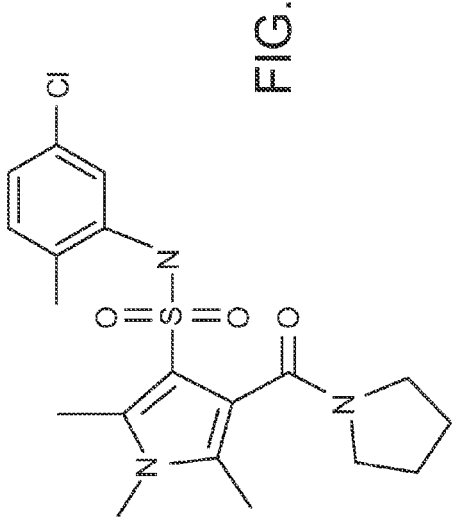
FIG. 7
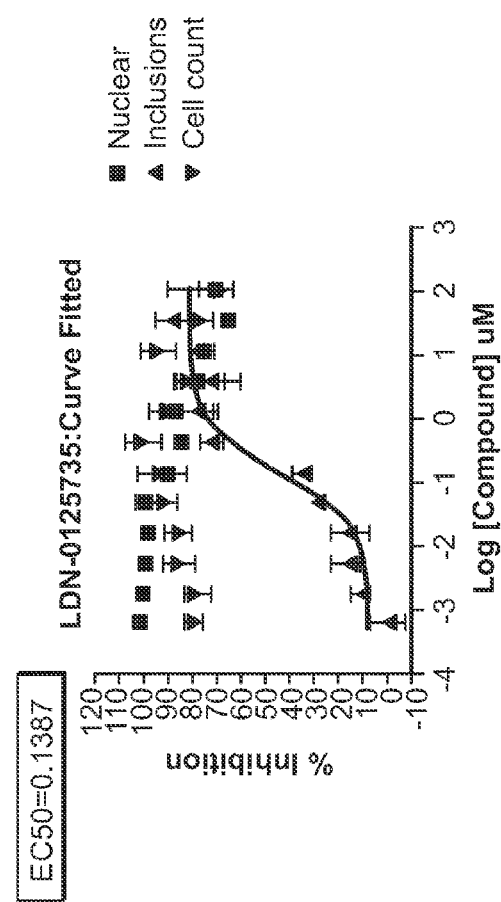
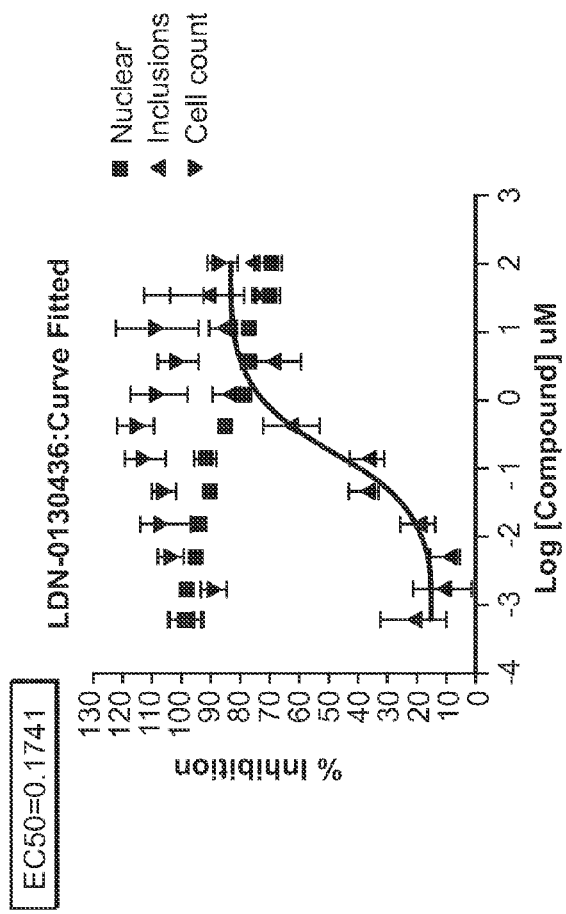

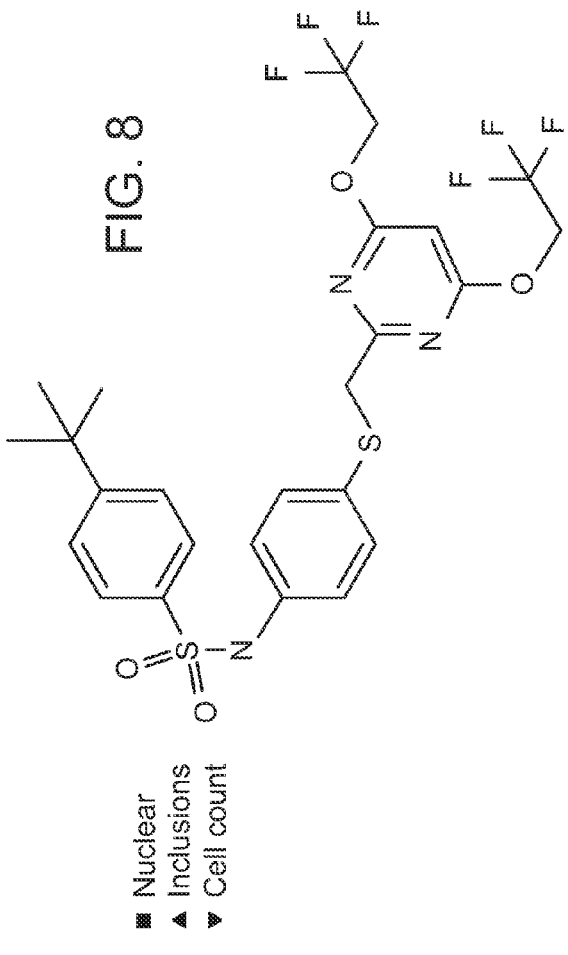
FIG. 8
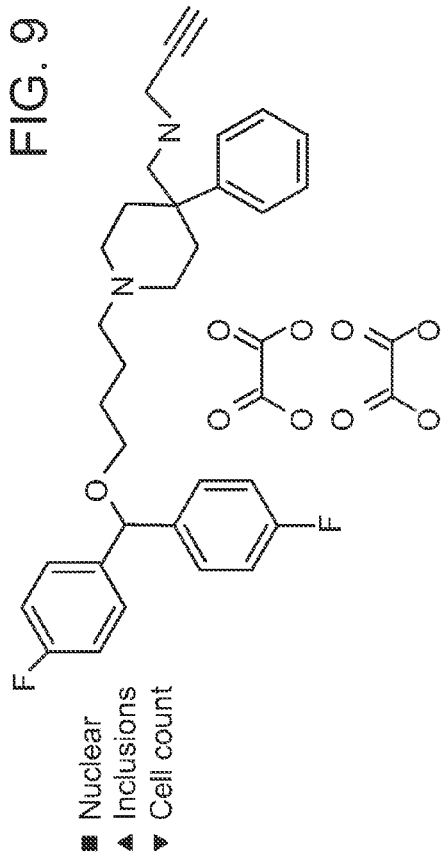
FIG. 9
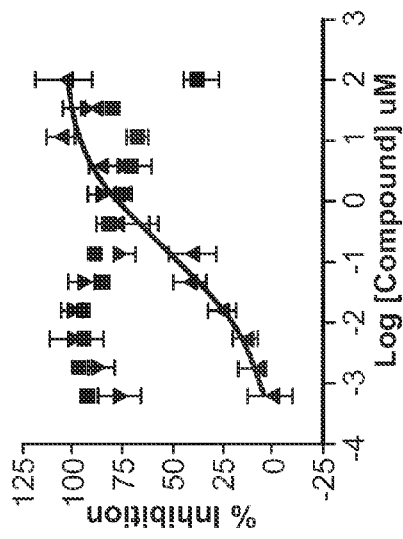
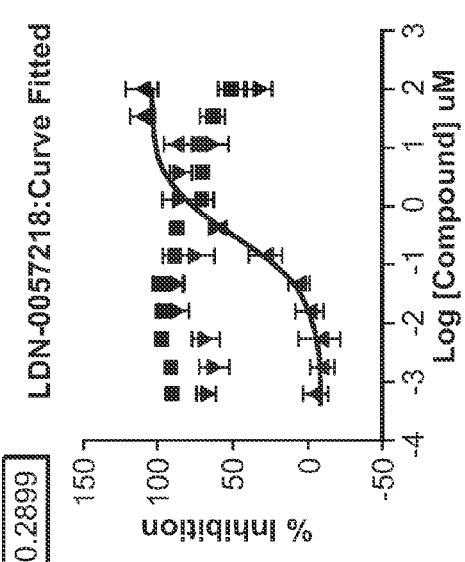

| Compound | R | R₁ |
|---|---|---|
| 8a | 2-Me, 5-Cl | H |
| 8b | 4-OMe | H |
| 8c | 2-Me, 6-Me | H |
| 8d | H | Et |
| 8e | 2-Me, 3-Cl | H |
| 8f | 2-Cl | H |
| 8g | 2-OMe | H |
| 8h | H | H |

Inclusion formation in primary neurons (DIV6) over-expressing TDP-43 and TIA. Map2 reactivity is endogenous.

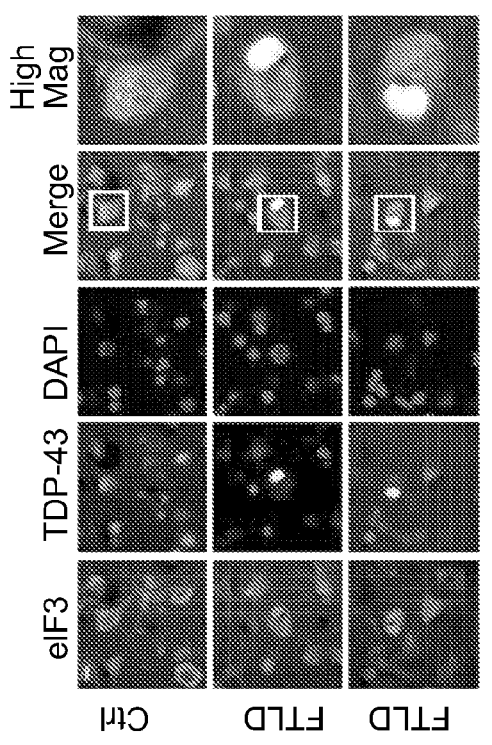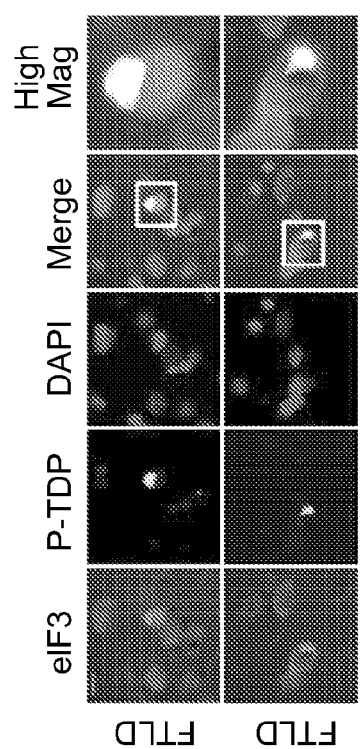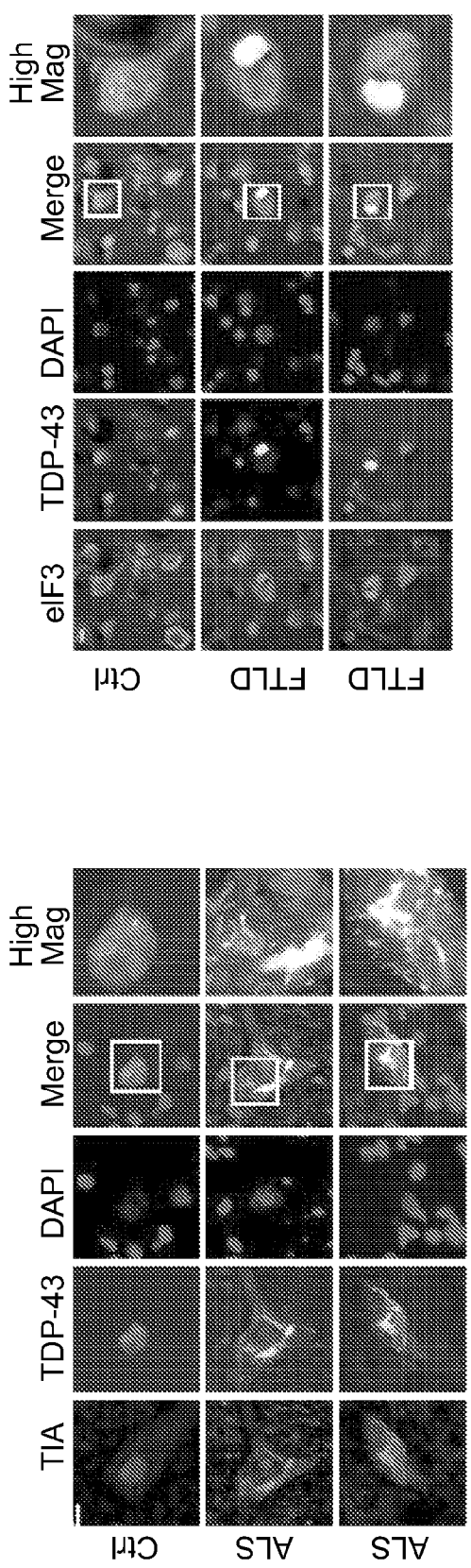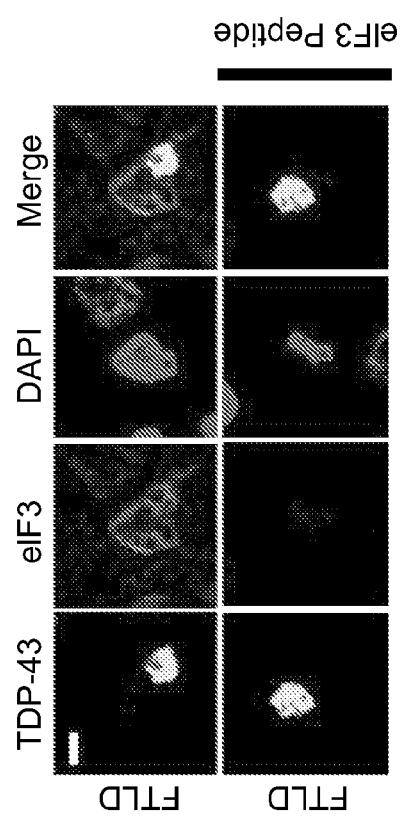
FIG. 16A
FIG. 16B
FIG. 16C
FIG. 16D

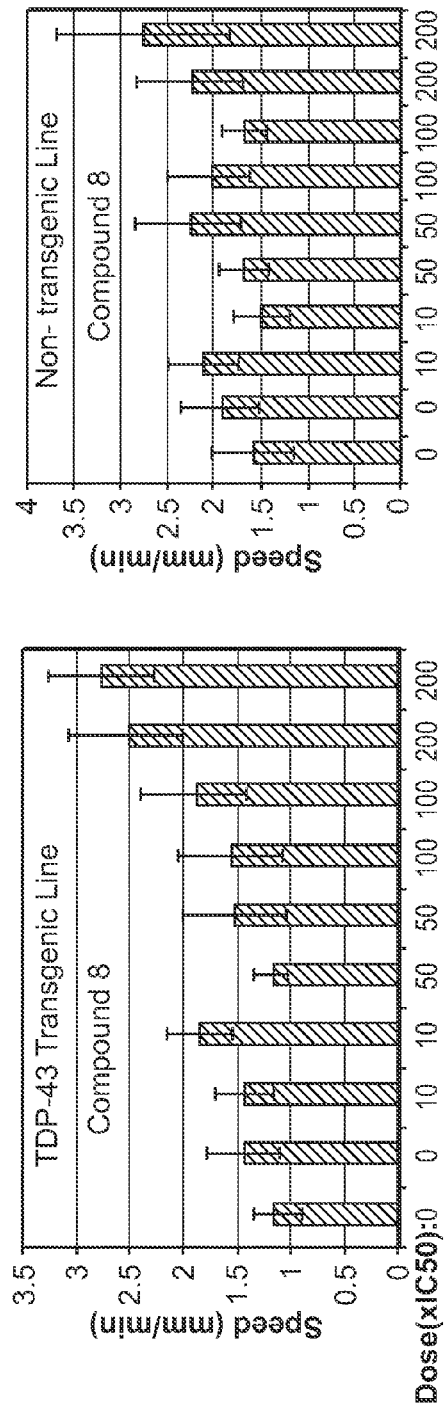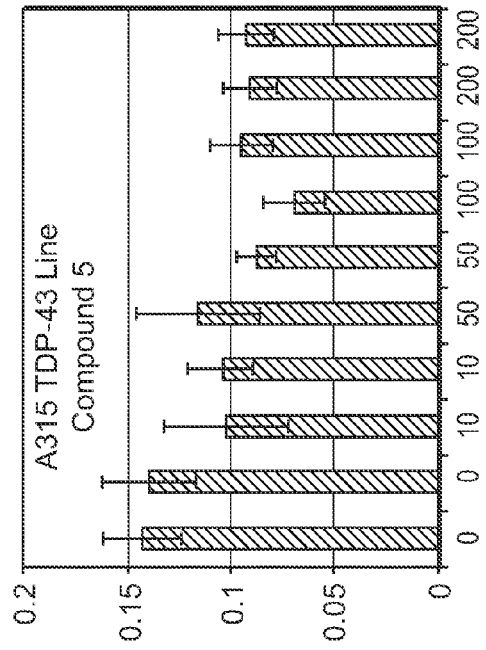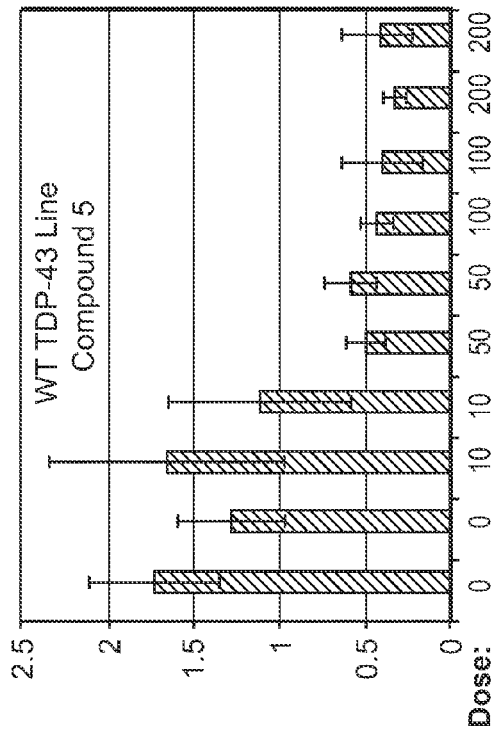
FIG. 19A
FIG. 19B
FIG. 19C
FIG. 19D

IDENTIFICATION OF COMPOUNDS THAT DISPERSE TDP-43 INCLUSIONS

This application is a national stage entry of prior International Application No. PCT/US2012/038861, filed May 21, 2012, which claims priority to U.S. Provisional Application No. 61/488,468, filed on May 20, 2011, the entirety of each of which is incorporated herein by reference.

GOVERNMENT SUPPORT

This invention was made with government support under Contract No. NS066108 awarded by the National Institutes of Health. The government has certain rights in the invention.

FIELD OF THE INVENTION

The invention relates to methods and compositions modulating inclusion formation and stress granules in cells, and for treatment of neurodegenerative diseases, cancer and viral infections.

BACKGROUND OF THE INVENTION

TDP-43 was recently identified as one of the major proteins that accumulate in inclusions in Amyotrophic Lateral Sclerosis (ALS) and in Fronto-temporal lobar dementia with ubiquitin inclusions (FTLD-U). Abnormalities in TDP-43 biology appear to be sufficient to cause neurodegenerative disease because mutations in TDP-43 occur in familial ALS. The prevalence of TDP-43 deposits in diseases such as ALS and FTLD-U, combined with the ability of abnormal TDP-43 to cause disease places TDP-43 in the class of proteins that are major components of neurodegenerative disease. This class includes tau, α-synuclein, huntingtin and β-amyloid. Analysis of the biology of the major proteins that accumulate in other neurodegenerative diseases has lead to major advances in our understanding of the pathophysiology of the disease and also development of new drug discovery platforms. During the course of studying TDP-43, we discovered that this protein is part of the stress granule machinery. This work lead us to important discoveries about how to model the pathophysiology of ALS and FTLD-U in cell culture.

Currently, it is believed that aggregates that accumulate in neurodegenerative diseases like ALS, FTLD-U, Parkinson's disease and Huntington's disease accumulate slowly and are very difficult to disaggregate or perhaps can't be disaggregated. Thus, there is a need in the art for compostions and methods that can rapidly disaggregate stress granules and/or inhibit the formation of stress granules.

SUMMARY OF THE INVENTION

In one aspect, the invention provides methods for treatment of a neurodegenerative disease or disorder, a cancer, and/or a viral infection in a subject, the method comprising administering a stress granule modulator to a subject in need thereof.

In another aspect, the invention provides methods of diagnosing a neurodegenerative disease in a subject, the method comprising administering a stress granule marker to the subject. For use in diagnosing a stress granule marker can be labeled with a label.

In another aspect, the invention provides methods of modulating stress granules comprising contacting a cell with a TDP-43 inclusion inhibiting compound.

In another aspect, the invention provides methods of modulating TDP-43 inclusion formation comprising contacting a cell with a TDP-43 inclusion inhibitor.

In yet another aspect, the invention provides a method of screening for modulators of TDP-43 aggregation comprising contacting a compound with the cell that expresses TDB-43 and develops spontaneous inclusions.

In still another aspect, the invention provides a cell that expresses wild-type TDB-43 and develops spontaneous inclusions.

Still other objects and advantages of the invention will become apparent to those of skill in the art from the disclosure herein, which is simply illustrative and not restrictive. Thus, other embodiments will be recognized by the skilled artisan without departing from the spirit and scope of the invention.

BRIEF DESCRIPTION OF THE FIGURES

FIGS. 2-12 are dose response curves showing inhibition of TDP-43 inclusion formation with little toxicity by some of the compounds described herein. Structures of the compounds are also shown.

FIG. 15 shows induction of TDP-43 inclusions.

FIG. 16 shows co-localization of TDP-43 inclusions (green) with A) TIA-1 in spinal cord of ALS patients and B) eIF3 in frontal cortex of patients with FTLD-U. C) Immunoadsorption with epitope peptide removes reactivity, showing specificity. D) Phospho-TDP-43 also co-localizes with SG markers. Bar=3 m.

FIG. 19 shows motor function effects of LDN-0130436 in C. elegans expressing human WT TDP-43 (A), non-transgenic N2 (B), A315T (C) and A315T (D).

DETAILED DESCRIPTION OF THE INVENTION

Figures 1A, 1B:
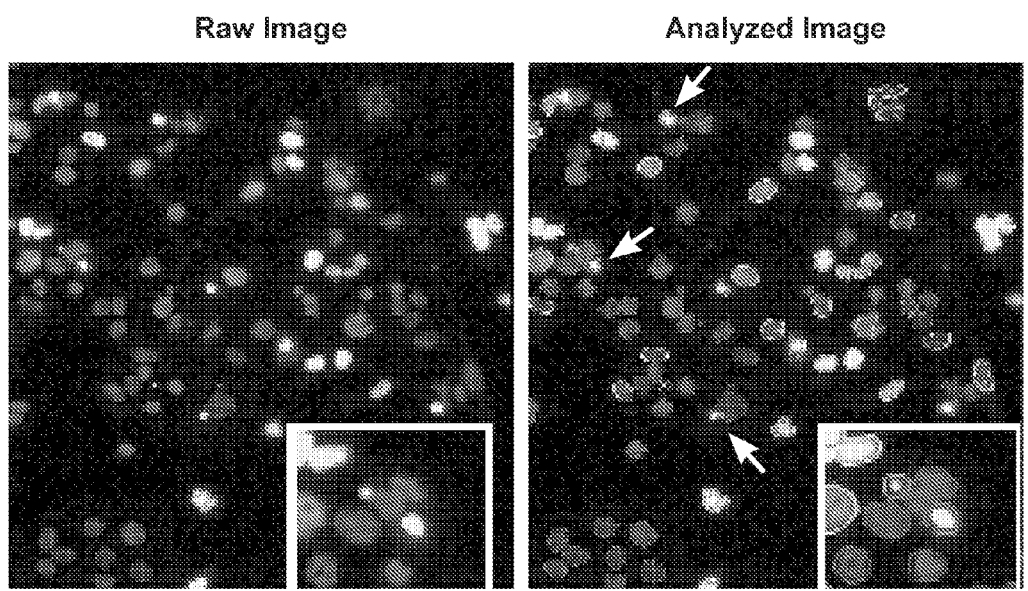
FIG. 1. shows images of TDP-43 inclusions in PC12 cell lines after three days of induction. A) Raw image of TDP-43::GFP (green), nuclei are stained with DAPI (blue). B) Computer-based image processing differentiates between cytoplasmic inclusions (circled in red, inset), and nuclear TDP-43 expression (circled in green, inset).

ALS occurs with an incidence of approximately 1/100,000 (Lancet, 2007. 369: 2031-41; herein incorporated by reference in its entirety). There is currently no therapy for ALS and it is universally fatal. ALS presents with motor weakness in the distal limbs that rapidly progresses proximally (Lancet, 2007. 369: 2031-41; Trends Mol Med, 2004. 10: 275-82; each herein incorporated by reference in its entirety). TDP-43 is the major protein that accumulates in affected motor neurons in sporadic ALS (Science, 2006. 314: 130-3; herein incorporated by reference in its entirety). The causes of sporadic ALS are not known, but identification of the major pathological species accumulating in the spinal cord of ALS patients represents a seminal advance for ALS research. TDP-43 is the only protein in ALS that is both genetically and pathologically linked with sporadic ALS, which is the predominant form of the disease. Multiple papers have identified mutations in TDP-43 associated with sporadic and familial ALS (Science, 2008. 319: 1668-72; Ann Neurol, 2008, 63(4), 535-538; each herein incorporated by reference in its entirety). Inhibitors of cell death and inclusions linked to TDP-43 represents a novel therapeutic approach to ALS, and could also elucidate biochemical pathway linked to TDP-43 biology.

TDP-43 is one of the most promising targets for pharmacotherapy of Amyotrophic Lateral Sclerosis (ALS). TDP-43 is one of the major proteins that accumulate in inclusions in ALS, and mutations in TDP-43 cause familial ALS, which indicates that abnormalities in TDP-43 biology are sufficient to cause disease (Science, 2006. 314: 130-3; herein incorporated by reference in its entirety).

Formation of cytoplasmic TDP-43 inclusions appears to be intimately linked to the RNA metabolism, and specifically the biology of stress granules (SGs). SGs are protein-mRNA aggregates that form in response to stress (Trends Biochem Sci, 2008. 33: 141-50; Biochem Soc Trans, 2002. 30: 963-9; Hum Mol Genet, 2010. 19: R46-64; each herein incorporated by reference in its entirety). Studies from our laboratory, and other laboratories, show that TDP-43 inclusions human brain (as well as in cell culture) co-localize with SGs, and that agents that inhibit SG formation also inhibit formation of TDP-43 inclusions (*PLoS ONE*, October 2010 5(10), e13250; herein incorporated by reference in its entirety). Results presented herein demonstrate that neurodegeneration mediated by TDP-43 is linked to the regulation of protein translation and stress granule biology. The relationship between TDP-43 and stress granule biology is important because it provides a novel approach for dispersing TDP-43 inclusions using physiological pathways that normally regulate this reversible process rather than direct physical disruption of protein aggregation by a small molecule pharmaceutical. Stress granule biology also regulates autophagy and apoptosis, both of which are linked to neurodegeneration. Hence, chemicals inhibiting TDP-43 aggregation can also inhibit neurodegeneration.

The inventors have completed a high throughput screen for small molecules that inhibit TDP-43 aggregation using PC12 cells that inducibly express TDP-43. They identified a number of compounds (on different scaffolds) that inhibit TDP-43 inclusion formation in a reproducible and dose-dependent manner, while showing little to no cytotoxicity. These compounds can be further tested to determine which of these lead compounds can inhibit inclusion formation and neurodegeneration in secondary assays, and then to do chemical optimization to increase the potency and optimize the pharmacological properties of the two most promising leads.

Accordingly, in one aspect the invention provides a method of modulating stress granule formation, the method comprising contacting a cell with a modulator of stress granule. As used herein, the terms "modulator of stress granule" and "stress granule modulator" refer to compounds and compositions that modulate the formation and/or disaggregation of stress granules.

In one aspect, the invention provides methods for treatment of a neurodegenerative disease or disorder, a cancer, and/or a viral infection in a subject, the method comprising administering a stress granule modulator to a subject in need thereof.

In another aspect, the invention provides methods of diagnosing a neurodegenerative disease in a subject, the method comprising administering a stress granule marker to the subject. For use in diagnosing a stress granule marker can be labeled with a label.

In another aspect, the invention provides methods of modulating stress granules comprising contacting a cell with a TDP-43 inclusion inhibiting compound.

In another aspect, the invention provides methods of modulating TDP-43 inclusion formation comprising contacting a cell with a TDP-43 inclusion inhibitor.

In yet another aspect, the invention provides a method of screening for modulators of TDP-43 aggregation comprising contacting a compound with the cell that expresses TDB-43 and develops spontaneous inclusions.

In still another aspect, the invention provides a cell that expresses wild-type TDB-43 and develops spontaneous inclusions.

In some embodiments, the stress granule modulator inhibits the formation of a stress granule. The stress granule modulator can inhibit the formation of a stress granule by at least 10%, at least 20%, at least 30%, at least 40%, at least 50%, at least 60%, at least 70%, at least 80%, at least 90%, at least 95%, or 100% (i.e., complete inhibition) relative to a control.

In some embodiments, the stress granule modulator disaggregates a stress granule. The stress granule modulator can disperses or disaggregate a stress granule by at least 10%, at least 20%, at least 30%, at least 40%, at least 50%, at least 60%, at least 70%, at least 80%, at least 90%, at least 95%, or 100% (i.e., complete dispersal) relative to a control.

In some embodiments, the stress granule comprises TDP-43, i.e., is a TDP-43 inclusion. Accordingly, in some embodiments, a modulator of stress granule is a modulator of TDP-43 inclusions. As used herein, the terms "modulator of TDP-43 inclusion" and "TDP-43 inclusion modulator" refer to compounds and compositions that modulate the formation and/or disaggregation of cytoplasmic TDP-43 inclusions. By TDP-43 inclusion is meant protein-mRNA aggregates comprise a TDP-43 protein. The TDP-43 protein in a stress granule can be wild-type or a mutant form of TDP-43

In some embodiments, the stress granule comprises a mutant FUS protein.

In some embodiments, TDP-43 is inducibly expressed.

In some embodiments, the cell line is a neuronal cell line.

In some embodiments, the cell is treated with a physiochemical stressor. In some embodiments, the physicochemical stressor is selected from arsenite, nutrient deprivation, heat shock, osmotic shock, a virus, genotoxic stress, radiation, oxidative stress, oxidative stress, a mitochondrial inhibitor, and an endoplasmic reticular stressor. In some embodiments, the physicochemical stressor is ultraviolet or x-ray radiation. In some embodiments, the physicochemical stressor is oxidative stress induced by $FeCl_2$ or $CuCl_2$ and a peroxide.

Method of Treatment

In another aspect, the invention provides a method for treatment of a neurodegenerative disease or disorder, a caner, and/or a viral infections, the method comprising administering an effective amount of a modulator of stress granule formation to a subject in need thereof.

In some embodiments, stress granule formation is inhibited. In some embodiments, the stress granule is disaggregated. In some embodiments, stress granule formation is stimulated.

In some embodiments, the stress granule comprises tar DNA binding protein-43 (TDP-43), T-cell intracellular antigen 1 (TIA-1), TIA1 cytotoxic granule-associated RNA binding protein-like 1 (TIAR), GTPase activating protein binding protein 1 (G3BP-1), GTPase activating protein binding protein 2 (G3BP-2), tristetraprolin (TTP) (which also has the gene name of ZFP36 (zinc finger protein 36, C3H type, homolog (mouse)), Fused in Sarcoma (FUS) or Translocated in Liposarcoma Protein (TLS), or fragile X mental retardation protein (FMRP).

In some embodiments, the stress granule comprises tar DNA binding protein-43 (TDP-43), T-cell intracellular antigen 1 (TIA-1), TIA1 cytotoxic granule-associated RNA binding protein-like 1 (TIAR), GTPase activating protein binding protein 1 (G3BP-1), GTPase activating protein binding protein 2 (G3BP-2), fused in sarcoma (FUS), or fragile X mental retardation protein (FMRP).

In some embodiments, the stress granule comprises tar DNA binding protein-43 (TDP-43), T-cell intracellular antigen 1 (TIA-1), TIA1 cytotoxic granule-associated RNA binding protein-like 1 (TIAR), GTPase activating protein binding protein 1 (G3BP-1), GTPase activating protein binding protein 2 (G3BP-2), or fused in sarcoma (FUS).

In some embodiments, the stress granule comprises tar DNA binding protein-43 (TDP-43).

In some embodiments, the stress granule comprises T-cell intracellular antigen 1 (TIA-1).

In some embodiments, the stress granule comprises TIA1 cytotoxic granule-associated RNA binding protein-like 1 (TIAR).

In some embodiments, the stress granule comprises GTPase activating protein binding protein 1 (G3BP-1).

In some embodiments, the stress granule comprises GTPase activating protein binding protein 2 (G3BP-2).

In some embodiments, the stress granule comprises tris tetraprolin (TTP).

In some embodiments, the stress granule comprises fused in sarcoma (FUS).

In some embodiments, the stress granule comprises fragile X mental retardation protein (FMRP).

In some embodiments, the methods are performed in a subject suffering from a neurodegenerative disease or disorder, a cancer, and/or a viral infection. In some embodiments, the methods are performed in a subject suffering from a neurodegenerative disease or disorder. In some embodiments, the methods are performed in a subject suffering from a cancer. In some embodiments, the methods are performed in a subject suffering from a viral infection.

In some embodiments, the methods comprise administering a stress granule modulator to a subject in need thereof. In some embodiments, the subject is a mammal. In some embodiments, the subject is a nematode. In some embodiments, the subject is human.

In some embodiments, the methods further comprise the step of diagnosing the subject for the neurodegenerative disease or disorder prior to onset of administration of a stress granule modulator.

In some embodiments, the neurodegenerative disease is selected from the group consisting of Alzheimer's disease, frontotemporal dementia, FTLD-U (a frontotemporal dementia caused by mutations in progranulin protein), amyotrophic lateral sclerosis (ALS), Huntington's chorea, Creutzfeld-Jacob disease, trinucleotide repeat diseases, cerebral degenerative diseases presenile dementia, senile dementia, Parkinsonism linked to chromosome 17 (FTDP-17), progressive supranuclear palsy (PSP), Huntington's disease (HD), Pick's disease, primary progressive aphasia, corticobasal dementia, Parkinson's disease, Parkinson's disease with dementia, dementia with Lewy bodies, Down's syndrome, multiple system atrophy, spinal muscular atrophy (SMA), spinocerebellar ataxia, spinal degenerative disease/motor neuron degenerative diseases, Hallervorden-Spatz syndrome, cerebral infarct, cerebral trauma, chronic traumatic encephalopathy, transient ischemic attack, and any combination thereof.

In some embodiments, the neurodegenerative disease is selected from the group consisting of Alzheimer's disease, frontotemporal dementia, FTLD-U (a frontotemporal dementia caused by mutations in progranulin protein), amyotrophic lateral sclerosis (ALS), Huntington's chorea, Creutzfeld-Jacob disease, senile dementia, Parkinsonism linked to chromosome 17 (FTDP-17), progressive supranuclear palsy (PSP), Huntington's disease (HD), Pick's disease, primary progressive aphasia, corticobasal dementia, Parkinson's disease, Parkinson's disease with dementia, dementia with Lewy bodies, Down's syndrome, multiple system atrophy, spinal muscular atrophy (SMA), spinocerebellar ataxia, spinal degenerative disease/motor neuron degenerative diseases, Hallervorden-Spatz syndrome, cerebral infarct, cerebral trauma, chronic traumatic encephalopathy, transient ischemic attack, and any combination thereof.

In some embodiments, the neurodegenerative disease is Alzheimer's disease or amyotrophic lateral sclerosis (ALS).

In some embodiments, the cancer is selected from the group consisting of breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, vulval cancer, and any combination thereof.

In some embodiments, the cancer is selected from the group consisting of blastoma, carcinoma, a glioblastoma, hepatic carcinoma, leukemia, and any combination thereof.

In some embodiments, the viral infection is caused by a virus selected from the group consisting of West Nile virus, Respiratory Syncitial Virus (RSV), herpes simplex virus 1, herpes simplex virus 2, Epstein-Barr virus (EBV), hepatitis virus A, hepatitis virus B, hepatitis virus C, influenza viruses, chicken pox, avian flu viruses, smallpox, polio viruses, HIV-1, HIV-2, and any combination thereof.

In some embodiments, the viral infection is caused by a virus selected from the group consisting of herpes simplex virus 1, herpes simplex virus 2, Epstein-Barr virus (EBV), hepatitis virus A, hepatitis virus B, hepatitis virus C, HIV-1, HIV-2, and any combination thereof.

In some embodiments, the viral infection is HIV-1 or HIV-2.

In some embodiments, the pathology of the neurodegenerative disease or disorder, cancer, and/or viral infection comprises stress granules.

In some embodiments, pathology of the disease or disorder comprises stress granules. By comprising stress granules is meant that number of stress granules in a cell in the subject is changed relative to a control and/or healthy subject or relative to before onset of said disease or disorder. Exemplary diseases and disorders pathology of which incorporate stress granules include, but are not limited to, neurodegenerative diseases, cancers, and viral infections.

Stress response follows a U shaped curve. Too much (such as is induced in neurodegenerative diseases) is bad. Too little, though, is also bad under other conditions (such as with an acute stress such as a stroke). Thus some diseases benefit from inhibiting stress granule formation, while other diseases benefit from stimulating stress granule formation.

TDP-43 and other RNA-binding proteins appear to act in the cytoplasm to process mRNA, such as by splicing mRNA, cleaving mRNA introns, cleaving untranslated regions of mRNA or modifying protein translation at the synapse, axon, dendrite or soma. For instance, FMPR is a protein that causes mental retardation, and the signaling systems that affect TDP-43 might also affect this protein and improve cognitive function. This can be particularly important at the synapse where neurons communicate. Without wishing to be bound by a theory, the signaling systems that modulators of TDP-43 inclusions target can also modify these processes. These processes could play a role in neurodegeneration or mental health illnesses (e.g., schizophrenia). Thus, modulators of TDP-43 inclusions can also act by modifying these RNA processing and protein translation processes.

Neurodegenerative Diseases:

Without wishing to be bound by a theory, modulators of TDP-43 inclusions, such as stress granules, can be used to delay the progression of neurodegenerative illnesses where the pathology incorporates stress granules. Such illnesses include ALS (where mutations in TDP-43 cause ALS), and frontotemporal dementia (where TDP-43 is the main protein that accumulates) where TDP-43 is the main protein that accumulates to form the pathology. This group also includes Alzheimer's disease and FTLD-U (a frontotemporal dementia caused by mutations in tau protein), where TDP-43 and other stress granule proteins co-localize with tau pathology. Because modulators of TDP-43 inclusions can act to block the enzymes that SIGNAL stress granule formation, such as the three enzymes that phosphorylate eIF2a-PERK, GCN2 and HRI, modulators of TDP-43 inclusions can also reverse stress granules that might not include TDP-43. Accordingly, modulators of TDP-43 can be used for treatment of neurodegenerative diseases and disorders pathology of which incorporates stress granules. This can include Huntington's chorea and Creutzfeld-Jacob disease—both quite rare.

The term "neurodegenerative disease" as used herein, refers to a neurological disease characterized by loss or degeneration of neurons. The term "neurodegenerative disease" includes diseases caused by the involvement of genetic factors or the cell death (apoptosis) of neurons attributed to abnormal protein accumulation and so on. Additionally, neurodegenerative diseases include neurodegenerative movement disorders and neurodegenerative conditions relating to memory loss and/or dementia. Neurodegenerative diseases include tauopathies and a-synucleopathies. Exemplary neurodegenerative diseases include, but are not limited to, Alzheimer's disease, frontotemporal dementia, FTLD-U (a frontotemporal dementia caused by mutations in tau protein), amyotrophic lateral sclerosis (ALS), Huntington's chorea, Creutzfeld-Jacob disease, trinucleotide repeat diseases, cerebral degenerative diseases presenile dementia, senile dementia, Parkinsonism linked to chromosome 17 (FTDP-17), progressive supranuclear palsy (PSP), Huntington's disease (HD), Pick's disease, primary progressive aphasia, corticobasal dementia, Parkinson's disease, Parkinson's disease with dementia, dementia with Lewy bodies, Down's syndrome, multiple system atrophy, spinal muscular atrophy (SMA), spinocerebellar ataxia, spinal degenerative disease/motor neuron degenerative diseases, and Hallervorden-Spatz syndrome.

As used herein, the term "α-synucleopathy" refers to a neurodegenerative disorder or disease involving aggregation of a-synuclein or abnormal a-synuclein in nerve cells in the brain. a-Synucleopathies include, but are not limited to, Parkinson's disease, Parkinson's disease with dementia, dementia with Lewy bodies, Pick's disease, Down's syndrome, multiple system atrophy, amylotrophic lateral sclerosis (ALS) and Hallervorden-Spatz syndrome.

Cancers:

Cancer cells grow quickly and in low oxygen environments by activating different elements of their stress response. Researchers have shown that drugs targeting different elements of the stress response can be anti-neoplastic. Rapamycin blocks mTOR, upregulates autophagy and inhibits some types of tumors. Proteasomal inhibitors, such as velcade (Millenium Pharma) are used to treat some cancers ($1 billion/yr). HSP90 inhibitors, such as 17-allylaminogeldanamycin (17AAG), are in clinical trials for cancer. Without wishing to be bound by a theory, modulators of TDP-43 inclusions can also be used for treatment of cancer. Additionally, TDP-43 modulators ca be combined with one or more cancer therapies, such as chemotherapy and radiation therapy.

A "cancer" in subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. In some circumstances, cancer cells will be in the form of a tumor; such cells may exist locally within an animal, or circulate in the blood stream as independent cells, for example, leukemic cells. Examples of cancer include but are not limited to breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, vulval cancer, and the like.

Other exemplary cancers include, but are not limited to, ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva, Wilm's tumor, and the like Viral Infections:

SGs often form during viral illnesses. Accordingly, some viruses might mobilize SGs to subvert the cellular machinery towards production of viral proteins. In this case, inhibitors of stress granules can be useful for interfering with viral function. Other viruses appear to inhibit SG formation to prevent the cell from mobilizing a stress response. In such a case, inducer of stress granules can interfere with viral activity and help combat viral infections. One exemplary stress granule inducer is Salubrinal, a PERK inhibitor. Two viruses for which SG biology has been investigated include West Nile virus and Respiratory Syncitial Virus (RSV). See for example. M. E Emara & M. A. Brinton, *Proc. Natl. Acad. Sci. USA*, 104(21): 9041-9046 (2007); incorporated herein by reference in its entirety.

Exemplary viruses include, but are not limited to, West Nile virus, Respiratory Syncitial Virus (RSV), Epstein-Barr virus (EBV, a member of the herpesvirus family), the hepatitis A, B, C, and D viruses, influenza viruses, chicken pox, avian flu viruses, smallpox, polio viruses, HIV, and the like.

Imaging

The compounds described herein are useful for detection and/or diagnosis of stress granules. Accordingly, they can be used as in vivo imaging agents of tissues and organs in various biomedical applications. When used in imaging applications, the compounds described herein typically comprise an imaging agent, which can be covalently or noncovalently attached to the compound.

As used herein, the term "imaging agent" refers to an element or functional group in a molecule that allows for the detection, imaging, and/or monitoring of the presence and/or progression of a condition(s), pathological disorder(s), and/or disease(s). The imaging agent may be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber.

Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorescent reporters include xanthene dyes, such as fluorescein or rhodamine dyes, including, but not limited to, Alexa Fluor® dyes (InvitrogenCorp.; Carlsbad, Calif.), fluorescein, fluorescein isothiocyanate (FITC), Oregon Green™, rhodamine, Texas red, tetrarhodamine isothiocynate (TRITC), 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N',N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylamino-naphthyl-5-sulfonate, 1-anilino-8-naphthalene sulfonate, 2-p-toluidinyl-6-naphthalene sulfonate, and 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p (2-benzoxazolyl)phenyl)maleimide; cyanines, such as Cy2, indodicarbocyanine 3 (Cy3), indodicarbocyanine 5 (Cy5), indodicarbocyanine 5.5 (Cy5.5), 3-(-carboxy-pentyl)-3' ethyl-5,5'-dimethyloxacarbocyanine (CyA); 1H, 5H, 11H, 15H-Xantheno[2,3,4-ij:5,6,7-i'j']diquinolizin-18-ium, 9-[2 (or 4)-[[[6-[2,5-dioxo-1-pyrrolidinyl)oxy]-6-oxohexyl] amino]sulfonyl]-4(or 2)-sulfophenyl]-2,3,6,7,12,13,16, 17octahydro-inner salt (TR or Texas Red); BODIPY™ dyes; benzoxadiazoles; stilbenes; pyrenes; and the like. Many suitable forms of these fluorescent compounds are available and can be used.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566; each herein incorporated by reference in its entirety). Specific examples of GFP variants include, but are not limited to, enhanced GFP (EGFP), destabilized EGFP, the GFP variants described in Doan et al, *Mol. Microbiol,* 55:1767-1781 (2005), the GFP variant described in Crameri et al, *Nat. Biotechnol.,* 14:315319 (1996), the cerulean fluorescent proteins described in Rizzo et al, *Nat. Biotechnol,* 22:445 (2004) and Tsien, *Annu. Rev. Biochem.,* 67:509 (1998), and the yellow fluorescent protein described in Nagal et al, *Nat. Biotechnol.,* 20:87-90 (2002) (each herein incorporated by reference in its entirety). DsRed variants are described in, e.g., Shaner et al, *Nat. Biotechnol.,* 22:1567-1572 (2004) (herein incorporated by reference in its entirety), and include mStrawberry, mCherry, morange, mBanana, mHoneydew, and mTangerine. Additional DsRed variants are described in, e.g., Wang et al, *Proc. Natl. Acad. Sci. U.S.A.,* 101:16745-16749 (2004) (herein incorporated by reference in its entirety), and include mRaspberry and mPlum. Further examples of DsRed variants include mRFPmars described in Fischer et al, *FEBS Lett.*, 577:227-232 (2004) and mRFPruby described in Fischer et al, *FEBS Lett*, 580:2495-2502 (2006) (each herein incorporated by reference in its entirety).

Suitable echogenic gases include, but are not limited to, a sulfur hexafluoride or perfluorocarbon gas, such as perfluoromethane, perfluoroethane, perfluoropropane, perfluorobutane, perfluorocyclobutane, perfluoropentane, or perfluorohexane.

Suitable non-metallic isotopes include, but are not limited to, $^{11}C$, $^{14}C$, $^{13}N$, $^{18}F$, $^{123}I$, $^{124}I$, and $^{125}I$.

Suitable radioisotopes include, but are not limited to, $^{99}mTc$, $^{95}Tc$, $^{111}In$, $^{62}Cu$, $^{64}Cu$, Ga, $^{68}Ga$, and $^{153}Gd$.

Suitable paramagnetic metal ions include, but are not limited to, Gd(III), Dy(III), Fe(III), and Mn(II).

Suitable X-ray absorbers include, but are not limited to, Re, Sm, Ho, Lu, Pm, Y, Bi, Pd, Gd, La, Au, Au, Yb, Dy, Cu, Rh, Ag, and Ir.

In some embodiments, the radionuclide is bound to a chelating agent or chelating agent-linker attached to the aggregate. Suitable radionuclides for direct conjugation include, without limitation, $^{18}F$, $^{124}I$, $^{125}I$, $^{131}I$, and mixtures thereof. Suitable radionuclides for use with a chelating agent include, without limitation, $^{47}Sc$, $^{64}Cu$, $^{67}Cu$, $^{89}Sr$, $^{86}Y$, $^{87}Y$, $^{90}Y$, $^{105}Rh$, $^{111}Ag$, $^{111}In$, $^{117m}Sn$, $^{149}Pm$, $^{153}Sm$, $^{166}Ho$, $^{177}Lu$, $^{186}Re$, $^{188}Re$, $^{211}At$, $^{212}Bi$, and mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to the nanoparticles.

A detectable response generally refers to a change in, or occurrence of, a signal that is detectable either by observation or instrumentally. In certain instances, the detectable response is fluorescence or a change in fluorescence, e.g., a change in fluorescence intensity, fluorescence excitation or emission wavelength distribution, fluorescence lifetime, and/or fluorescence polarization. One of skill in the art will appreciate that the degree and/or location of labeling in a subject or sample can be compared to a standard or control (e.g., healthy tissue or organ). In certain other instances, the detectable response the detectable response is radioactivity (i.e., radiation), including alpha particles, beta particles, nucleons, electrons, positrons, neutrinos, and gamma rays emitted by a radioactive substance such as a radionuclide.

Specific devices or methods known in the art for the in vivo detection of fluorescence, e.g., from fluorophores or fluorescent proteins, include, but are not limited to, in vivo near-infrared fluorescence (see, e.g., Frangioni, *Curr. Opin. Chem. Biol*, 7:626-634 (2003)), the Maestro™ in vivo fluorescence imaging system (Cambridge Research & Instrumentation, Inc.; Woburn, Mass.; herein incorporated by reference in its entirety), in vivo fluorescence imaging using a flying-spot scanner (see, e.g., Ramanujam et al, *IEEE Transactions on Biomedical Engineering*, 48:1034-1041 (2001); herein incorporated by reference in its entirety, and the like. Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled aggregate. Positron emission tomography (PET) is another suitable technique for detecting radiation in a subject.

Magnetic resonance imaging (MRI), nuclear magnetic resonance imaging (NMRI), or magnetic resonance tomography (MRT) is a medical imaging technique used in radiology to visualize detailed internal structures. MRI makes use of the property of Nuclear magnetic resonance (NMR) to image nuclei of atoms inside the body. Thus, labels having magnetic properties can be detected using MRI and/or related technologies.

SG proteins, such as TDP-43, undergo translocation to the cytoplasm and aggregate. Translocation likely requires a post-translational modification as well as binding to a transport protein. Aggregation is associated with a change in protein conformation. Modulators of TDP-43 can bind to SG proteins specifically under states of cytoplasmic translocation (for instance, because they recognize a binding site enabled by a post-translational modification) or SG proteins that are in an aggregated state associated with SGs. Thus, modulators of TDP-43 inclusions can be used image areas in a subject's body that have increased levels of SGs—either physiological or pathological. For instance, in ALS and Alzheimer's disease, inventors have demonstrated that TDP-43 associates with the pathology that accumulates. Thus, compounds that recognize aggregated TDP-43 can be used to image pathology, much like the imaging agent PiB, which is currently used in Alzheimer's research. However, PiB has a problem because it recognizes amyloid, whose accumulation occurs both in patients with Alzheimer's disease and in many non-demented people. However, an agent that recognizes SGs would specifically identify patients that have intracellular pathology (such as neurofibrillary tangles, which the inventor has shown are associated with SGs). Such agents can be used to diagnose patients with or at risk for neurodegenerative illnesses.

Additionally, imaging of SGs in a subject can be used to localize pain. For example, a modulator can be administered to a subject having a pain and the pain is difficult to localize, and subsequent imaging can localize the area of the body that is diseased or injured. This can greatly speed diagnosis and can be generally applicable throughout the medical arts.

Further, the compounds described herein can be used to image organs for transplants. Organs are harvested for transplants—such as kidneys and hearts. A problem in the field is that surgeons don't know how well the organ survived the harvesting and transport to the receiving hospital. Sometimes, organs are transplanted only to have them fail because they were injured in transport. A quick cytologic stain with a stress granule marker can be a large advance for the field. Accordingly, modulators of TDP-43 inclusions can be used as stress granule markers.

Modulators

In some embodiments, the compound is of formula (I):

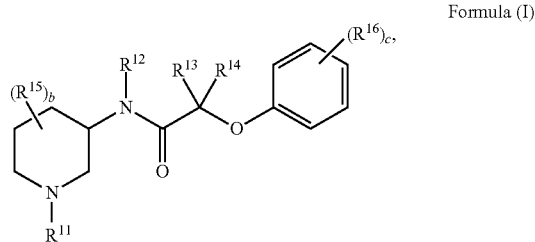

Formula (I)

and analogs, derivatives, isomers, prodrugs, and pharmaceutically acceptable salts thereof.

In one embodiment, the compound is of formula (I). In another embodiment, the compound is an isomer of formula (I). In still another embodiment, the compound is an analog of formula (I). In yet another embodiment, the compound is a prodrug of a compound of formula (I). In another embodiment, the compound is a pharmaceutically acceptable salt of a compound of formula (I).

In compounds of formula (I), $R^{11}$ and $R^{12}$ are independently H, alkyl, alkenyl, alkynyl, cyclyl, heterocyclyl, aryl, heteroaryl, $C(O)R^{17}$, or $C(O)OR^{17}$, each of which can be optionally substituted. In some embodiments, $R^{11}$ is an optionally substituted aryl or heteroaryl.

In one embodiment, $R^{11}$ is an optionally substituted pyridinyl. The pyridinyl group can be substituted at the 2, 3, 4, 5, 6, or any combinations of those positions. When the pyridinyl group is substituted by two or more substituents, said two or more substituents can be same, all different, or a combination of same and different substituents. Additionally, the pyridinyl group can be attached to the rest of formula (I) by 2, 3, 4, 5, or 6 positions. In one embodiment of this, $R^{11}$ is

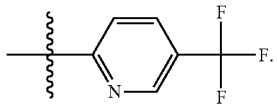 [SMILES: *c1ccc(C(F)(F)F)cn1]

In another embodiment, $R^{11}$ is an optionally substituted benzothiazolyl. The benzothiazolyl group can be substituted at the 2, 4, 5, 6, 7, or any combinations of those positions. When the benzothiazolyl group is substituted by two or more substituents, said two or more substituents can be same, all different, or a combination of same and different substituents. Additionally, the benzothiazolyl group can be attached to the rest of formula (I) by 2, 4, 5, 6, or 7 position. In one embodiment of this $R^{11}$ is

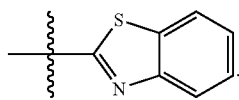 [SMILES: *c1nc2ccccc2s1]

In some embodiments, $R^{12}$ is H or an optionally substituted $C_1$-$C_6$ alkyl.

In compounds of formula (I), $R^{13}$ and $R^{14}$ are independently H, alkyl, alkenyl, alkynyl, cyclyl, heterocyclyl, aryl, heteroaryl, $OR^{17}$, $C(O)R^{17}$, or $C(O)OR^{17}$, $N(R^{17})_2$, each of which can be optionally substituted.

In one embodiment, at least one of $R^{13}$ and $R^{14}$ is H. When $R^{13}$ and $R^{14}$ are different, the carbon atom to which they are attached is chiral. Thus, when $R^{13}$ and $R^{14}$ are different from each other, the carbon to which they are attached can have the R— or the S— configuration.

In another embodiment, both of $R^{13}$ and $R^{14}$ are H.

Variable b, in the compounds of formula (I), can be 0, 1, 2, 3, or 4. In one embodiment b is 0.

When present each $R^{15}$ is independently, halo, alkyl, alkenyl, cyclyl, heterocyclyl, aryl, heteroaryl, $NO_2$, $OR^{17}$, $OC(O)R^{17}$, $OC(O)OR^{17}$, $N(R^{17})_2$, $NHC(O)R^{17}$, $NHC(O)OR^{17}$, $C(O)R^{17}$, $C(O)OR^{17}$, $SR^{17}$, or $SO_2R^{17}$, each of which can be optionally substituted.

The variable c, in the compounds of formula (I), can be 0, 1, 2, 3, 4, or 5. It is to be understood that when present a $R^{16}$ substituent can be located at the 2, 3, 4, 5, or 6 position of the phenyl group. When more than one $R^{16}$ is present, they can be located at any combination of 2, 3, 4, 5, and 6 positions of the phenyl group. In one embodiment of this, when b is 1, substituent $R^{16}$ is located at position 2 of the phenyl group. Accordingly, a compound of formula (I) is of formula (Ia):

Formula (Ia)

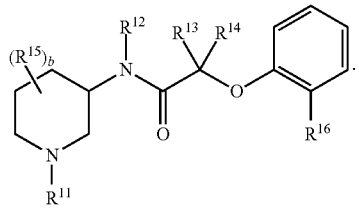

When present, each $R^{16}$ is independently, halo, alkyl, alkenyl, cyclyl, heterocyclyl, aryl, heteroaryl, $NO_2$, $OR^{17}$, $OC(O)R^{17}$, $OC(O)OR^{17}$, $N(R^{17})_2$, $NHC(O)R^{17}$, $NHC(O)OR^{17}$, $C(O)R^{17}$, $C(O)OR^{17}$, $SR^{17}$, or $SO_2R^{17}$, each of which can be optionally substituted. In one embodiment, $R^{16}$ is $OR^{17}$. In one embodiment, $R^{16}$ is methoxy.

In compounds of formula (I), substituent $R^{17}$ is independently for each occurrence, H, alkyl, alkenyl, alkynyl, cyclyl, heterocyclyl, aryl, or heteroaryl, each of which can be optionally substituted. In one embodiment, $R^{17}$ is an optionally substituted $C_1$-$C_6$ alkyl. In one further embodiment of this, $R^{17}$ is a methyl, ethyl, propyl, or butyl.

Compounds of formula (I) can be synthesized by following the outlined shown in Scheme I.

Scheme I

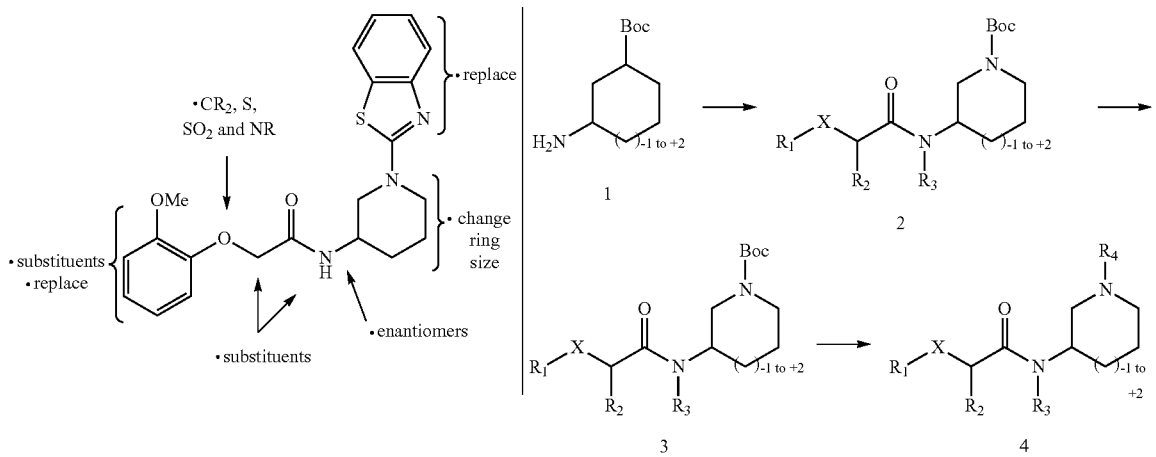

In one embodiment, a compound of formula (I) is LDN-0118790 or LDN-0121669. Structure of LDN-0118790 is shown in FIG. 2 and structure of LDN-0121669 is shown in FIG. 3.

In one embodiment, a compound of formula (I) is an analog of LDN-0118790 or LDN-0121669.

In one embodiment, a compound of formula (I) is an isomer of LDN-0118790 or LDN-0121669.

In one embodiment, a compound of formula (I) is a prodrug of LDN-0118790 or LDN-0121669.

In one embodiment, a compound of formula (I) is a pharmaceutically acceptable salt of LDN-0118790 or LDN-0121669.

In some embodiments, the compound is of formula (II):

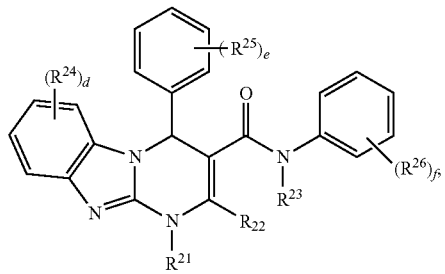

Formula (II)

and analogs, derivatives, isomers, prodrugs, and pharmaceutically acceptable salts thereof.

In one embodiment, the compound is of formula (II). In another embodiment, the compound is an isomer of formula (II). In still another embodiment, the compound is an analog of formula (II). In yet another embodiment, the compound is a prodrug of a compound of formula (II). In another embodiment, the compound is a pharmaceutically acceptable salt of a compound of formula (II).

In compounds of formula (II), $R^{21}$ and $R^{23}$ are independently H, alkyl, alkenyl, alkynyl, cyclyl, heterocyclyl, aryl, heteroaryl, $C(O)R^{27}$, or $C(O)OR^{27}$, each of which can be optionally substituted. In some embodiments, $R^{21}$ and $R^{23}$ are both H.

Substituent $R^{22}$ can be H or alkyl. In some embodiments, $R^{22}$ is an optionally substituted $C_1$-$C_6$ alkyl. In one further embodiment of this, $R^{22}$ is methyl or ethyl.

When present, $R^{24}$, $R^{25}$, and $R^{26}$ are independently halo, alkyl, alkenyl, cyclyl, heterocyclyl, aryl, heteroaryl, $NO_2$, $OR^{27}$, $OC(O)R^{27}$, $OC(O)OR^{27}$, $N(R^{27})_2$, $NHC(O)R^{27}$, $NHC(O)OR^{27}$, $C(O)R^{27}$, $C(O)OR^{27}$, $SR^{27}$, or $SO_2R^{27}$, each of which can be optionally substituted. In one embodiment, both of $R^{25}$ and $R^{26}$ are $OR^{27}$. In one embodiment, both of $R^{25}$ and $R^{26}$ are methoxy.

It is to be understood that when present, $R^{24}$, $R^{25}$, and $R^{26}$ can be attached any position on the ring they are linked to. For example, $R^{25}$ and/or $R^{26}$ substituents can be attached to position 2, 3, 4, 5, or 6 position of the phenyl group. When more than one of $R^{25}$ or $R^{26}$ is present, they can be located at any combination of 2, 3, 4, 5, and 6 positions of the respective phenyl group. Additionally, when two or more of $R^{24}$ are present all can be same, all different, or a combination of same and different. Similarly, when two or more of $R^{25}$ are present all can be same, all different, or a combination of same and different. Likewise, when two or more of $R^{26}$ are present all can be same, all different, or a combination of same and different.

Variable d can be 0, 1, 2, 3, or 4. In one embodiment, d is 0.

Variables e and f are independently 0, 1, 2, 3, 4, or 5. In one embodiment both of e and f are 1. In one embodiment, when e is 1, $R^{25}$ is attached to position 4 of the phenyl group.

In one embodiment, when f is 1, $R^{26}$ is attached to position 2 of the phenyl group.

In some embodiments, a compound of formula (II) is of formula (IIa):

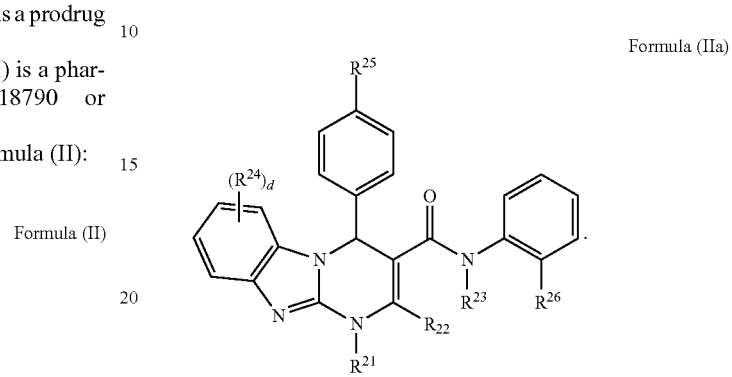

Formula (IIa)

Substituent $R^{27}$ in compounds of formula (II) is independently for each occurrence H, alkyl, alkenyl, alkynyl, cyclyl, heterocyclyl, aryl, or heteroaryl, each of which can be optionally substituted. In one embodiment, $R^{27}$ is an optionally substituted $C_1$-$C_6$ alkyl. In one further embodiment of this, $R^{27}$ is a methyl, ethyl, propyl, or butyl.

In one embodiment, a compound of formula (II) is LDN-0124614 as shown in FIG. 4.

In one embodiment, a compound of formula (I) is an analog of LDN-0124614.

In one embodiment, a compound of formula (I) is an isomer of LDN-0124614.

In one embodiment, a compound of formula (I) is a prodrug of LDN-0124614.

In one embodiment, a compound of formula (I) is a pharmaceutically acceptable salt of LDN-0124614.

In some embodiments, the compound is of formula (III):

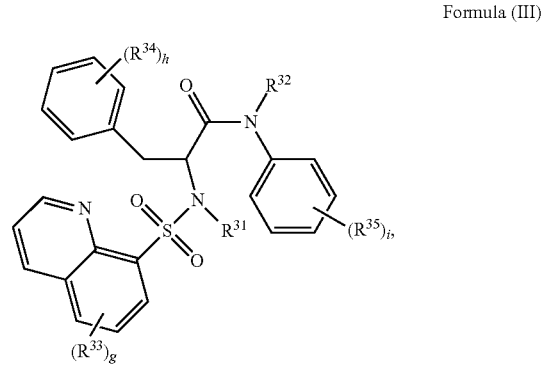

Formula (III)

and analogs, derivatives, isomers, prodrugs, and pharmaceutically acceptable salts thereof.

In one embodiment, the compound is of formula (III). In another embodiment, the compound is an isomer of formula (III). In still another embodiment, the compound is an analog of formula (III). In yet another embodiment, the compound is a prodrug of a compound of formula (III). In another embodiment, the compound is a pharmaceutically acceptable salt of a compound of formula (III).

In compounds of formula (III), $R^{31}$ and $R^{32}$ are independently, H, alkyl, alkenyl, alkynyl, cyclyl, heterocyclyl, aryl, heteroaryl, $C(O)R^{36}$, or $C(O)OR^{36}$, each of which can be optionally substituted. In some embodiments, $R^{31}$ and $R^{32}$ are both H.

When present, $R^{33}$, $R^{34}$, and $R^{35}$ are independently halo, alkyl, alkenyl, cyclyl, heterocyclyl, aryl, heteroaryl, $NO_2$, $OR^{36}$, $OC(O)R^{36}$, $OC(O)OR^{36}$, $N(R^{36})_2$, $NHC(O)R^{36}$, $NHC(O)OR^{36}$, $C(O)R^{36}$, $C(O)OR^{36}$, $SR^{36}$, or $SO_2R^{36}$, each of which can be optionally substituted. In one embodiment, $R^{35}$ is alkyl or $OR^{36}$. In one embodiment, $R^{35}$ is ethyl or methoxy.

It is to be understood that when present, $R^{33}$, $R^{34}$, and $R^{36}$ can be attached to any available position on the ring they are linked to. For example, $R^{34}$ and/or $R^{35}$ substituents can be attached to position 2, 3, 4, 5, or 6 position of the phenyl group. When more than one of $R^{34}$ or $R^{35}$ is present, they can be located at any combination of 2, 3, 4, 5, and 6 positions of the respective phenyl group. Additionally, when two or more of $R^{33}$ are present all can be same, all different, or a combination of same and different. Similarly, when two or more of $R^{34}$ are present all can be same, all different, or a combination of same and different. Likewise, when two or more of $R^{35}$ are present all can be same, all different, or a combination of same and different.

Variable g in compounds of formula (III) can be 0, 1, 2, 3, 4, 5, 6, or 7. In one embodiment, g is 0.

Variables h and i in compounds of formula (III) are independently 0, 1, 2, 3, 4, or 5. In some embodiments, h is 0. In some other embodiments, i is 1. In one embodiment, h is 0 and i is 1.

When i is 1, $R^{35}$ can be attached to position 2, 3, 4, 5, or 6 of the phenyl group. In one embodiment, $R^{35}$ is attached at position 4 of the phenyl group.

Substituent $R^{36}$ is independently for each occurrence H, alkyl, alkenyl, alkynyl, cyclyl, heterocyclyl, aryl, or heteroaryl, each of which can be optionally substituted. In one embodiment, $R^{36}$ is an optionally substituted $C_1$-$C_6$ alkyl. In one further embodiment of this, $R^{36}$ is a methyl, ethyl, propyl, or butyl.

In some embodiments, a compound of formula (III) is of formula (IIIa):

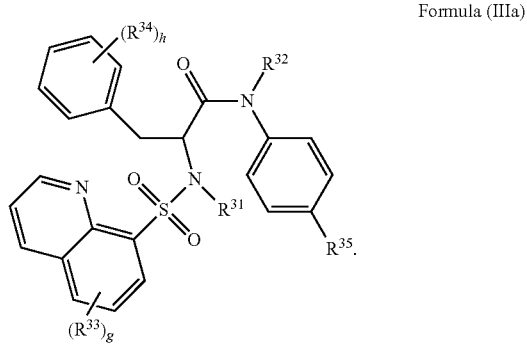

Formula (IIIa)

In one embodiment, a compound of formula (III) is LDN-0125734, shown in FIG. 5, or LDN-01215735, shown in FIG. 6.

In one embodiment, a compound of formula (III) is an analog of LDN-0125734 or LDN-01215735.

In one embodiment, a compound of formula (III) is an isomer of LDN-0125734 or LDN-01215735.

In one embodiment, a compound of formula (III) is a prodrug of LDN-0125734 or LDN-01215735.

In one embodiment, a compound of formula (III) is a pharmaceutically acceptable salt of LDN-0125734 or LDN-01215735.

In some embodiments, the compound is of formula (IV):

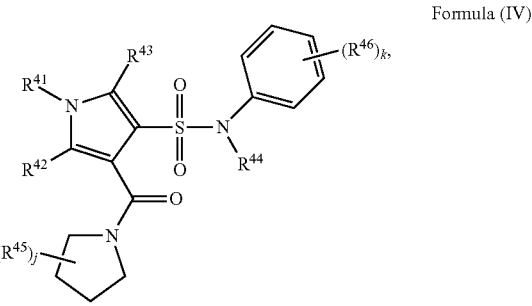

Formula (IV)

and analogs, derivatives, isomers, prodrugs, and pharmaceutically acceptable salts thereof.

In one embodiment, the compound is of formula (IV). In another embodiment, the compound is an isomer of formula (IV). In still another embodiment, the compound is an analog of formula (IV). In yet another embodiment, the compound is a prodrug of a compound of formula (IV). In another embodiment, the compound is a pharmaceutically acceptable salt of a compound of formula (IV).

$R^{41}$ is H, alkyl, alkenyl, alkynyl, cyclyl, heterocyclyl, aryl, heteroaryl, $C(O)R^{47}$, $C(O)OR^{47}$, $SO_2R^{47}$, each of which can be optionally substituted. In some embodiments, $R^{41}$ is H or $C_1$-$C_6$ alkyl. In one embodiment, $R^{41}$ is methyl.

$R^{42}$ and $R^{43}$ are independently H, halo, alkyl, alkenyl, cyclyl, heterocyclyl, aryl, heteroaryl, $NO_2$, $OR^{47}$, $OC(O)R^{47}$, $OC(O)OR^{47}$, $N(R^{47})_2$, $NHC(O)R^{47}$, $NHC(O)OR^{47}$, $C(O)R^{47}$, $C(O)OR^{47}$, $SR^{47}$, or $SO_2R^{47}$, each of which can be optionally substituted. In one embodiment, both of $R^{42}$ and $R^{43}$ are $C_1$-$C_6$ alkyl. In one further embodiment of this, both of $R^{42}$ and $R^{43}$ are methyl.

In compounds of formula (IV), $R^{44}$ can be H, alkyl, alkenyl, alkynyl, cyclyl, heterocyclyl, aryl, heteroaryl, $C(O)R^{47}$, $C(O)OR^{47}$, $SO_2R^{47}$, each of which can be optionally substituted. In some embodiments, $R^{44}$ is H or $C_1$-$C_6$ alkyl.

When present, each $R^{45}$ is independently halo, alkyl, alkenyl, cyclyl, heterocyclyl, aryl, heteroaryl, $NO_2$, $OR^{47}$, $OC(O)R^{47}$, $OC(O)OR^{47}$, $N(R^{47})_2$, $NHC(O)R^{47}$, $NHC(O)OR^{17}$, $C(O)R^{47}$, $C(O)OR^{47}$, $SR^{47}$, or $SO_2R^{47}$, each of which can be optionally substituted.

Similarly, when present, each $R^{46}$ is independently halo, alkyl, alkenyl, cyclyl, heterocyclyl, aryl, heteroaryl, $NO_2$, $OR^{47}$, $OC(O)R^{47}$, $OC(O)OR^{47}$, $N(R^{47})_2$, $NHC(O)R^{47}$, $NHC(O)OR^{47}$, $C(O)R^{47}$, $C(O)OR^{47}$, $SR^{47}$, or $SO_2R^{47}$, each of which can be optionally substituted. In some embodiments, $R^{46}$ is alkyl or halo. In one embodiment $R^{46}$ is $C_1$-$C_6$ alkyl. In one embodiment, $R^{46}$ is methyl. In one embodiment $R^{46}$ is chloro (Cl).

It is to be understood that when present, $R^{45}$ and $R^{46}$ can be attached to any available position on the ring they are linked to. For example, $R^{45}$ substituent can be attached to position 2, 3, 4 or 5 of the pyrrolidine ring. When more than one of $R^{45}$ is present, they can be located at any combination of 2, 3, 4, and 5 positions of the pyrrolidine ring. Similarly, $R^{46}$ substituent can be attached to position 2, 3, 4, 5, or 6 of the phenyl ring. Again, when more than one of $R^{46}$ is present, they can be located at any combination of 2, 3, 4, 5, and 6 positions of the phenyl group. Additionally, when two or more of $R^{45}$ are present all can be same, all different, or a combination of same and different. Similarly, when two or more of $R^{46}$ are present all can be same, all different, or a combination of same and different.

Variable j can be 0, 1, 2, 3, or 4. In one embodiment, j is 0.

Variable k can be 0, 1, 2, 3, 4, or 5. In some embodiments, k is 2. When k is 2, one $R^{46}$ can be attached to position 2 and the other can be at position 3, 4, 5, or 6 of the phenyl ring; one $R^{46}$ can be at position 3 and the other $R^{46}$ can be at position 4 or 5. In one embodiment, when k is two, one $R^{46}$ is at position 2 and the other is at position 5 of the phenyl ring.

When k is 2 both $R^{46}$ groups can be the same or different. In some embodiment of this, one $R^{46}$ is $C_1$-$C_6$ alkyl and the other is halo. In one embodiment of this, one $R^{46}$ is methyl and the other is Cl.

Substituent $R^{47}$ is independently for each occurrence H, alkyl, alkenyl, alkynyl, cyclyl, heterocyclyl, aryl, or heteroaryl, each of which can be optionally substituted.

In some embodiments, a compound of formula (IV) is of formula (IVa):

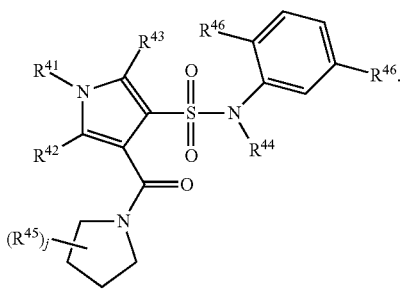

Formula (IVa)

In some further embodiments of this, a compound of formula (Iva) is of formula (IVb):

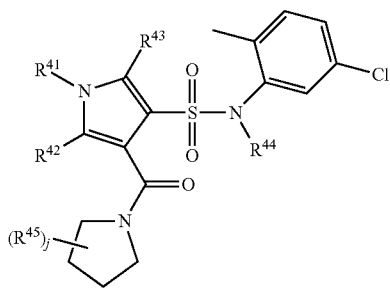

Formula (IVb)

In one embodiment, a compound of formula (IV) is LDN-0130436 as shown in FIG. 7

In one embodiment, a compound of formula (IV) is an analog of LDN-0130436.

In one embodiment, a compound of formula (IV) is LDN-0130436, LDN-0130436B, LDN-0130436C, LDN-0130436D, LDN-0130436E, LDN-0130436F, LDN-0130436G, or LDN-0130436H.

In one embodiment, a compound of formula (IV) is LDN-0130436B.

In one embodiment, a compound of formula (IV) is LDN-0130436C.

In one embodiment, a compound of formula (IV) is LDN-0130436D.

In one embodiment, a compound of formula (IV) is LDN-0130436E.

In one embodiment, a compound of formula (IV) is LDN-0130436F.

In one embodiment, a compound of formula (IV) is LDN-0130436G.

In one embodiment, a compound of formula (IV) is LDN-0130436H.

In one embodiment, a compound of formula (IV) is an isomer of LDN-0130436.

In one embodiment, a compound of formula (IV) is a prodrug of LDN-0130436.

In one embodiment, a compound of formula (IV) is a pharmaceutically acceptable salt of LDN-0130436.

In some embodiments, the compound is of formula (V):

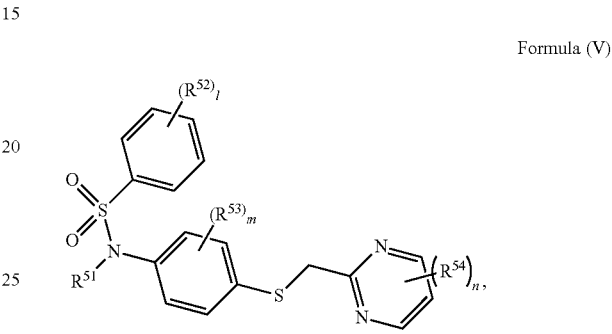

Formula (V)

and analogs, derivatives, isomers, prodrugs, and pharmaceutically acceptable salts thereof.

In one embodiment, the compound is of formula (V). In another embodiment, the compound is an isomer of formula (V). In still another embodiment, the compound is an analog of formula (V). In yet another embodiment, the compound is a prodrug of a compound of formula (V). In another embodiment, the compound is a pharmaceutically acceptable salt of a compound of formula (V).

$R^{51}$ can be H, alkyl, alkenyl, alkynyl, cyclyl, heterocyclyl, aryl, heteroaryl, $C(O)R^{55}$, $C(O)OR^{55}$, $SO_2R^{55}$, each of which can be optionally substituted. In some embodiments, $R^{51}$ is $C_1$-$C_6$ alkyl or H.

When present, each of $R^{52}$, $R^{53}$, and $R^{54}$ is independently halo, alkyl, alkenyl, cyclyl, heterocyclyl, aryl, heteroaryl, $NO_2$, $OR^{55}$, $OC(O)R^{55}$, $OC(O)OR^{55}$, $N(R^{55})_2$, $NHC(O)R^{55}$, $NHC(O)OR^{55}$, $C(O)R^{55}$, $C(O)OR^{55}$, $SR^{55}$, or $SO_2R^5$, each of which can be optionally substituted.

In some embodiments, $R^{52}$ is a $C_1$-$C_6$ alkyl. In one embodiment, $R^{52}$ is t-butyl.

In some embodiments, $R^{54}$ is $OR^{55}$. In one embodiment, $R^{54}$ is $OCH_2CF_3$.

It is to be understood that when present, $R^{52}$, $R^{53}$, and $R^{55}$ can be attached to any available position on the ring they are linked to. When two or more of $R^{52}$ are present all can be same, all different, or a combination of same and different. Similarly, when two or more of $R^{53}$ are present all can be same, all different, or a combination of same and different. Likewise, when two or more of $R^{54}$ are present all can be same, all different, or a combination of same and different.

Variable l can be 0, 1, 2, 3, or 4. In one embodiment, l is 1. In one embodiment, when l is 1, $R^{52}$ is attached at position 4 of the phenyl ring. In one embodiment, l is 1 and $R^{52}$ is t-butyl.

Variable m can be 0, 1, 2, 3, or 4. In one embodiment, m is 0.

Variable n can be 0, 1, 2, or 3. In one embodiment, n is 2. When m is 2, the two $R^{54}$ can be attached to neighboring carbons of the ring. Additionally, when n is 2, both $R^{54}$ groups can be the same or different. In some embodiment, both $R^{54}$ are $OR^{55}$. In one embodiment of $R^{55}$ is an optionally substituted $C_1$-$C_6$ alkyl. In one embodiment, both $R^{54}$ are $OCH_2CF_3$.

Substituent $R^{55}$ is independently for each occurrence H, alkyl, alkenyl, alkynyl, cyclyl, heterocyclyl, aryl, or heteroaryl, each of which can be optionally substituted.

In one embodiment, a compound of formula (V) is LDN-0015257 as shown in FIG. 8.

In one embodiment, a compound of formula (V) is an analog of LDN-0015257.

In one embodiment, a compound of formula (V) is an isomer of LDN-0015257.

In one embodiment, a compound of formula (V) is a prodrug of LDN-0015257.

In one embodiment, a compound of formula (V) is a pharmaceutically acceptable salt of LDN-0015257.

In some embodiments, the compound is of formula (VI):

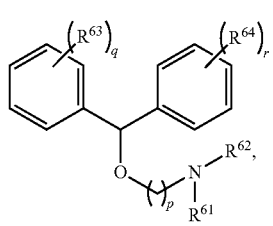

Formula (VI)

and analogs, derivatives, isomers, prodrugs, and pharmaceutically acceptable salts thereof.

In one embodiment, the compound is of formula (VI). In another embodiment, the compound is an isomer of formula (VI). In still another embodiment, the compound is an analog of formula (VI). In yet another embodiment, the compound is a prodrug of a compound of formula (VI). In another embodiment, the compound is a pharmaceutically acceptable salt of a compound of formula (VI).

In compounds of formula (VI), p can be 1, 2, 3, 4, 5, 6, 7, 8, 9, or 10. In one embodiment, p is 4.

$R^{61}$ and $R^{62}$ are independently H, alkyl, alkenyl, alkynyl, cyclyl, heterocyclyl, aryl, heteroaryl, $C(O)R^{65}$, $C(O)OR^{65}$, or $SO_2R^{65}$ each of which can be optionally substituted, or $R^{61}$ and $R^{62}$ together with the nitrogen they are attached to form a 5-8 membered optionally substituted heterocyclyl.

In one embodiment, one of $R^{61}$ and $R^{62}$ is H and the other is an optionally substituted $C_1$-$C_6$ alkyl.

In one embodiment, one of one of $R^{61}$ and $R^{62}$ is H and the other is —$(CH_2)_tN(R^{66})_2$. Each $R^{66}$ is independently H, alkyl, alkenyl, alkynyl, cyclyl, heterocyclyl, aryl, heteroaryl, $C(O)R^{65}$, $C(O)OR^{65}$, or $SO_2R^{65}$ each of which can be optionally substituted. In some embodiments, one $R^{66}$ is H and the other is $C(O)R^{65}$. In some further embodiments of this, one of $R^{66}$ is $C(O)R^{65}$ and $R^{65}$ is an optionally substituted aryl. In one embodiment, the optionally substituted aryl is a substituted phenyl, e.g., 4-fluoro-phenyl, i.e.,

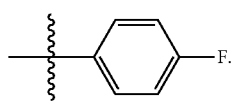

Variable t can 1, 2, 3, 4, 5, 6, 7, 8, 9, or 10. In one embodiment, t is 2.

When present, each of $R^{63}$ and $R^{64}$ is independently halo, alkyl, alkenyl, cyclyl, heterocyclyl, aryl, heteroaryl, $NO_2$, $OR^{65}$, $OC(O)R^{65}$, $OC(O)OR^{65}$, $N(R^{65})_2$, $NHC(O)R^{65}$, $NHC(O)OR^{65}$, $C(O)R^{65}$, $C(O)OR^{65}$, $SR^{65}$, or $SO_2R^{65}$, each of which can be optionally substituted. In some embodiments, both of $R^{63}$ and $R^{64}$ are halo. In one embodiment, both of $R^{63}$ and $R^{64}$ are F.

When present, $R^{63}$ and $R^{64}$ can be attached to any available position on the ring they are linked to. For example, $R^{63}$ and/or $R^{64}$ can be attached to position 2, 3, 4, 5 or 6 of the respective phenyl group they are linked to. In one embodiment, $R^{63}$ and $R^{64}$ are attached to position 4 of the respective phenyl ring.

When two or more of $R^{63}$ are present all can be same, all different, or a combination of same and different. Similarly, when two or more of $R^{64}$ are present all can be same, all different, or a combination of same and different.

When present, $R^{65}$ is independently for each occurrence H, alkyl, alkenyl, alkynyl, cyclyl, heterocyclyl, aryl, or heteroaryl, each of which can be optionally substituted.

Variables q and r are independently 0, 1, 2, 3, 4, or 5. In some embodiments, q is 1. In some embodiments, r is 1. In one embodiment, q and r are both 1. When q and r are both 1, $R^{63}$ and $R^{64}$ can be same or different.

In one embodiment, $R^{61}$ and $R^{62}$ together with the nitrogen they are attached to form an optionally substituted six-membered ring. Accordingly, in some embodiments, a compound of formula (VI) is of formula (VIa):

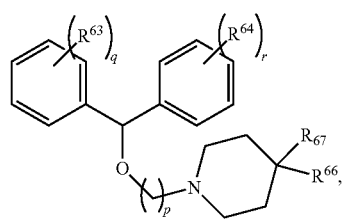

Formula (VIa)

wherein $R^{66}$ is an optionally substituted aryl or heteroaryl, and $R^{67}$ is a H, alkyl, alkenyl, alkynyl, cyclyl, heterocyclyl, aryl, heteroaryl, or $OR^{65}$, each of which can be optionally substituted.

In some embodiments, $R^{66}$ is an optionally substituted phenyl.

In some embodiments, $R^{67}$ is OH or $CH_2NHCH_2C≡CH$.

In one embodiment, $R^{66}$ is an optionally substituted phenyl and $R^{67}$ is OH.

In another embodiment, $R^{66}$ is an optionally substituted phenyl and $R^{67}$ is $CH_2NHCH_2C≡CH$.

Figure 10:
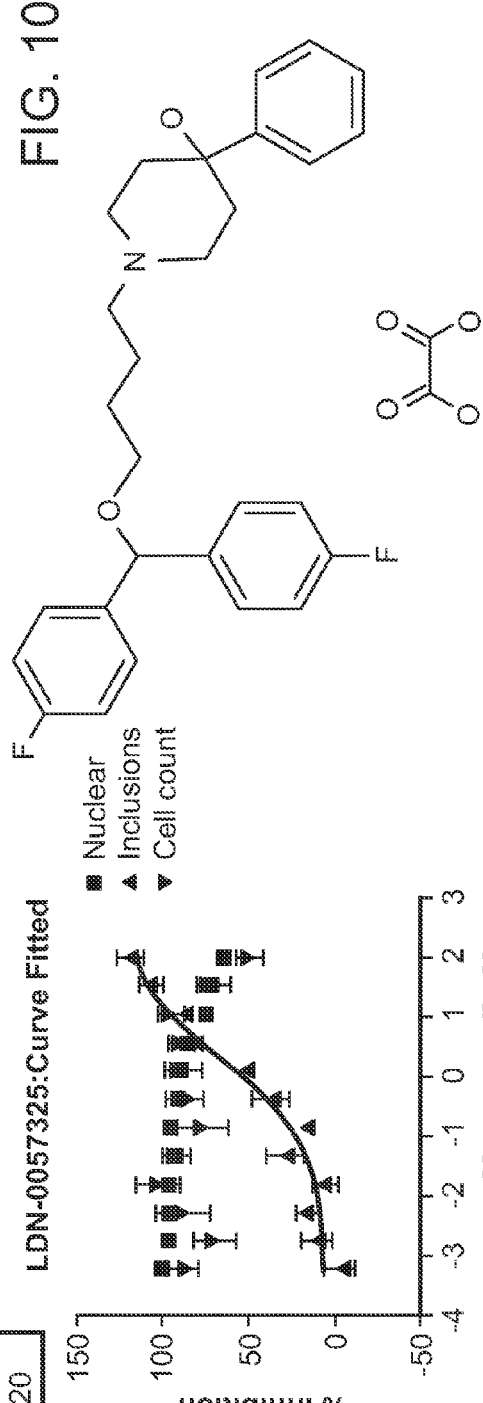
Figure 10:
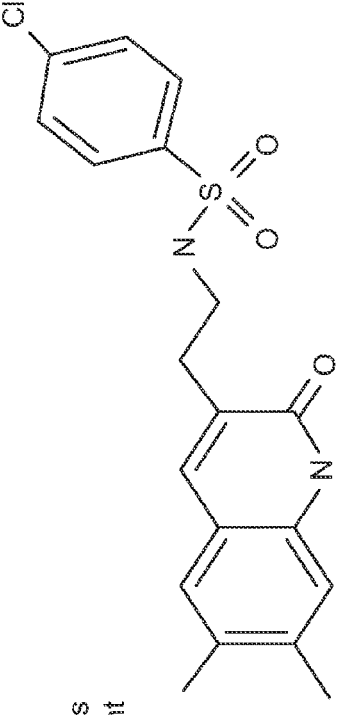
Figure 12:
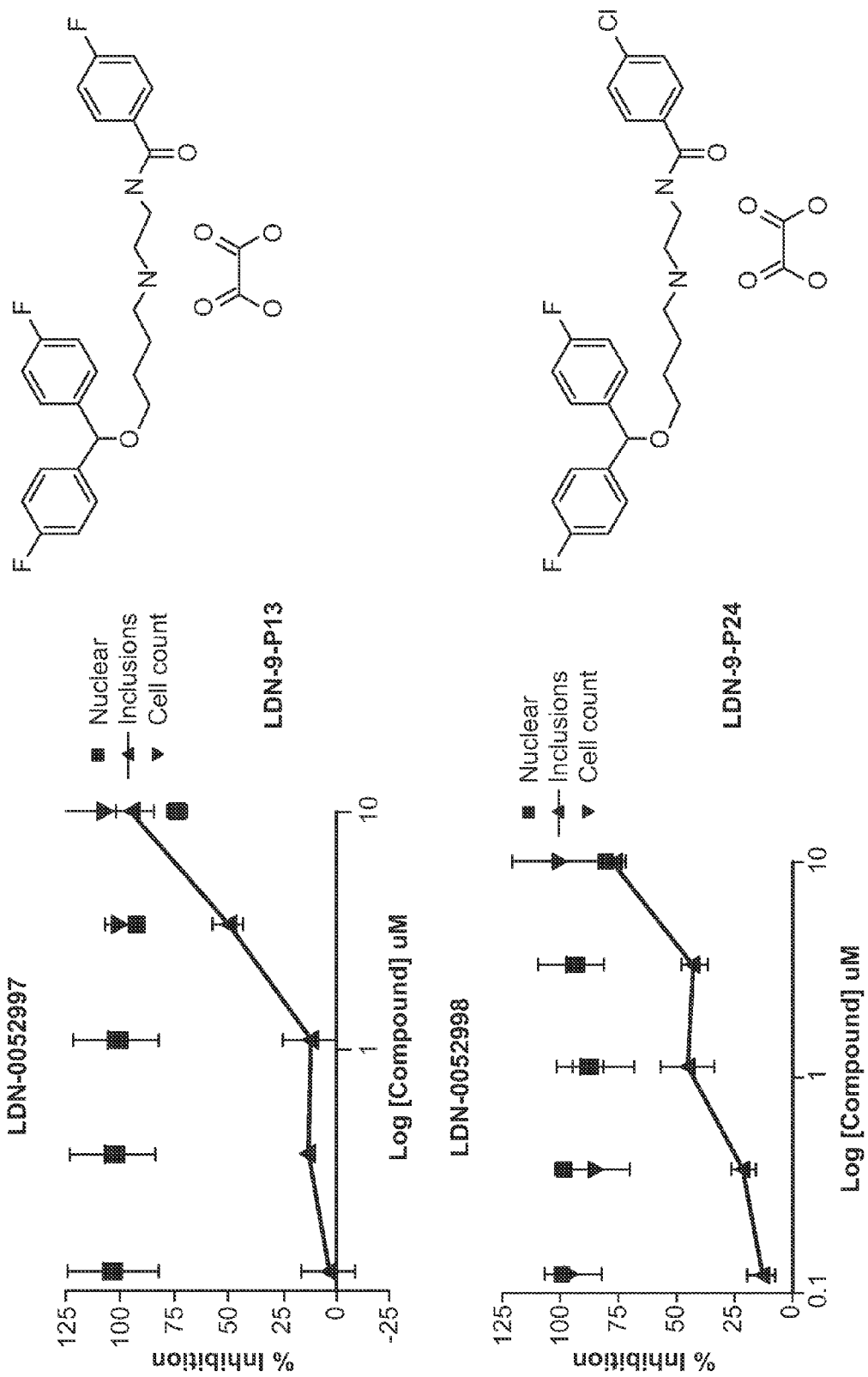
Figure 13A:
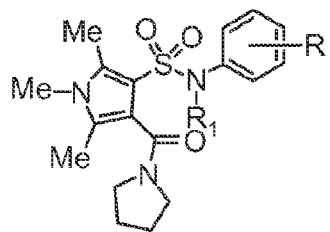
FIG. 13 shows structure activity analysis for derivatives of compound 8. (A) Analogues of compound 8. (B). Dose response curve for compopunds 8 and 8c. (C) Inhibition of inclusion formation in TDP-43::GFP PC12 cells by analogs (3.5 uM)
Figure 13B:
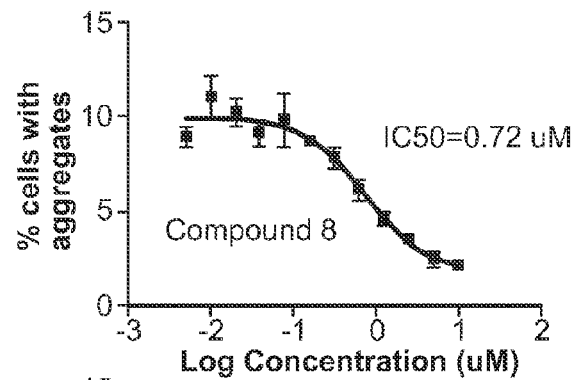
Figure 13B:
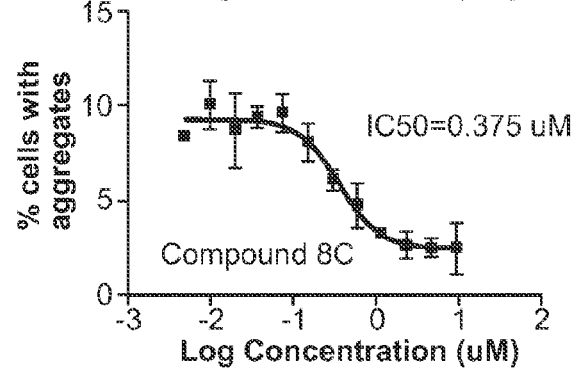
Figure 13C:
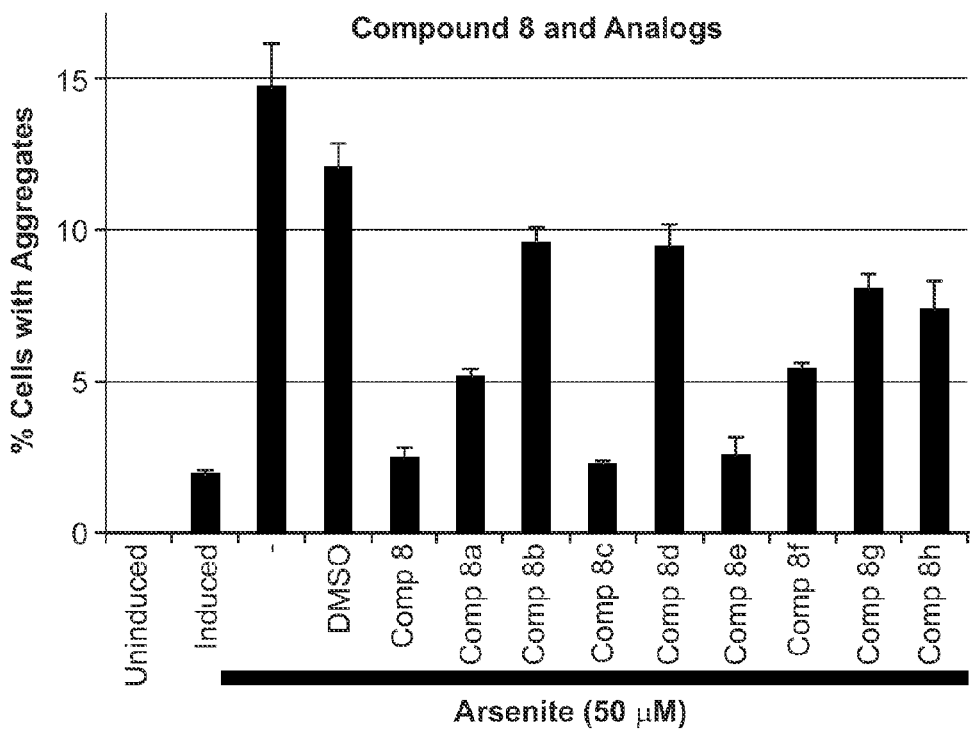

In one embodiment, a compound of formula (VI) is LDN-0052997 (shown in FIG. 12), LDN-0052998 (shown in FIG. 12), LDN-0057218 (shown in FIG. 9), or LDN-0057325 (shown in FIG. 10).

In one embodiment, a compound of formula (VI) is an analog of LDN-0052997, LDN-0052998, LDN-0057218, or LDN-0057325.

In one embodiment, a compound of formula (VI) is an isomer of LDN-0052997, LDN-0052998, LDN-0057218, or LDN-0057325.

In one embodiment, a compound of formula (VI) is a prodrug of LDN-0052997, LDN-0052998, LDN-0057218, or LDN-0057325.

In one embodiment, a compound of formula (VI) is a pharmaceutically acceptable salt of LDN-0052997, LDN-0052998, LDN-0057218, or LDN-0057325.

In some embodiments, the compound is of formula (VII):

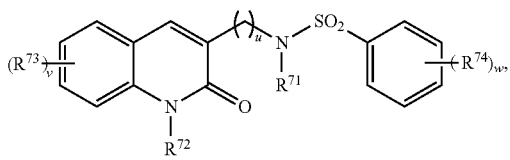

Formula (VII)

and analogs, derivatives, isomers, prodrugs, and pharmaceutically acceptable salts thereof.

In one embodiment, the compound is of formula (VII). In another embodiment, the compound is an isomer of formula (VII). In still another embodiment, the compound is an analog of formula (VII). In yet another embodiment, the compound is a prodrug of a compound of formula (VII). In another embodiment, the compound is a pharmaceutically acceptable salt of a compound of formula (VII).

Variable u in compounds of formula (VII) can be 1, 2, 3, 4, 5, 6, 7, 8, 9, or 10. In one embodiment, u is 2.

In compounds of formula (VII), $R^{71}$ and $R^{72}$ are independently H, alkyl, alkenyl, alkynyl, cyclyl, heterocyclyl, aryl, heteroaryl, $C(O)R^{75}$, $C(O)OR^{75}$, or $SO_2R^{75}$ each of which can be optionally substituted. In one embodiment, both of $R^{71}$ and $R^{72}$ are H.

When present, each $R^{73}$ and $R^{74}$ is independently halo, alkyl, alkenyl, cyclyl, heterocyclyl, aryl, heteroaryl, $NO_2$, $OR^{75}$, $OC(O)R^{75}$, $OC(O)OR^{75}$, $N(R^{75})_2$, $NHC(O)R^{75}$, $NHC(O)OR^{75}$, $C(O)R^{75}$, $C(O)OR^{75}$, $SR^{75}$, or $SO_2R^{75}$, each of which can be optionally substituted. In some embodiments, $R^{73}$ is a $C_1$-$C_6$ alkyl. In one embodiment, $R^{73}$ is methyl. In some embodiments, $R^{74}$ is a halogen. In one embodiment, $R^{74}$ is Cl.

When present, $R^{73}$ and $R^{74}$ can be attached to any available position on the ring they are linked to. For example, $R^{73}$ can be linked to position 4, 5, 6, 7, or 8 of quinolinone to which it is attached. Similarly, $R^{74}$ can be attached to position 2, 3, 4, 5 or 6 of the phenyl to which it is attached. When two or more of $R^{73}$ are present all can be same, all different, or a combination of same and different. Similarly, when two or more of $R^{74}$ are present all can be same, all different, or a combination of same and different.

When present, $R^{75}$ is independently for each occurrence H, alkyl, alkenyl, alkynyl, cyclyl, heterocyclyl, aryl, or heteroaryl, each of which can be optionally substituted.

Variables v and w are independently 0, 1, 2, 3, 4, or 5. In some embodiments, v is 2. In some embodiments, w is 1. In one embodiment, v is 2 and w is 1.

In some embodiments, a compound of formula (VII) is of formula (VIIa):

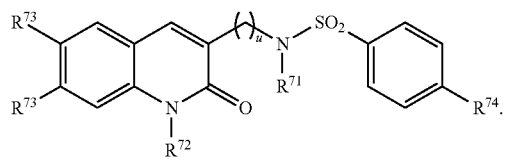

Formula (VIIa)

Figure 11:
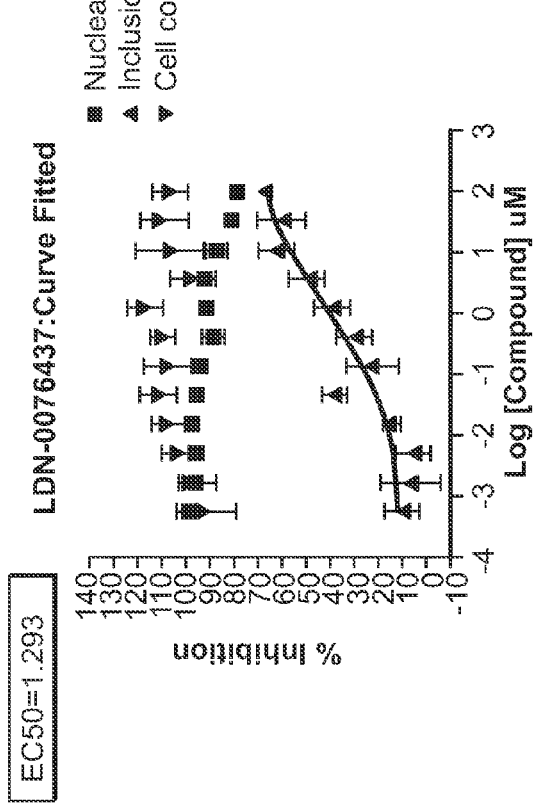

In one embodiment, a compound of formula (VII) is LDN-0076437 shown in FIG. 11.

In one embodiment, a compound of formula (VI) is an analog of LDN-0076437.

In one embodiment, a compound of formula (VI) is an isomer of LDN-0076437.

In one embodiment, a compound of formula (VI) is a prodrug of LDN-0076437.

In one embodiment, a compound of formula (VI) is a pharmaceutically acceptable salt of LDN-0076437.

Exemplary embodiments of compounds of formulas (I)-(VI) may be obtained commercially from ChemDiv (San Diego, Calif.; http://us.chemdiv.com), ChemBridge (San Diego, Calif.; http://www.chembridge.com), and/or Peakdale (Chapel-en-le-Frith, Derbyshire, UK; www.peakdale.co.uk). For example, LDN-0125735 (pdt no. C737-1968), LDN-0130436 (pdt no. G243-0036), LDN-0130436B (pdt no. G243-0026), LDN-0130436C (pdt no. G243-0049), LDN-0130436D (pdt no. G243-0053), LDN-0130436E (pdt no. G243-0093), LDN-0130436F (pdt no. G243-0212), LDN-0130436G (pdt no. G243-0223), LDN-0130436H (pdt no. G243-0064), LDN-0124614 (pdt no. C202-0879), LDN-0125734 (pdt no. C737-1949), and LDN-0076437 (pdt. no. C279-0807) are available from ChemDiv. LDN-0118790 (pdt. no. 51516001), LDN-0118870 (pdt. no. 52164389), LDN-0119629 (pdt. no. 59052230), LDN-0121669 (pdt. no. 81328507), LDN-0196125 (pdt. no. 10570989), LDN-0066337 (pdt. no. 6140545), LDN-0202779 (pdt. no. 40784194), and LDN-0209285 (pdt. no. 94103550) are available from ChemBridge. LDN-0015257 (pdt. no. 3001137) is available from Peakdale.

Other exemplary embodiments of compounds of formulas (I)-(VI) such as LDN-0057218 and LDN-0057325 can be synthesized as discussed in, for example, Choi, et al., *Bioorganic & Medicinal Chemistry* 10 (2002) 4091-4102; herein incorporated by reference in its entirety.

Other exemplary inclusion modulators or inhibitors include mithramycin A, parthenolide and mycophenolic acid.

In some embodiments, the inclusion inhibitor is selected from mithramycin A, parthenolide and mycophenolic acid.

In some embodiments, the inclusion inhibitor is selected from the group consisting of

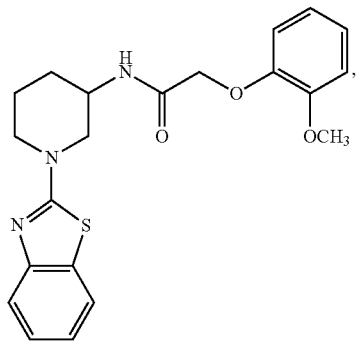

(LDN-0118790)

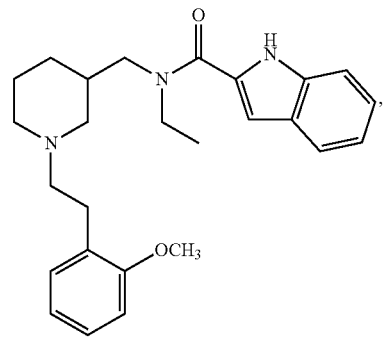

(LDN-0118870)

(LDN-0119629)
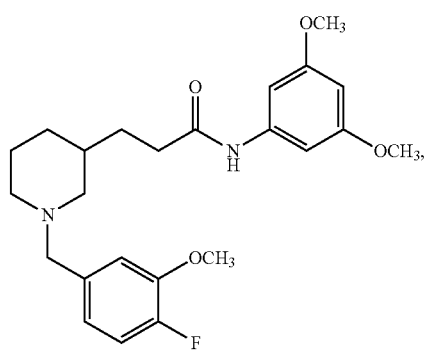
(LDN0121669)
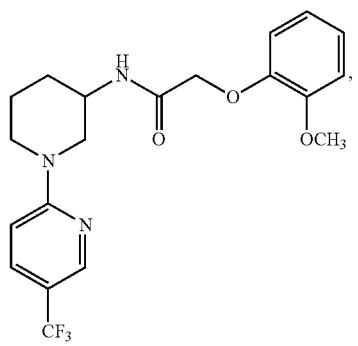
(LDN-0124614)
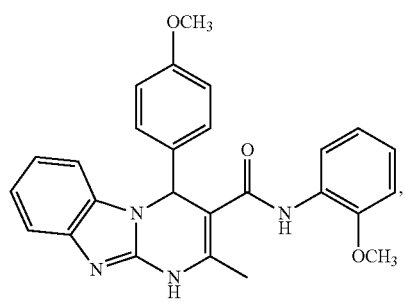
(LDN-0125734)
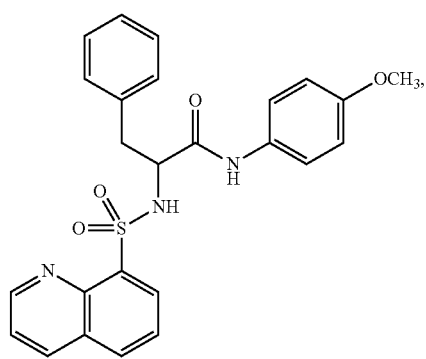
(LDN-0124735)
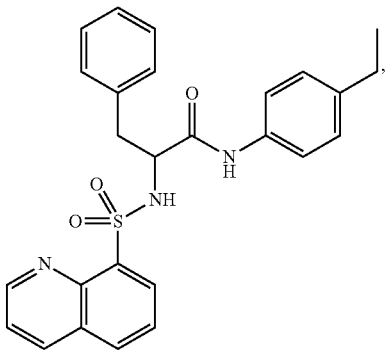
(LDN-0130436)
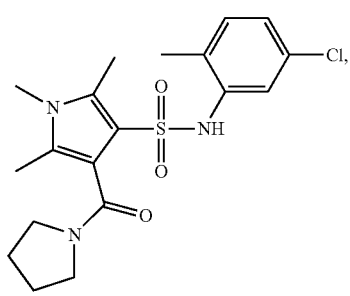
(LDN-00130436B)
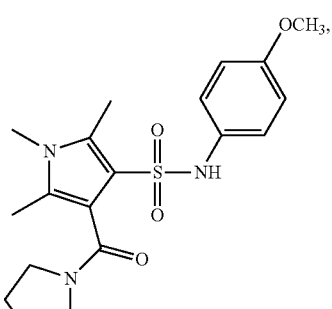
(LDN-0130436C)
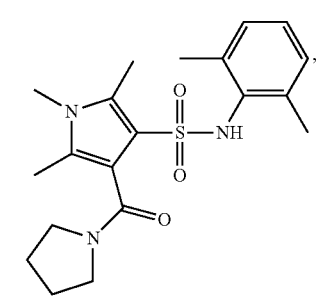
(LDN-0130436D)

-continued
(LDN-0130436E)
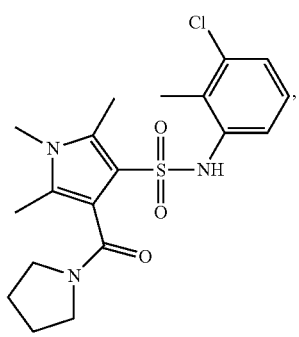
(LDN-0015257)
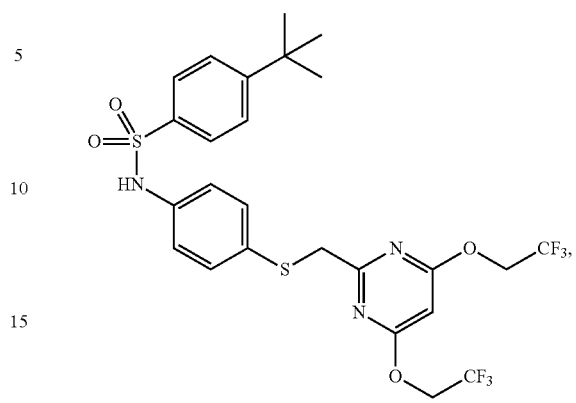
(LDN-0130436F)
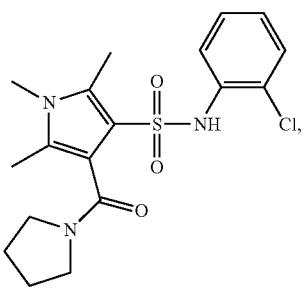
(LDN-0057218)
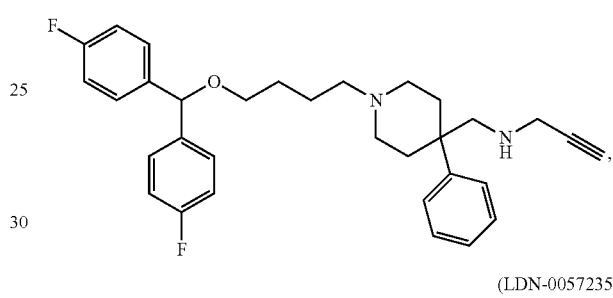
(LDN-0057235)
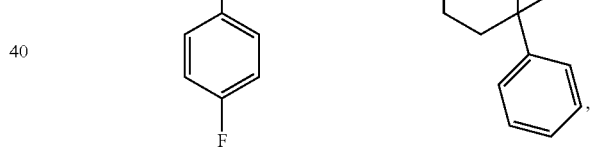
(LDN-0130436G)
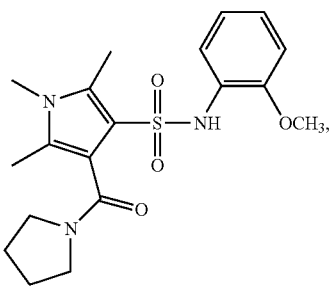
(LDN-0066337)
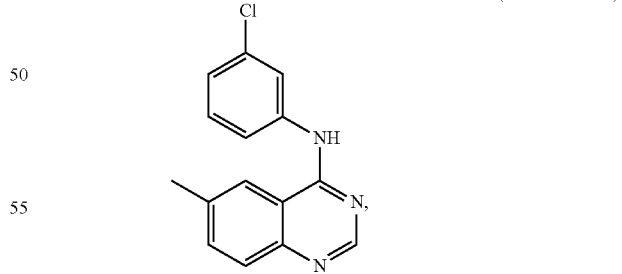
(LDN-0130436H)
(LDN-0076437)
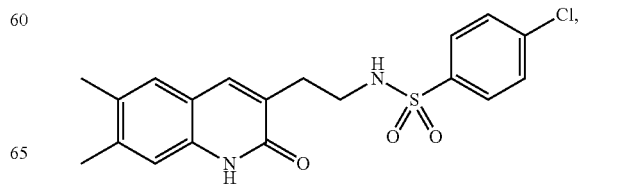

-continued
(LDN-0202779)
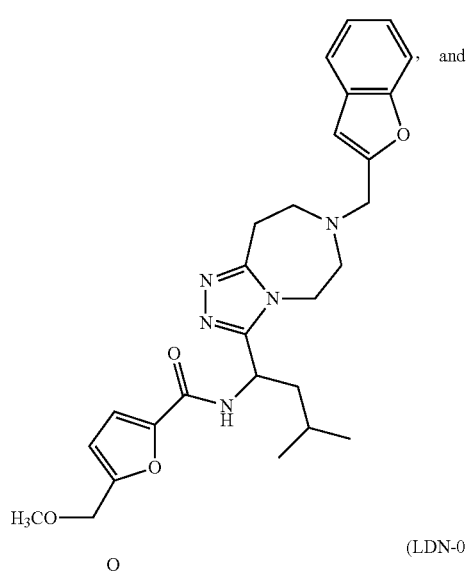
, and
or a pharmaceutically acceptable salt thereof.
In some embodiments, the inclusion inhibitor is selected from the group consisting of
(LDN-0209285)
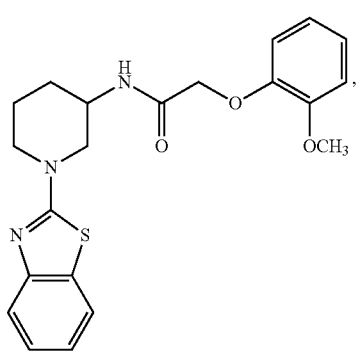
(LDN-0118790)
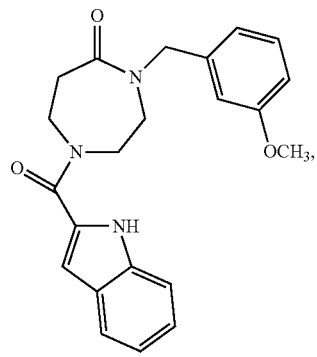
(LDN-0121669)
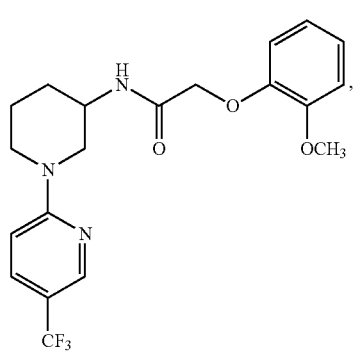
-continued
(LDN-0124614)
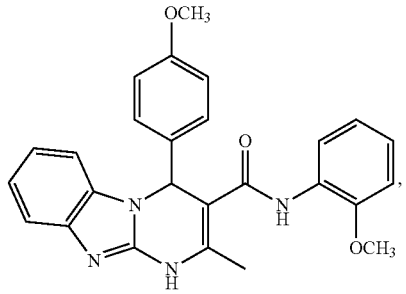
(LDN-0125734)
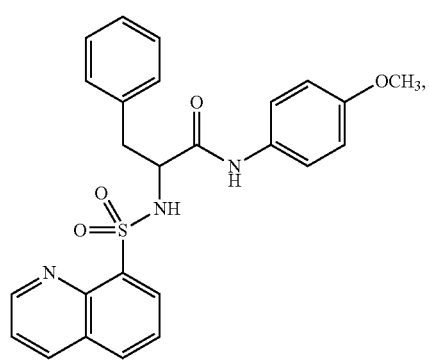
(LDN-0125735)
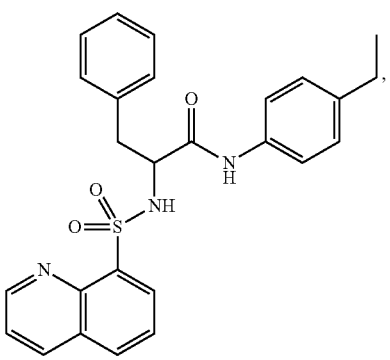
(LDN-0130436)
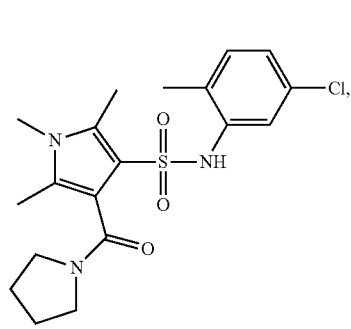

-continued

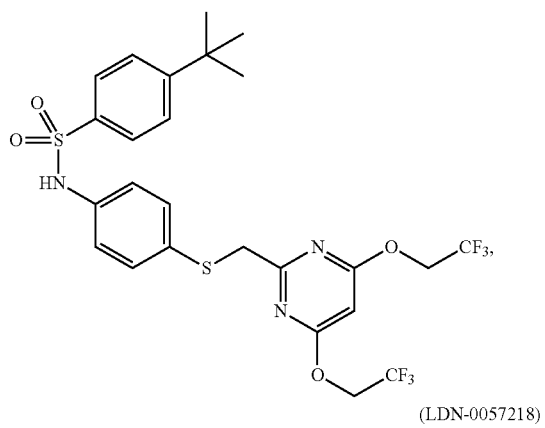
(LDN-0015257)

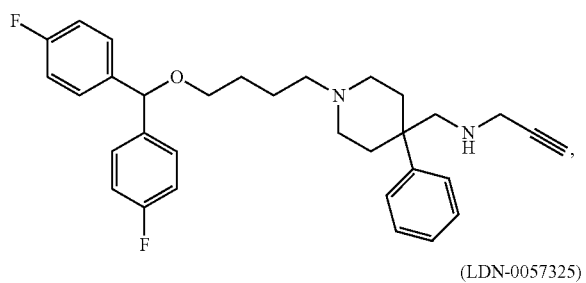
(LDN-0057218)

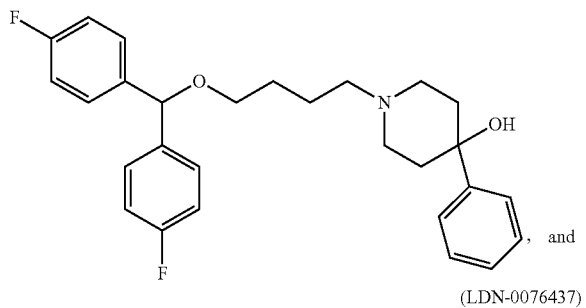
(LDN-0057325)

, and (LDN-0076437)

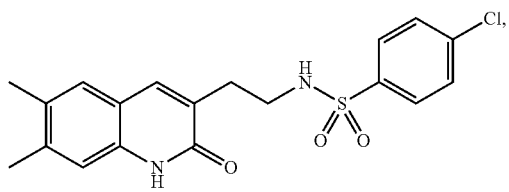

or a pharmaceutically acceptable salt thereof.

Pharmaceutical Compositions

For administration to a subject, the compounds of the invention can be provided in pharmaceutically acceptable compositions. These pharmaceutically acceptable compositions comprise a therapeutically-effective amount of one or more of the compounds described above, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, each of which are herein incorporated by reference in its entirety.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. For example, an amount of a compound administered to a subject that is sufficient to produce a statistically significant, measurable change in at least one symptom of inflammation.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the compositions are administered by intravenous infusion or injection.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, at least one symptom of a disease or disorder is alleviated by at least 5%, at least 10%, at least 20%, at least 30%, at least 40%, or at least 50%.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with neurodegenerative disease or disorder, cancer, or viral infections.

In addition, the methods described herein can be used to treat domesticated animals and/or pets. A subject can be male or female. A subject can be one who has been previously diagnosed with or identified as suffering from or having a neurodegenerative disease or disorder, a disease or disorder associated with cancer, a disease or disorder associated with viral infection, or one or more complications related to such diseases or disorders but need not have already undergone treatment.

The compound can be administrated to a subject in combination with a pharmaceutically active agent. Exemplary pharmaceutically active compound include, but are not limited to, those found in *Harrison's Principles of Internal Medicine*, 13$^{th}$ Edition, Eds. T. R. Harrison et al. McGraw-Hill N. Y., NY; Physicians Desk Reference, 50$^{th}$ Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, each of which are herein incorporated by reference in its entirety. In some embodiments, pharmaceutically active agent include those agents known in the art for treatment of cancer, inflammation or inflammation associated disorders, or infections.

The compound and the pharmaceutically active agent can be administrated to the subject in the same pharmaceutical composition or in different pharmaceutical compositions (at the same time or at different times). When administrated at different times, the compound and the pharmaceutically active agent can be administered within 5 minutes, 10 minutes, 20 minutes, 60 minutes, 2 hours, 3 hours, 4, hours, 8 hours, 12 hours, 24 hours of administration of the other When the inhibitor and the pharmaceutically active agent are administered in different pharmaceutical compositions, routes of administration can be different.

The amount of compound that can be combined with a carrier material to produce a single dosage form will generally be that amount of the inhibitor that produces a therapeutic effect. Generally out of one hundred percent, this amount will range from about 0.1% to 99% of inhibitor, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that inflammasome inhibitor is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "halogen" refers to any radical of fluorine, chlorine, bromine or iodine.

The term "acyl" refers to an alkylcarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, $(C_1-C_6)$alkanoyl (e.g., formyl, acetyl, propionyl, butyryl, valeryl, caproyl, t-butylacetyl, etc.), $(C_3-C_6)$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions.

The term "alkyl" refers to saturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1-C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "alkoxy" refers to an —O-alkyl radical.

The term "aminoalkyl" refers to an alkyl substituted with an amino.

The term "mercapto" refers to an —SH radical.

The term "thioalkoxy" refers to an —S-alkyl radical.

The term "aryl" refers to monocyclic, bicyclic, or tricyclic aromatic ring system wherein 0, 1, 2, 3, or 4 atoms of each ring may be substituted by a substituent. Examplary aryl groups include, but are not limited to, phenyl, naphthyl, anthracenyl, azulenyl, fluorenyl, indanyl, indenyl, naphthyl, phenyl, tetrahydronaphthyl, and the like.

The term "arylalkyl" refers to alkyl substituted with an aryl.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heteroarylalkyl" refers to an alkyl substituted with a heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examplary heterocyclyl groups include, but are not limited to piperazinyl, pyrrolidinyl, dioxanyl, morpholinyl, tetrahydrofuranyl, and the like.

The term "haloalkyl" refers to an alkyl group having one, two, three or more halogen atoms attached thereto. Exemplary haloalkyl groups incude, but are not limited to chloromethyl, bromoethyl, trifluoromethyl, and the like.

The term "optionally substituted" means that the specified group or moiety, such as an alkyl group, alkenyl group, alkynyl group, cyclyl group, heterocyclyl group, aryl group, heteroaryl group and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, or heteroaryl group at any atom of that group. Suitable substituents include, without limitation, halo, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, aryloxy, cyano or ureido. In some cases, two substituents, together with the carbons to which they are attached to can form a ring.

In many cases, protecting groups are used during preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative protecting groups, are disclosed in Greene and Wuts, *Protective Groups in Organic Synthesis*, Chapter 2, 2d ed., John Wiley & Sons, New York, 199; herein incorporated by reference in its entirety. Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Exemplary amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R and S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+) and (−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction $F_{(+)}$ and $F_{(-)}$ (where the sum of $F_{(+)}$ and $F_{(-)}=1$). The enantiomeric excess is defined as $*F_{(+)}-F_{(-)}*$ and the percent enantiomeric excess by $100\times*F_{(+)}-F_{(-)}*$. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A nonselective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

The term "analog" as used herein refers to a compound that results from substitution, replacement or deletion of various organic groups or hydrogen atoms from a parent compound. As such, some monoterpenoids can be considered to be analogs of monoterpenes, or in some cases, analogs of other monoterpenoids, including derivatives of monoterpenes. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenyloin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Prodrug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), each herein incorporated by reference in its entirety.

As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

TDP-43 is the principle component of inclusions in amyotrophic lateral sclerosis (ALS) and in some frontotemporal dementia (FTLD-U). TDP-43 is a nuclear RNA binding protein, which translocates to the cytoplasm during stress where it forms cytoplasmic granules. Our results indicate that these cytoplasmic TDP-43 inclusions co-localize with RNA granules termed "stress granules" (SGs), both in cells and in human ALS spinal cord, and TDP-43 inclusions can be reversed by chemicals that reverse SGs (*PLoS ONE*, October 2010 5(10), e13250; herein incorporated by reference in its entirety). Under many conditions (e.g., arsenite treatment, nutrient deprivation) co-localization with SGs approaches 100%. Disease-linked mutations in TDP-43 increase cytoplasmic inclusion formation. This linkage to SGs appears to generalize to other ALS-linked genes because FUS, ataxin-2 and SMN all are associated with ALS or motor neuron diseases, also translocate to the cytoplasm, also form inclusions co-localized with SGs, and (for FUS & ataxin-2) also form complexes associated with TDP-43 (*Nature*, 2010, 466, 1069-75; *Proc Natl Acad Sci USA*, 2010, 107, 13318-23; each herein incorporated by reference in its entirety). These data point to a strong biological connection between SGs and TDP-43. Discovery of the association between TDP-43 and SGs paves the way for novel insights into TDP-43 biology, and also suggests mechanisms by which mutations in TDP-43 cause disease. Accordingly, SG biology stimulates formation of TDP-43 inclusions, and that pathogenic factors linked to ALS increase TDP-43 inclusion formation through a process mediated by SG pathways.

ALS is a devastating, rapidly fatal neurodegenerative disease that strikes people, and currently has no disease modifying treatments. Discovery of the putative association between TDP-43 and SG biology links TDP-43 to a biological pathway whose biology is profoundly important to neuronal function, and that offers many potential targets for pharmacological intervention. A striking number of proteins linked to ALS are RNA binding proteins, and most of these participate in SG biology. Thus, understanding the role of SG biology in the pathophysiology of TDP-43 will likely provide insights into the pathophysiology of other proteins linked to ALS, including FUS, ataxin-2 and VCP. SG biology is also fundamentally interesting because it is one of the rare examples of a normal physiological process that is based on reversible aggregation of proteins; one aspect of this story that is fascinating is the large number of SG proteins that share homology to yeast prion proteins, which raises the possibility that understanding SG biology will also help to illuminate the biology of diseases resulting from prion proteins. The reversible nature of SG-based aggregation offers a biological pathway that can be applied to reverse the pathology and toxicity associated with TDP-43 inclusion formation. Preliminary results by the authors already demonstrate that chemicals that reverse SG formation also reverse formation of TDP-43 inclusions. These chemicals though are quite toxic (they inhibit protein translation), but the SG pathway offers many other targets able to reverse SG biology that are not toxic to the cell. Investigating the particular elements of the SG pathway that regulate TDP-43 inclusion formation can identify selective approaches for therapeutic intervention to delay or halt the progression of ALS.

Results presented herein demonstrate, for the first time, that TDP-43 pathology in the human CNS is associated with SG markers. Regulation of protein translation is clearly critical for healthy brain functioning, and SG biology plays a fundamental role in this regulatory axis.

TDP-43:

TDP-43 is also known as Tar DNA binding protein (TAR-DBP). TDP-43 is a major protein component of inclusions in ALS and FTLD-U (*Science*, 2006, 314, 130-3; herein incorporated by reference in its entirety). TDP-43 is a 414 amino acid nuclear protein encoded by the TARDBP gene on chromosome 1. It is ubiquitously expressed in all tissues (*J Biol Chem*, 2001, 276, 36337-43; herein incorporated by reference in its entirety). It contains two RNA recognition motifs and a glycine rich domain at the C-terminus. Nuclear functions associated with TDP-43 include acting as a transcriptional repressor (such as for the SP-10 gene), contributing to exon skipping (as shown for the cystic fibrosis transmembrane conductance regulator gene), and acting as a scaffold protein for nuclear bodies in concert with survival motor neuron protein (SMN) (*J Biol Chem*, 2005, 280, 37572-84; *J Biol Chem*, 2007, 282, 36143-54; *Proc Natl Acad Sci USA*, 2002, 99, 13583-8; each herein incorporated by reference in its entirety). Interestingly, many other proteins associated with ALS or motor neuron diseases are also RNA binding proteins, including FUS, SMN, ataxin-2, VCP. This suggests a systematic connection between RNA binding proteins and motor neuron diseases.

Mutations in TDP-43 are increasingly associated with disease. Two papers initially identified different point mutations in TDP-43 (A315T, M337V) that are associated with ALS, and multiple papers have expanded upon these findings to identify other mutations associated with sporadic and familial ALS (*Science*, 2008, 319, 1668-72; *Ann Neurol*. 2008, 63(4), 535-538; each herein incorporated by reference in its entirety). Association of mutations with ALS indicates that abnormalities in TDP-43 are sufficient to cause disease. Increasingly, studies suggest a link between TDP-43 and cell death. Acute expression of TDP-43 in chick spinal cord elicits apoptosis in neurons (*Science*, 2008, 319, 1668-72; herein incorporated by reference in its entirety). Transgenic models of TDP-43 (WT or mutant) in mouse, *Drosophila* and *C. elegans* all show evidence of neurodegeneration (*J Neurosci*, 2010, 30, 10851-9; *Proc Natl Acad Sci USA*, 2010, 107, 3858-63; *J Exp Med*, 2010, 207, 1661-73; *Neurobiol Dis*. 2010, 40(2), 404-414; *Neuroscience*, 2010, 167, 774-85; *Proc Natl Acad Sci USA*, 2009, 106, 18809-14; *J Biol Chem*, 2010, 285, 11068-72; *Proc Natl Acad Sci USA*. 2010, 107, 7, 3169-74; and *Hum Mol Genet*, 2010, 19 (16): 3206-3218; each herein incorporated by reference in its entirety). The mechanisms of toxicity are unknown but cleavage is associated with TDP-43 pathology. Brains from subjects with ALS and FTD show smaller bands at 25 KD and 35 KD that appear to be cleavage products containing the carboxy domain of TDP-43 (*Science*, 314, 130-3; herein incorporated by reference in its entirety). TDP-43 can be cleaved by caspases in vitro, and forms cytoplasmic inclusions in response to apoptotic stimuli (*J Neurosci*, 2007, 27, 10530-4; herein incorporated by reference in its entirety).

A recent publication by co-authored by the inventors describes the relationship between TDP-43 and SGs (*PLoS ONE*, October 2010 5(10), e13250; herein incorporated by reference in its entirety); George Murphy has published on a novel system for the efficient production of clinically relevant, transgene-free human iPSCs (*Stem Cells*. 2010, 28 (10), 1728-1740; herein incorporated by reference in its entirety). Leonard Petrucelli has published on transgenic mice expressing WT TDP-43 (*J Neurosci*, 2010, 30, 10851-9; herein incorporated by reference in its entirety).

RNA Binding Proteins:

mRNA binding proteins facilitate mRNA trafficking from the nucleus to the cytoplasm as part of the biological machinery that regulates mRNA metabolism, such as RNA decay and protein translation. RNA decay is a constitutive process that occurs in cytoplasmic compartments termed processing bodies (P-bodies). However, under stressful conditions mRNA binding proteins consolidate mRNA in cytoplasmic compartments, termed the stress granules (SGs); this recruitment is mediated by multiple proteins, including T-cell intracellular antigen 1 (TIA-1), RasGAP-associated endoribnuclease (G3BP), elongation initiation factor 3 (eIF3) and poly-A binding protein (PABP) (*Trends Biochem Sci*, 2008, 33, 141-50; herein incorporated by reference in its entirety). SGs function in part to triage RNA and sequester transcripts not needed for coping with the stress (*Trends Biochem Sci*, 2008, 33, 141-50; herein incorporated by reference in its entirety). The mechanism of SG formation is striking because it results from the regulated, reversible aggregation process of mRNA binding proteins with prion-like domains, such as TIA-1, TIAR and G3BP (*Mol Biol Cell,* 2004, 15, 5383-98; herein incorporated by reference in its entirety).

It will recognized that one or more features of any embodiments disclosed herein may be combined and/or rearranged within the scope of the invention to produce further embodiments that are also within the scope of the invention.

Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Establishing the PC12-TDP-43 Model. Generation of TDP-43:: GFP Inducible PC12 Cell Lines:

We generated a Tet-Off inducible PC12 cell line (Clontech; the parent line stably expresses high levels of the Tetracycline binding protein) that is stably transfected with a WT TDP-43::GFP (where the GFP is at the C-terminus). Newly induced TDP-43::GFP (24 hrs) is initially observable with a diffuse nuclear localization; after 72 hrs of expression, cytoplasmic and nuclear aggregates of TDP-43 become readily apparent (FIG. 1, arrows). The expression of TDP-43 in this line appears to occur in a fraction of the cells but we believe this is due to auto-regulation because expression of TDP-43:: GFP can be induced in all of the cells by some of the compounds we have identified. Treatment with arsenite (50 µM, 18 hrs) increased the rate (>80 of cells) and consistency of inclusion formation. The high-throughput screen used the arsenite (50 µM, 18 hrs) treatment protocol, where arsenite was added 1 hr after the test compounds.

Preliminary Screens to Identify Inhibitors of TDP-43 Inclusion Formation:

We carried out the high-throughput screen in collaboration with the Laboratory for Drug Discovery in Neurodegeneration (LDDN), which is an integral part of the Harvard NeuroDiscovery Center (HNDC) (www.neuridiscovery.harvard-.edu). LDDN has a permanent staff of industry-seasoned scientists with specialties in assay development, laboratory automation, informatics, and medicinal chemistry. The LDDN has a compound library of 75,000 compounds selected with a series of filters for "drug-like" properties including the physical properties that predict their likelihood to cross the blood brain barrier. LDDN has completed over fifty high throughput screens. We used the automated GE IN Cell Analyzer 1000 microscope system for high throughput analyses. Test chemicals were added to the cells 48 hrs after induction of TDP-43 (by removal of doxycycline). After another 24 hrs, the cells were fixed and double-stained with DAPI (to detect nuclei). Inclusions present in a collar around the nucleus but not fully co-localized with the DAPI stain (FIG. 1) were identified by the IN-Cell analyzer as inclusions. The computer counted the number of cells (based on DAPI-positive nuclei), TDP-43 levels and inclusions per field. The counts from 6 different fields within a well were averaged to develop a measure of the mean number of inclusions per field. This was repeated for every well in a 384 well plate and every plate in the library. We screened a 1600 compound library of FDA approved chemicals, known bioactives, and purified natural products, and an additional 75,000 chemicals from the general compound library (the libraries are described in the Resources section). Sixteen out of the 75,000 compounds were also selected as leads because they reduced TDP-43 inclusions by more than three standard deviations beyond the mean, showed <20% toxicity (based on counting total cell numbers), repeated on subsequent evaluations using fresh powder compound stocks and showed a dose dependent concentration curve for inhibition of TDP-43 aggregation using both 5 point and 12 point dose response curves (FIGS. 2-12). We also identified additional compounds from the library of FDA/bioactive chemicals. Representative EC50 values are shown in Table 1. Additional representative compounds are shown in FIG. 13. The compounds identified represented several different structural classes, are generally Lipinski rule compliant, and have no known toxicophores or reactive groups.

TABLE 1

Inhibition of TDP-43 Inclusion Formation.

| Cmpd No. | Code No. | EC50 (nM) |
|---|---|---|
| 1 | LDN-0118790 | 38 |
| 2 | LDN-0118870 | 74 |
| 3 | LDN-0119629 | 39 |
| 4 | LDN-0121669 | 98 |
| 5 | LDN-0124614 | 306 |
| 6 | LDN-0125734 | 15 |
| 7 | LDN-0125735 | 139 |
| 8 | LDN-0130436 | 174 |
| 9 | LDN-0196125 | <1 |
| 2-1 | LDN-0015257 | 152 |
| 2-2 | LDN-0057218 | 290 |
| 2-3 | LDN-0057325 | 1920 |
| 2-4 | LDN-0066337 | 10 |
| 2-5 | LDN-0076437 | 1290 |
| 2-7 | LDN-0202779 | 11 |
| 2-8 | LDN-0209285 | 180 |
| Mithramycin A | LDN-0052881 | 2000 |
| Parthenolide | LDN-0014143 | 3000 |
| Mycophenolic acid | LDN-0014149 | 1500 |

Figure 14:
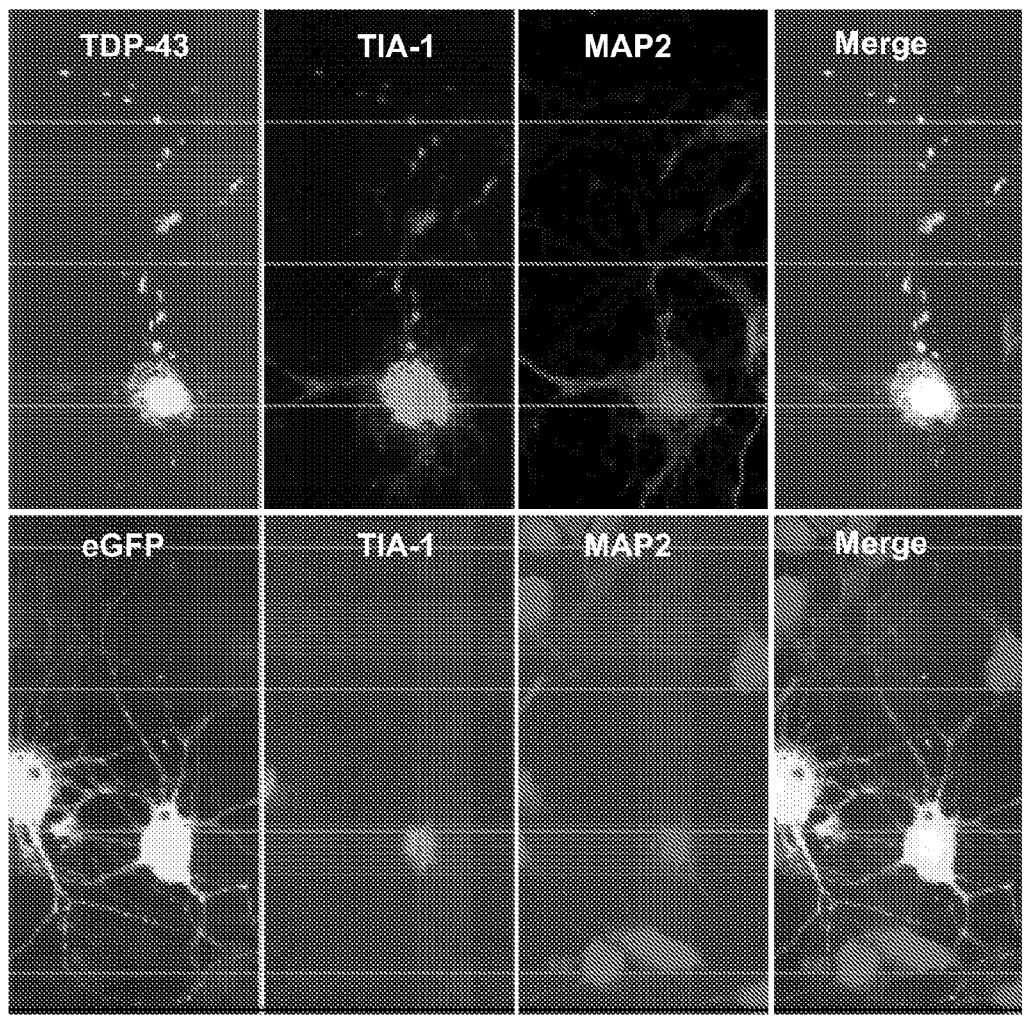
FIG. 14 shows inclusion formation in primary neurons (DVI6) over-expressing TDP-43 (green) and TIA (red). Map2 reactivity is endogenous.

Expressing TDP-43 in Primary Neurons Leads to Inclusion Formation:

An important element of a drug screening is to examine toxicity and inclusion formation in the primary neuronal cells grown in culture, which is based on the results of multiple groups studying primary neurons grown in culture (PLoS One, 2010. 5: e15878; herein incorporated by reference in its entirety). Initial results of examining expression of TDP-43 in primary neuronal cultures show that TDP-43 readily forms inclusions (FIG. 14), and that the process of inclusion formation and toxicity is enhanced by arsenite (50 uM, 18 hrs), much like in our high-throughput screen, and by others (*PLoS ONE,* October 2010 5(10), e13250; J Neurosci, 2010. 30: 639-49; each herein incorporated by reference in its entirety). The field of stress granules (SG) classically used an acute arsenite treatment of 0.5 mM for 30-60 min. While this procedure works in PC12 cells (and in induced pluripotent stem cells), the inventors have also taken care to modify the treatment to enable the screening and analysis of the drugs. Thus, a treatment of 15-50 uM for a much longer time (18-24 hrs) to induce the SGs and TDP-43 inclusions turns out to be important when looking in hippocampal neurons grown in culture (the inventors have used down to 7 uM) and induced pluripotent stem cells. TDP-43 inclusion induction has also been analyzed in iPSPs, and they can be induced well by puromycin. This shows improvements over $H_2O_2$ and wortmannin.

Accordingly, one can readily quantify toxicity using analyses of neurite length, arborization and cell size, using approaches similar to Przedborsky and colleagues (Nat Neurosci, 2007, 10: 615-22; herein incorporated by reference in its entirety).

Accordingly, the invention provides a novel neuronal cell line that inducibly expresses WT TDP-43 and develops spontaneous inclusions, which provides a novel approach for high throughput screening of inhibitors of TDP-43 cytoplasmic inclusions. The inducible nature of the screening obviates potential toxicity that is commonly observed with stable over-expression of TDP-43.

Additionally, the data presented herein indicates that that TDP-43 inclusions form in conjunction with the SG pathway, and that inhibitors of SG formation can also inhibit TDP-43 inclusion formation (*PLoS ONE*, October 2010 5(10), e13250; herein incorporated by reference in its entirety). Accordingly, a compound identified by the screening method described herein can be used to interrogate the role of TDP-43 in SG formation and the role of SG formation in the pathophysiology of ALS and frontotemporal dementia (FTD).

Determination of Effect of Compounds on Formation of TDP-43 Inclusions:

Primary cultures of cortical and motor neurons, transduced the neurons with TDP-43 (WT, A315T or A343T) are generated and the viability and inclusion formation during exposure to each of the lead compounds is followed. In one example, cortical and motor neurons are examined because TDP-43 forms inclusions in cortical neurons (frontotemporal dementia) and in motor neurons (ALS). Cortical neurons: Rat embryos are harvested at E18 and placed in cell culture. At DIV 3, the cells were transduced with lentivirus TDP-43 (WT, A315T or A343T) using a multiplicity of infection of 5. Motor neurons: We use the mouse ChAT::GFP line that selectively expresses GFP in cholinergic neurons; a colony of these mice is currently available at Boston University in the laboratory of Krzystof Blusztajn (Nat. Protoc, 2008. 3: 34-40; herein incorporated by reference in its entirety). Mouse fetuses are harvested at E12.5 as described previously, and sorted by FACS as described by Dr. Blusztajn's group (Nat. Protoc, 2008. 3: 34-40; Nat Neurosci, 2007. 10: 615-22; each herein incorporated by reference in its entirety). CNS tissue are dissociated and GFP positive neurons are isolated by FACS. The GFP-positive neurons are placed in culture. Neuronal identity will be ascertained by complementing the GFP fluorescence with staining for MAP2, as described by Nagai, et al (Nat Neurosci, 2007. 10: 615-22; herein incorporated by reference in its entirety). At day 3 in vitro (DIV3), the neurons are transduced with lentivirus TDP-43 (WT, A315T or A343T) using a multiplicity of infection of 5.

Treatment:

The test compounds are added to the cultures 24 hrs after viral transduction (DIV4), and maintained throughout the treatment period; fresh compound in new medium is added every 2 days. The neurons are imaged at DIVE to measure outcomes under basal conditions. On DIV7, arsenite (50 µM, 18 hrs) is added, and then the neurons are imaged after 18 hrs and the outcomes quantified. For each lead compound generate an 8 point dose response curve is generated, using a range corresponding to 2 log units above and below the $IC_{50}$ for each compound (determined based on the studies in PC12 cells); generally this corresponds to a range of 10 nM to 10 µM. Fresh compound is be added every third day until termination of the assay by replacing 50% of the medium with medium containing fresh compounds. Toxicity and inclusion formation is followed as described below.

Toxicity:

Neurotoxicity/neurodegeneration is followed using protocols similar to those described by Przedborsky and colleagues (Nat Neurosci, 2007. 10: 615-22; herein incorporated by reference in its entirety). At days 1, 3 and 7 after infection toxicity is quantified. The number of neurons, size of the cell bodies, process length (determined by counting the number of processes >700 µm), and analysis by the neurite tracer plugin for the image J application (J Neurosci Methods, 2008. 168: 134-9; herein incorporated by reference in its entirety). For cortical neurons, toxicity of each condition is analyzed by LDH assay normalized to protein content at the end of the assay.

Inclusion Formation Assay:

Cortical and motor neurons transduced with TDP-43 spontaneously develop inclusions after treatment with 50 µM arsenite, 18 hr. At T=24 hrs test compounds are added (dose=Ki) ±0.5 mM arsenite (1 hr), where Ki refers to 50% inhibition of inclusion formation from the PC12 primary screen assay. At days 1, 3 and 7 the cells are fixed and inclusion formation quantified using the IN Cell analyzer.

Analysis of Endogenous TDP-43:

The effect of compounds on inclusion formation in neurons that do not over-express TDP-43 to mimic the environment of the brain normally can be examined as follows. Cortical and motor neurons are grown in culture. At DIV 7, the neurons are treated with the test compounds (dose=1 & $10 \times IC_{50}$)±0.5 mM arsenite (1 hr) as described in the "Inclusion Formation Assay" above. Following fixation the cells are probed with anti-TDP-43 antibody (Santa Cruz Labs). Total TDP-43 levels and cytoplasmic inclusion formation are analyzed by confocal microscopy. The effects of compounds that appear to reduce endogenous TDP-43 levels can be further examined by treating cortical and motor neurons with the compound (0, 1 hr and 24 hrs, dose=1 and 3×Ki) and immunoblotting the TDP-43 to quantify the levels of TDP-43 and compare to levels of other proteins, such as TIA-1 (a stress granule protein) and actin (a housekeeping protein).

Determine how the Lead Compounds Affect Stress Granule Formation:

TDP-43 is transduced into primary cultures of spinal cord neurons with lentiviruses±test compounds (dose: 1 & $5 \times IC_{50}$). After 24 hrs treatment with test compounds, neurons are treated±0.5 mM arsenite, 1 hr, and fixed. Following fixation, colocalzation of TDP-43 with SG markers (TIA-1 or eIF3) is determined by immunocytochemistry as described by us previously (*PLoS ONE*, October 2010 5(10), e13250; herein incorporated by reference in its entirety).

Whether the compounds inhibit aggregation of recombinant TDP-43 in vitro can be tested as follow. Fresh recombinant TDP-43 (3 µM) is incubated in solution±test compounds (dose=Ki*(0.5, 1, 2, 4 or 10)), and aggregation is followed spectrophotometrically by the increase in turbidity at 395 nm over 1 hr Biol Chem, 2009. 284: 20329-39; herein incorporated by reference in its entirety).

The strong correlation between neurodegeneration and inclusion formation translates into identifying compounds that inhibit neurodegeneration in addition to inhibiting inclusion formation. Without wishing to be bound by a theory, the excellent potency arises because the assay is modulating the signaling systems that regulate stress granule formation because enzymatic reactions such as kinase reactions are commonly very sensitive to small molecule therapeutics. There can be multiple pathways for inhibiting TDP-43 inclusion formation, including: 1) inhibition of stress granule formation, 2) inhibition of nuclear TDP-43 export, 3) homomeric inhibition TDP-43 binding (one TDP-43 molecule to another), 4) heteromeric inhibition TDP-43 binding (binding of TDP-43 to other aggregating stress granule proteins, such as TIA-1 or eIF3). Inhibiting nuclear export is unlikely because the compounds also inhibit intra-nuclear inclusions.

Cell Culture:

Primary motor neuron cultures are generated as described previously (Neuroscience, 2009. 159: 647-56; herein incorporated by reference in its entirety). Mouse spinal cord neurons are isolated from embryonic day 12.5 pups. Cholinergic neurons are isolated by FACS acid cultured at 5000 cells per $cm^2$. Motoneurons were plated in the presence of a cocktail of neurotrophic factors (referred as "NTFs": 1 ng/ml BDNF, 100 pg/ml GDNF, 10 ng/ml CNTF) in neural basal medium added at the time of cell seeding (Neuron, 2002. 35: 1067-83; herein incorporated by reference in its entirety). Cortical neurons are isolated from from E17.5 mouse brains. Neurons were plated in neurobasal medium supplemented with B27, 0.5 mM glutamine and penicillin/streptomycin onto poly-D-lysine/laminin coated dishes (J Biol Chem, 2004. 279: 46915-20; herein incorporated by reference in its entirety). PC12 cells are grown in DMEM, 10% NBS/Pen-Strep, 100 μg/ml hygromycin, 50 μM puromycin and 50 μg/ml doxycycline (the latter is removed for TDP-43 induction).

Immunocytochemistry: can be performed as described previously (J Neurochem, 2010, 112, 6, 1593-1604; herein incorporated by reference in its entirety).

LDH assay: can be performed as described previously (J. Neuroscience, 2000. 20: 6048-54; herein incorporated by reference in its entirety).

Animals: Timed pregnant female C57/B6 mice can be used for isolating primary neurons. Approximately 78 pregnant mice to are needed to generate primary cultures of cortical neurons. This number is based on the use of 26 pregnant mice in the first year (1/wk for 6 months) and 52 pregnant mice in the second year (1/wk). Pregnant mice can be purchased (for non-transgenic mice) or generated from the colony of ChAT::GFP mice maintained at Boston University School of Medicine by Krzysztof Blusztajn. In one embodiment, C57/B6 WT and ChAT::GFP are used because of published studies utilizing mouse primary cultured neurons to investigate the pathogenesis of ALS/FTLD-U and TDP-43 expression and function, and the utility of having mice with labeled cholinergic neurons. The mice can be killed by inhalation of carbon dioxide, which is an approved, humane method of sacrifice. These methods are consistent with the recommendation of the Panel on Euthanasia of the American Veterinary Medical Association.

Determining whether compounds delay deterioration of motor function in C. elegans expressing TDP-43 in C. elegans: C. elegans is generally used as a simple in vivo model of disease bridging the gap between in vitro studies and in vivo studies in rodents (J Biol Chem, 2005. 280: 42655-68; J Neurosci, 2009. 29: 9210-8; Neurodegener Dis, 2010. 7: 68-75; each herein incorporated by reference in its entirety). Accordingly, C. elegans lines expressing TDP-43 (WT, G294A and A315T), obtained from Brian Kraemer, can be used to determine whether the indentified compounds ameliorate motor dysfunction associated with TDP-43 expression (J Neurosci, 2010. 30: 16208-19; herein incorporated by reference in its entirety). For the experiments, lines of C. elegans (30 per plate, 3 plates per dose) are synchronized and plated onto NGM plates containing the test compound at L3, using dose ranges of 0, 1, 10 and 100×IC50; higher doses are used because C. elegans are typically less sensitive to compounds than cultured cells. The nematodes are aged on the plates, and transferred to fresh plates every other day. Movement and survival are calculated at adult days 1, 3 and 5, using methods described in the art (see, e.g., J. Neurosci. 2010 December 1, 30(48):16208-19; IEEE Trans Biomed Eng. 2004 October 51(10):1811-20, each herein incorporated by reference in its entirety).

In one example, eggs (C. elegans expressing A315T TDP-43, line CK426) were plated on agar containing the test compound. On day 4, movement of C. elegans was quantified and moved to plates with fresh compounds. On day 5, movement of C. elegans was again quantified.

Figure 15A:
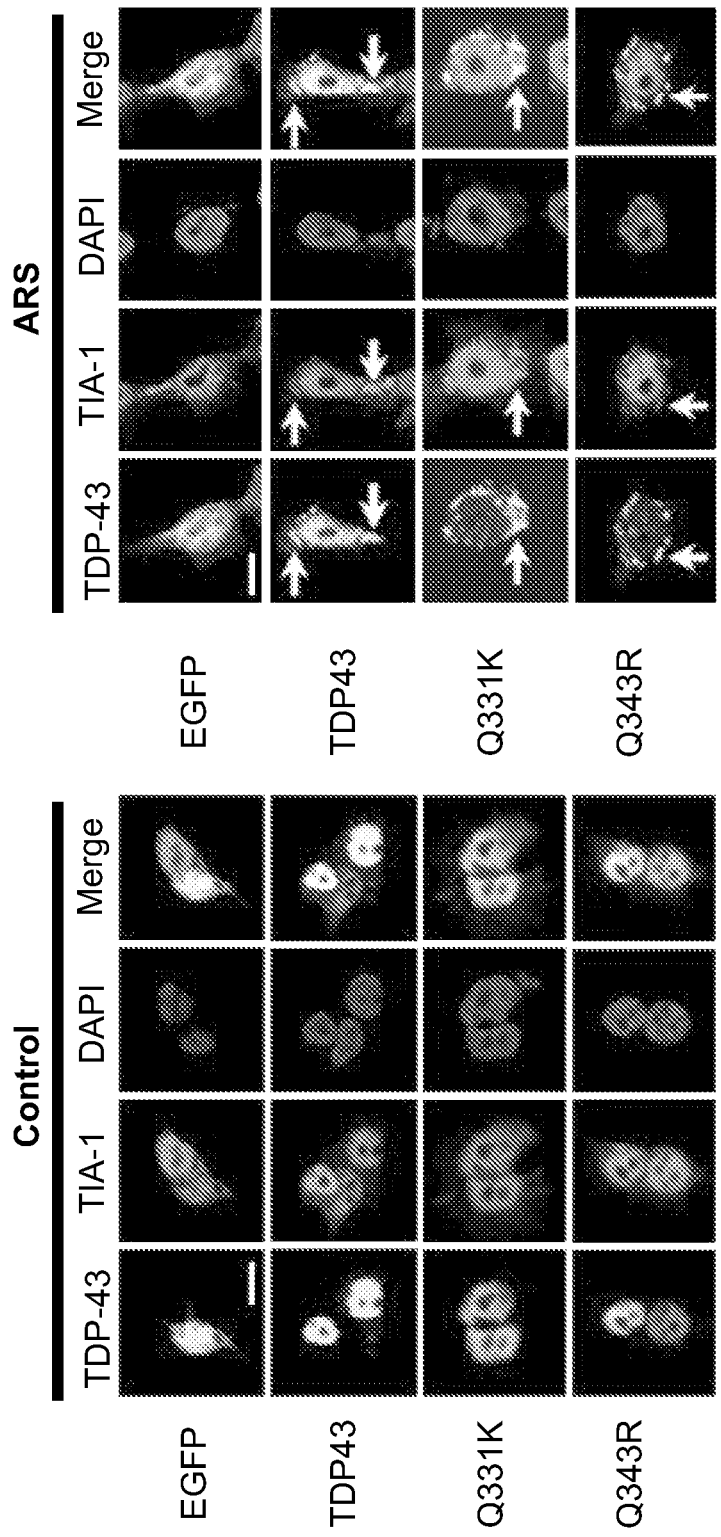
FIG. 15A, stresses, such as arsenite (0.5 mM, 1 hr) induce TDP-43 to translocate from the nucleus to the cytoplasm where it forms granules that co-localize with SG markers (e.g., TIA-1). Disease-linked mutations in TDP-43 increase the amount of cytoplasmic translocation and inclusion formation. Arrows point to cytoplasmic SG.

Expressed or Endogenous TDP-43 Forms Cytoplasmic Inclusions that Co-Localize with SG:

The inventors transfected human BE-M17 neuroblastoma cells with WT TDP-43, TDP-$43_{86-414}$ or TDP-$43_{216-414}$ constructs N-terminally tagged with GFP. Full length WT TDP-43 localized to the nucleus under basal conditions (FIG. 15, WT TDP-43 shown). To investigate TDP-43 aggregation under the stressful conditions, cells were exposed to arsenite, an agent classically used to induce SGs (Biochem Soc Trans, 2002, 30, 963-9; J Cell Biol, 2000, 151, 1257-68; J Cell Biol, 1999, 147, 1431-42; each herein incorporated by reference in its entirety). Arsenite causes stress through multiple mechanisms (Toxicol Appl Pharmacol, 2001, 177, 132-48; herein incorporaed by reference in its entirety). Arsenite directly induces oxidative stress by reacting with oxygen in a reaction similar to the Fenton reaction, and arsenite also uses up glutathione, which causes further oxidative stress (Toxicol Appl Pharmacol, 2001, 177, 132-48; herein incorporaed by reference in its entirety). Upon exposure to arsenite (1 hr) WT TDP-43 remained largely nuclear, but a small amount translocated to the cytoplasm where it formed inclusions (FIG. 15A, right panels, arrows). To determine whether the inclusions co-localized with SGs, we co-labeled the cells with antibodies to SG markers, including TIA-1, eIF3 and poly-A binding protein (PABP) (FIG. 15). Double labeling experiments indicated that inclusions composed of WT TDP-43 co-localized with SG markers under arsenite-induced conditions (FIG. 15A, TIA-1 shown as SG marker, arrows); TDP-43 inclusions also co-localized with SG markers under basal conditions, but the fraction of cells (<10%) exhibiting TDP-43 inclusions under basal conditions. Co-localization with other SG markers is also observed. Similar results were obtained when experiments were performed using HEK 293 cells (not shown).

Figure 15B:
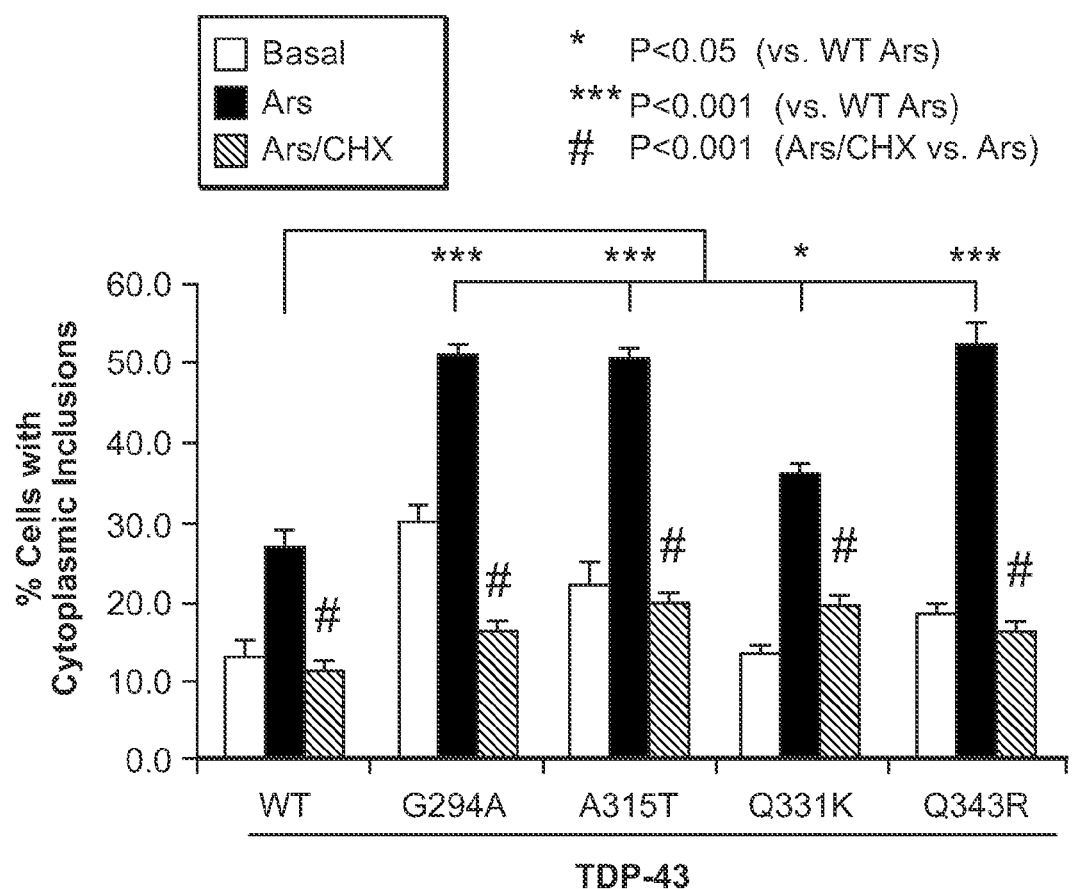
FIG. 15B, shows quantification of cells with SGs.

Disease-Linked Mutations Enhance Cytoplasmic Translocation and SG Formation:

The strong link between TDP-43 and SG biology prompted us to examine whether disease-linked mutations in TDP-43 also enhance formation of inclusions through processes linked to SGs. GFP-tagged TDP-43 (WT, G294A, A315T, Q331K, Q343R) were transfected into BE-M17 cells, and inclusion formation was examined after treatment with arsenite (0.5 mM, 1 hr) in the presence or absence of cycloheximide (50 μg/ml, 1 hr, FIG. 15A). The mutations moderately increased TDP-43 inclusion formation under basal conditions (FIG. 15B). Arsenite treatment was associated with more inclusion formation for mutant TDP-43 constructs than for WT TDP-43 (FIGS. 15A & B). The inclusions that formed in response to arsenite fully co-localized with TIA-1, suggesting that inclusion formed by mutant TDP-43 were also SGs (FIG. 15A). In each case, formation of inclusions composed of mutant TDP-43 constructs was reversible by cylcoheximide (10 μg/ml, 1 hr, FIGS. 15A & B). Importantly, each of the mutations also showed a striking decrease in nuclear localization in response to arsenite treatment, suggesting that the mutations increased the degree of nuclear export (FIGS. 15A & B). The enhanced stress-induced cytoplasmic localization associated with these mutants might contribute to their strong tendency to form inclusions. These data demonstrate that enhancement of inclusions with properties resembling SGs is a common feature of TDP-43 mutations associated with ALS. In addition, toxicity studies examining the vulnerability of neurons expressing mutant TDP-43 results provide evidence that disease-linked TDP-43 mutations increase cell death processes and SG formation.

TDP-43 Inclusions in Brain Tissue from ALS and FTLD-U Donors Co-Localize with SG Markers:

Finally we examined whether TDP-43 pathology present in ALS and FTLD-U cases were associated with SG markers. Immunocytochemistry was performed on cases of ALS and FTLD-U using antibodies to TDP-43 and SG markers, including eIF3 and TIA-1. Sudan black was used to remove endogenous autofluorescence due to lipofuscin (data not shown); this method greatly increased the ability to distinguish between fluorescence related to the antibody signal and fluorescence caused by lipofuscin. Using sudan black to remove autofluorescence, we were able to readily visualize TDP-43 positive inclusions that showed co-labeling with these SG markers in ALS spinal cord tissue and FTLD-U brain (FIGS. 16A&B). We also observed co-localization between phospho-TDP-43 inclusions and eIF3 or TIA-1 (FIG. 16D). The specificity of eIF3 staining was tested by immuno-adsorption; pre-absorption of TDP-43 antibodies with the antigenic peptide eliminated all reactivity, indicating the specificity of the antibody (FIG. 16C). The absence of reactivity following pre-adsorption also demonstrated that labeling of SG markers was not due to the artifact of "bleed-through" from the green channel. No co-labeling was observed with antibody to a different class of RNA-binding protein, the P-body marker anti-Dcp1 (data not shown). Thus inclusions containing TDP-43 in the FTLD-U brain and ALS spinal cord also contain other SG proteins, which is consistent with a hypothesis that SG biology is intimately linked to the mechanisms underlying TDP-43 inclusion formation.

Figure 17:
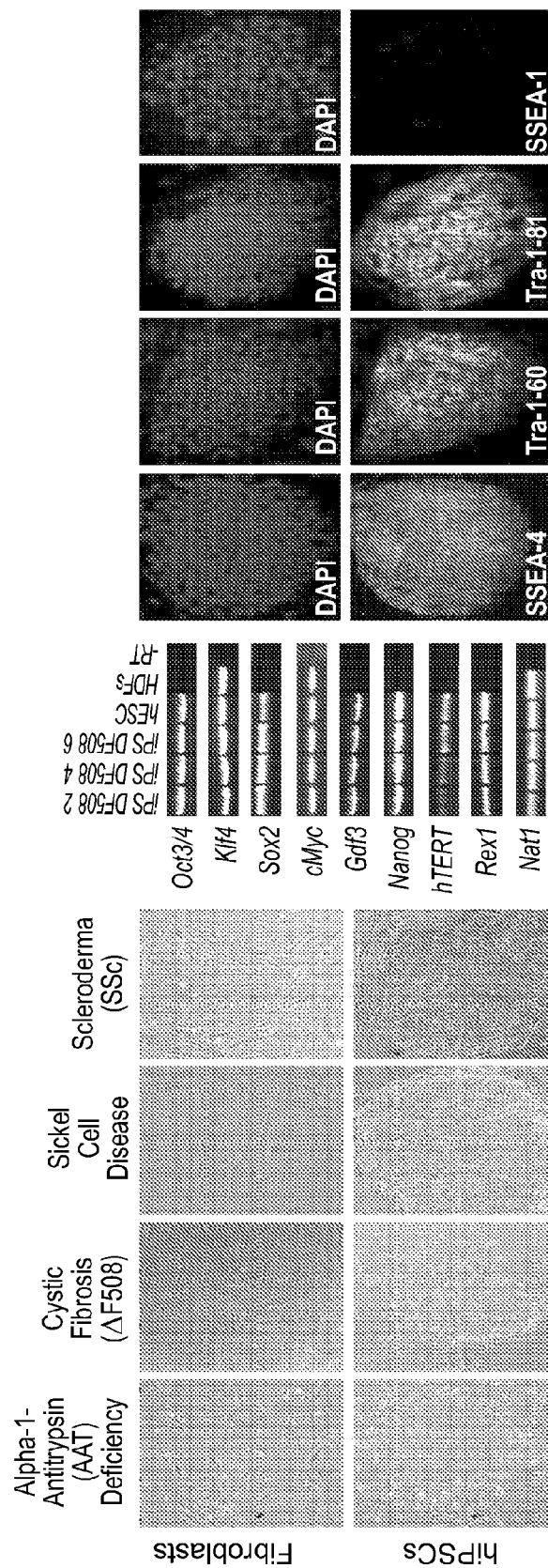
FIG. 17 shows derivation and characterization of human iPS (hiPS) cell clones generated using a floxed single lentiviral stem cell cassette (STEMCCA). Panel 1: Human fibroblasts in culture and their reprogrammed iPSC progeny, derived from individuals with alpha-1 antitrypsin deficiency, cystic fibrosis, sickle cell disease, and scleroderma (SSc). Panel 2: Characterization of reprogrammed human clones by RT-PCR (vs.hES and HDF controls) Panel 3: Characterization of reprogrammed human clones (intra vital immunostaining on live cells).

Induced Pluripotent Stem Cells (iPSCs) Form Motor Neurons:

To establish a simplified method for the derivation of iPSCs, we sought to develop a vector that would result in efficient reprogramming with a single reagent, without the need for concurrent additional vectors, transgenes, or chemical exposures. Importantly, the use of a single polycistronic vector, expressing Oct4, Klf4, Sox2, and c-Myc, allowed us to reprogram post-natal somatic cells with an efficiency 50 fold greater than previously published methods, and with a single viral integration (*Stem Cells.* 2010, 28 (10), 1728-1740; *Stem Cells,* 2009, 27, 543-9; each herein incorporated by reference in its entirety). We have now adapted this vector (STEMCCA-loxP) by replacing all four reprogramming factors with their corresponding human counterparts to create a humanized STEMCCA-loxP vector. This vector allows for the efficient derivation of human iPSCs (FIG. 17).

Directed Differentiation of Human iPSCs into Motor Neurons.

Figure 18:
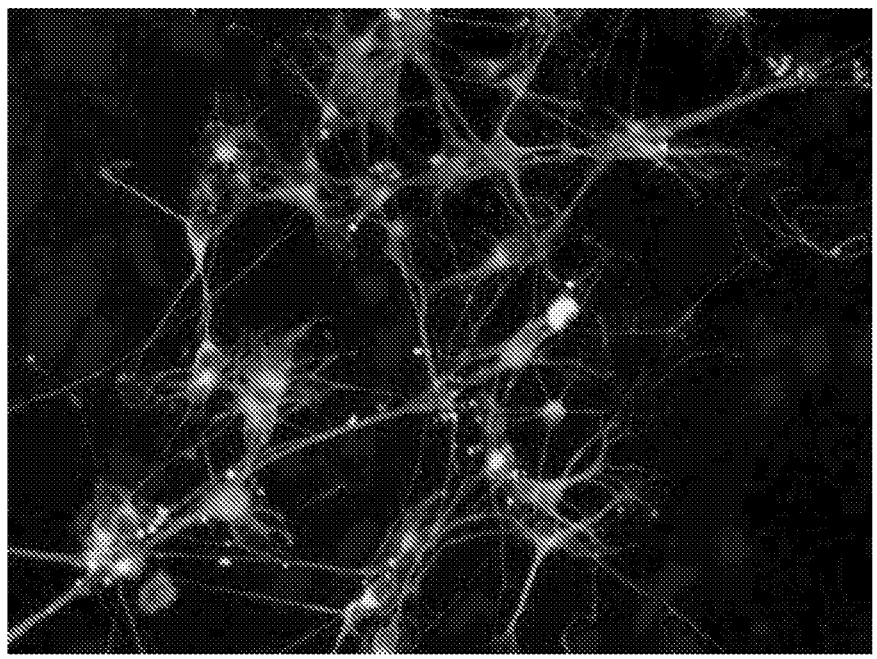
FIG. 18 shows differentiated iPSCs stained markers: Neuronal class III b-Tubulin (green) and homeobox protein DLX4/HB9 (red, motor neuron specific).
Figure 20A:
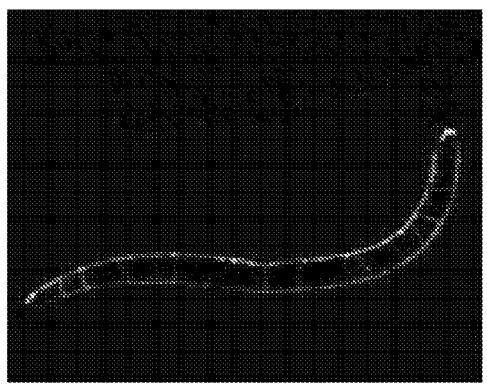
FIG. 20 shows (A) *C. elegans* normally have 19 motor neurons, each of which shows strong connectivity; (B) *C. elegans* line expressing human A315T TDP-43 shows a dramatic loss of motor neurons by adult day 2; (C) when grown in the presence of compound 8, motor neuron survival is strongly increased. This is evident by counting the number of neuronal cell bodies or counting the number of neurons lacking connections (Dose=34.8 µM); (D) quantification of neuronal loss (left panel) and loss of connectivity (right panel) shows 50% and 70% decreases with compound 8.
Figure 20B:
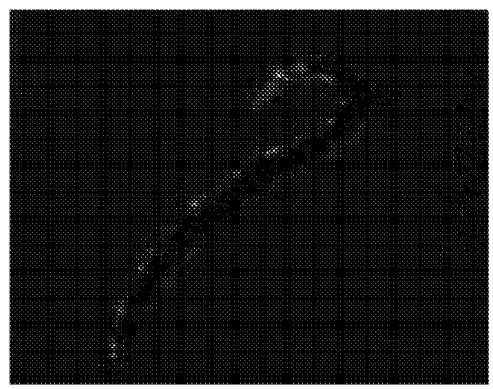
Figure 20C:
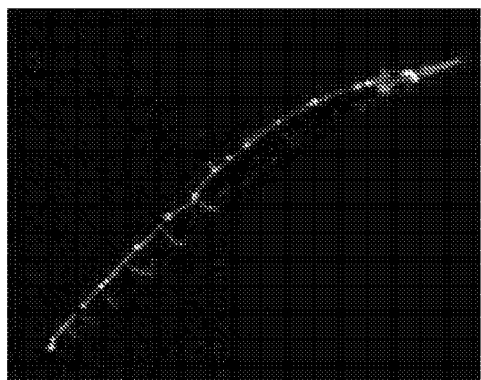
Figure 20D:
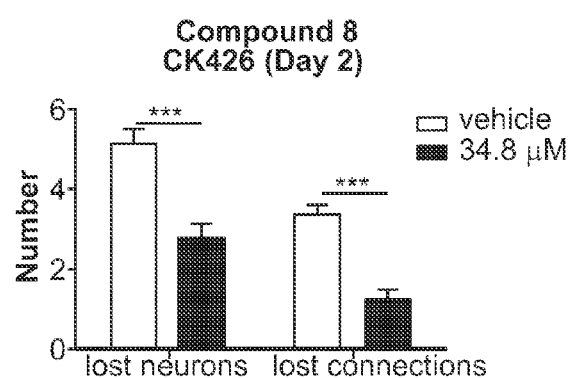

To develop a novel source of motor neurons for neurodegenerative research, we established conditions for the efficient directed differentiation of human iPSCs into motor neurons based on our protocol initially used for human Embryonic Stem cells[12] (Nat. Biotechnol., 2009 27(3): 275-80, herein incorporated by reference in its entirety). For this adaptation, human iPSCs were cultured on OP9 feeder cells in differentiation media (IMDM, 20% FBS, 100 ng/ml ROCK-1) for 5 days, followed by passaging and further differentiation in NIM media supplemented with retinoic acid (0.1 uM), ascorbic acid (0.4 ug/ml), dbcAMP (1 uM), and 0.1 uM Human hedgehog Agonist (hAg) until day 24, transfer to medium with B-27 (1×), BDNF, GDNF, IGF-1 and CTNF (10 ng/mL) for 3 days, and plating on laminin for before experimental analysis. Using this co-culture protocol, motor neurons emerged, were collected and characterized as shown in FIG. 18 to confirm expression of two accepted motor neuron markers.

Modification of motor function in nematodes over-exspressing TDP-43 with the compounds.

Some of the exemplary compounds described herein were tested in a in vivo system using *C. elegans* expressing WT or A315T TDP-43. The nematode lines were hatched on agar plates containing varying doses of test compound; we used doses that were 10-200× the IC50 observed with cell lines because *C. elegans* tend to be much less sensitive to exogenous compounds than cells grown in culture. Worms typically need doses of compound that are 10-100 fold greater than in mammals due to the environment (dirt) and have strong protective mechanisms—such as a thick cuticle that is resistant to chemicals. Interestingly, many of the compounds tested modify motor function, but the effects varied depending on the compound. For instance, compound 8 (LDN-0130436) improved motor function to similar degrees in *C. elegans* expressing human WT or A315T TDP-43 (FIG. 19A, WT shown), but exhibited little effect on the non-transgenic N2 line (FIG. 19B). In contrast, compound 8 strongly inhibited motor function in *C. elegans* expressing WT TDP-43 (FIG. 19C) or in the N2line, but had only a modest effect on the A315T line (FIG. 19D). Another compound increased motor function by about 6-fold in all the lines. Each of these compounds dispersed TDP-43 inclusions in PC12 cells and in other cell lines, yet exhibited disparate actions in *C. elegans*. Multiple different pathways are known to modulate formation of SGs, including the pathways mediated by kinases that phosphorylate eIF2A, PERK, HRI and GCNA, as well as pathways that proceed independently of eIF2A. Thus, without wishing to be bound by a theory, the differential motor phenotypes observed for the different compounds in *C. elegans* can reflect different mechanisms of action for each compound.

Using these GFP-labeled *C. elegans* lines, we observe that compound 8 increases survival of motor neurons (FIG. 20). We used the nematode line expressing A315T TDP-43 for the study because this line shows the most age-dependent visible loss of motor neurons. The nematodes were hatched and grown on plates containing compound 8 (dose=34.8 μM, which corresponds to 200× IC50). Pictures were taken at adult day 2 (FIGS. 20A-C) and neuronal loss was quantified (FIG. 20D). Two different measures were used for quantifying neuronal loss. One method was to count the number of visible neuronal cell bodies (FIG. 20D). Using this method we observed that compound 8 elicited an 50% decrease in neuronal loss, which was highly significant (FIG. 20D). The second method quantified the number of neurons that did not have visible connections to other neurons. This measure is readily observable in FIG. 20D. Note that the vehicle treated nematodes have some neurons that exist as isolated cell bodies without visible processes connecting them to other neurons; such neurons were counted as "lacking connections". In contrast, nematodes treated with compound 8 show very few (if any) neurons lacking connections. These results are quantified in FIG. 20D. Using this method we observed that compound 8 elicited reduced the number of neurons lacking connections by almost 70% (69.3%, FIG. 20D).

Figure 21:
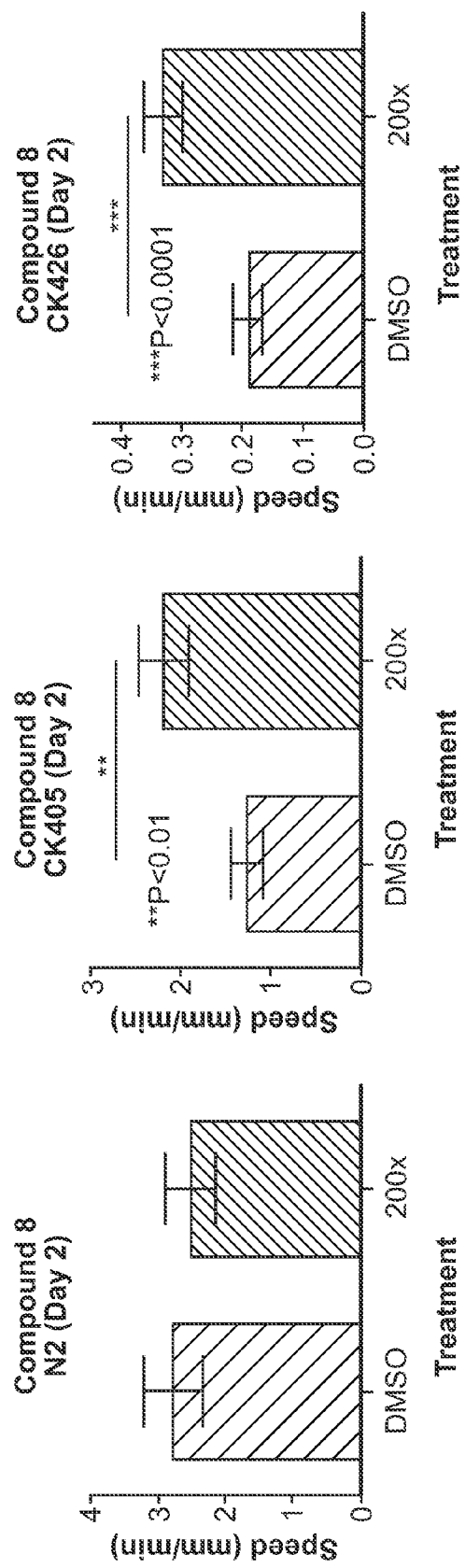
FIG. 21 shows results showing motor improvement in lines of *C. elegans* that express human WT TDP-43 (CK405), A315T TDP-43 (CK426) or non-transgenic (N2) (Dose=34.8 µM).

Compound 8 also improves motor function by a similar percentage in *C. elegans* expressing human WT or A315T TDP-43 (FIG. 21), but exhibits little effect on the non-transgenic N2 line. Nematodes expressing human WT TDP-43 show about a 65% loss of function, and this functional loss is restored by treatment with compound 8 (FIG. 21, middle panel). Nematodes expressing human A315T TDP-43 show a more severe loss of motor function (~93%). Compound 8 improves motor function by a percentage similar to that of WT TDP-43, but this is not sufficient to restore motor function up to the normal level of functioning (FIG. 21C, middle panel). One of the aspects of compound 8 action that captures our attention is that it has no affect on motor function in nematodes that do not express TDP-43, suggesting that it is selective for TDP-43. In contrast, compound 7 improves motor function in non-transgenic AND transgenic TDP-43.

Figure 22:
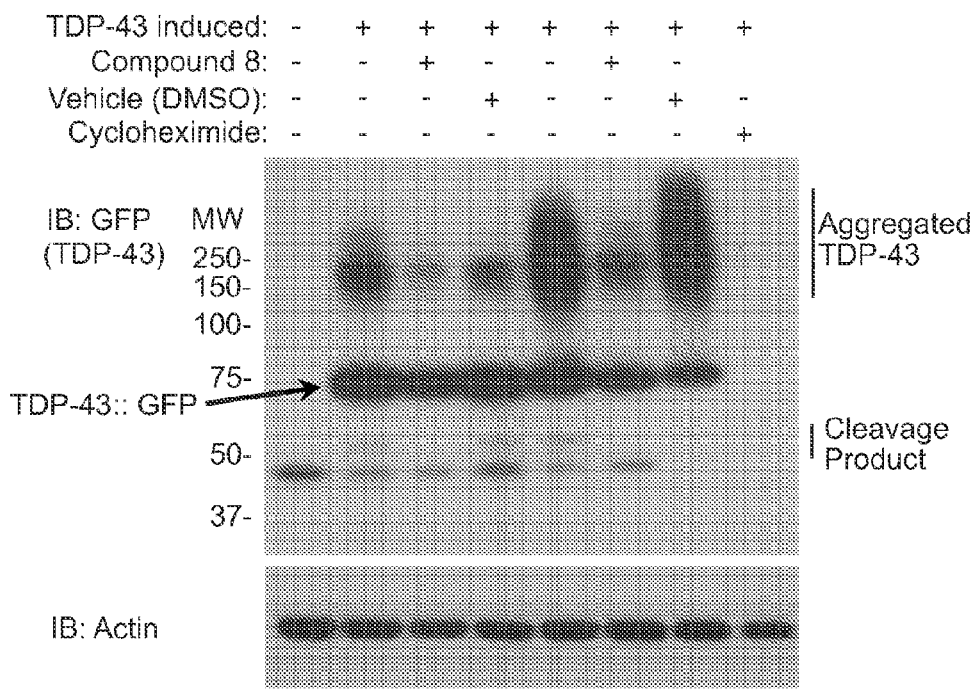
FIG. 22 shows treatment of PC12 cells expressing A315T TDP-43::GFP show reduced levels of insoluble TDP-43 after treatment with compound 8.

Reduction of Levels of Insoluble TDP-43:

The previous study demonstrates that the amount of insoluble TDP-43 increases in response to treatment with arsenic, which corresponds to with induction of stress granules. We used the tetracycline inducible PC12 cells expressing human WT TDP-43::GFP. Using these cells, we induced TDP-43 expression, and treated with arsenic (0.5 M, 1 hr)±compound 8 (3.5 µM). The cells were then lysed, fractionated into soluble/insoluble and then immunoblotted. The results in FIG. 22 show that arsenite increases amount of aggregated TDP-43::GFP, which is consistent with our prior results. Cells treated with compound 8 show an absolutely striking reduction in levels of high molecular weight aggregated TDP-43 under basal conditions or after treatment with arsenite (FIG. 22). One can also see that expressing TDP-43 leads to formation of a lower molecular weight TDP-43 band, which might be a TDP-43 cleavage fragment (arrow, FIG. 22). Treatment with compound 8 eliminates this cleavage fragment (FIG. 22). We also fractionated the cell lysates and demonstrated that compound 8 causes an equally impressive translocation of TDP-43::GFP from the insoluble to the soluble fraction.

Figure 23:
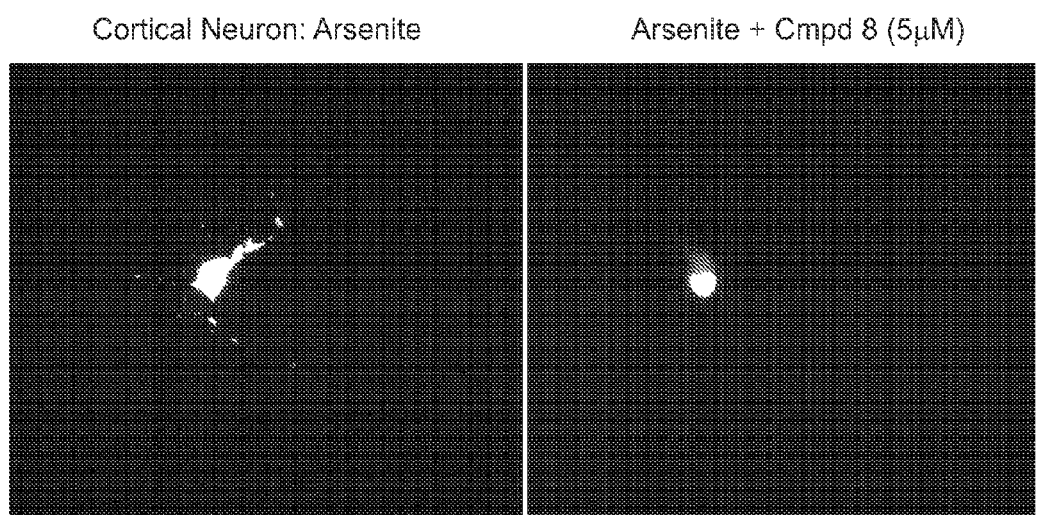
FIG. 23 shows rat cortical neuron (DIV7) transfected with A315T TDP-43 and treated +/−compound 8 for 18 hr. Treatment with compound 8 induces nuclear localization of TDP-43.

Translocation of TDP-43::GFP from the Cytoplasm to the Nucleus:

Increasing data suggest that the process of ALS leads to loss of TDP-43 expression in the nucleus and increased expression in the cytoplasm. It is hypothesized that this loss of TDP-43 nuclear expression leads to the neurodegeneration associated with ALS. We examined the effects of compound 8 on the localization of TDP-43 in rat hippocampal neurons transfected with human A315T TDP-43 and treated with arsenite (FIG. 23). Hippocampal neurons show increased cytoplasmic translocation of TDP-43 under conditions of arsenite treatment compared to basal conditions, and of A315T TDP-43 compared to WT TDP-43. FIG. 23 demonstrates the striking effects of compound 8, which causes a dramatic shift in localization of TDP-43 from the cytoplasm to the nucleus. This contrasts with the theory that loss of nuclear TDP-43 is actually what causes the disease. Thus, compound 8 might have the ability to increase levels of nuclear TDP-43.

Figure 24:
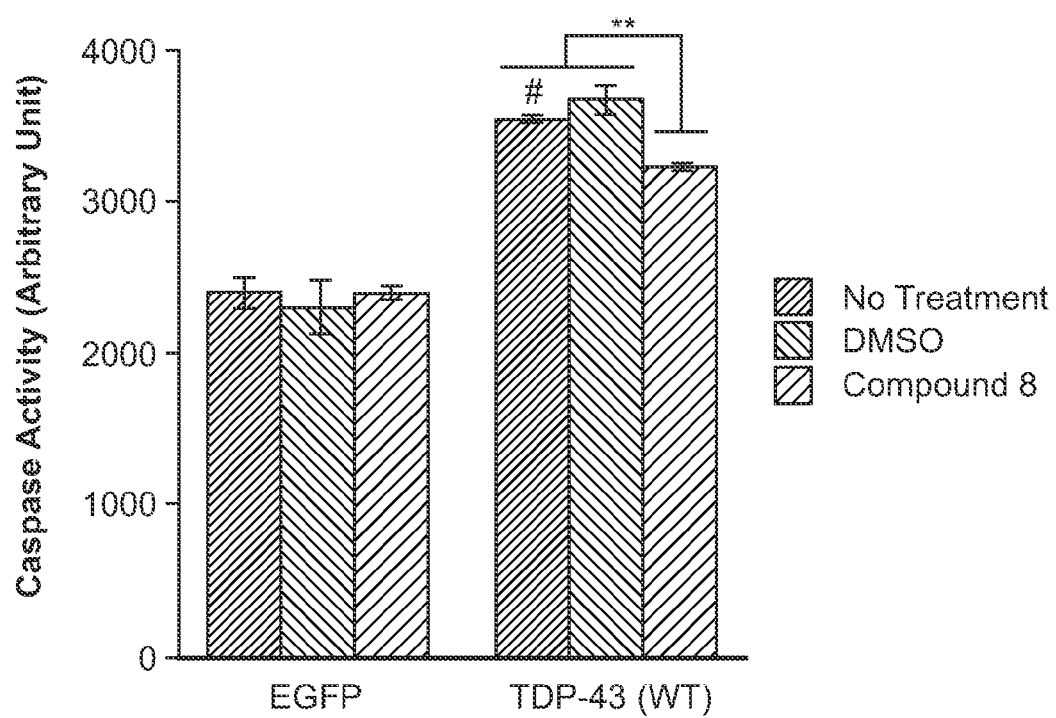
FIG. 24 shows compound 8 protects against induction of caspase activity in hippocampal neurons expressing WT TDP-43.

Compound 8 Protects Against Neurotoxicity:

An important question is whether the compounds will work on protect against toxicity induced by TDP-43. To test this, we transfected primary cultures of hippocampal neurons with EGFP or WT-TDP-43; transfection efficiency was 30%. The following day we measured caspase activity. There was a moderate level of baseline activity evident in the EGFP transfected cells. However, cells transfected with TDP-43 showed more caspase activity, and about half of this increase was reversed by pretreatment with compound 8 (FIG. 24). Without being bound by theory, this strongly suggests that compound 8 might be protect against toxicity related to TDP-43, and protect neurons. Inclusions are one thing, but the bottom line is neuron death. The nematode assay provides strong evidence of neuroprotection. FIG. 24 shows neuroprotection in primary cultures of hippocampal neurons. This was done using a fluorescent assay using a substrate for caspase 3 that fluoresces after cleavage (sold by Promega Corp. and Biotum). This assay has also been performed using an antibody that only detects cleaved caspase 3 (Cell Signaling Inc).

Figure 25:
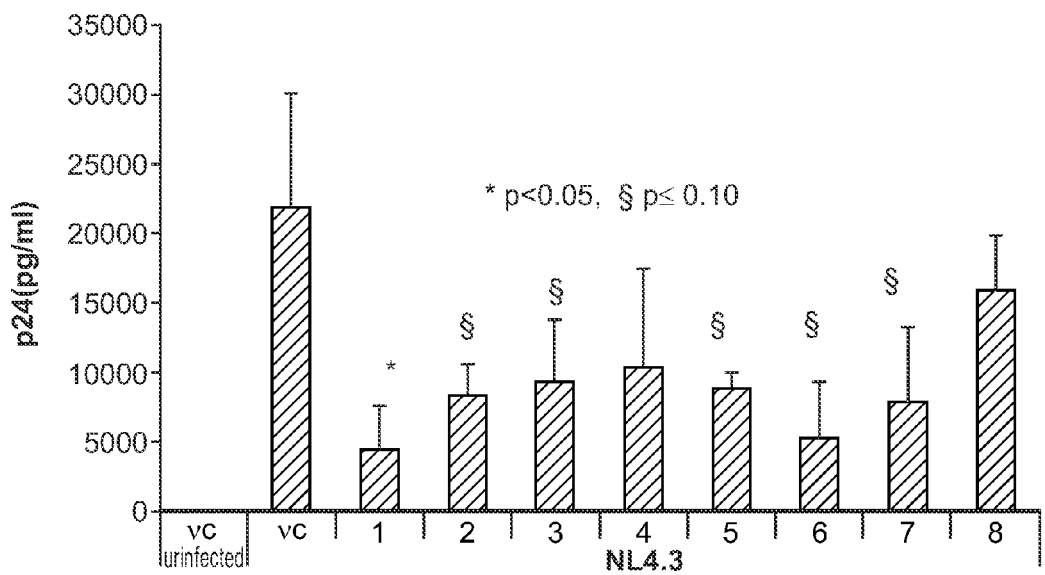
FIG. 25 shows inhibition of HIV replication with compounds.
Figure 26:
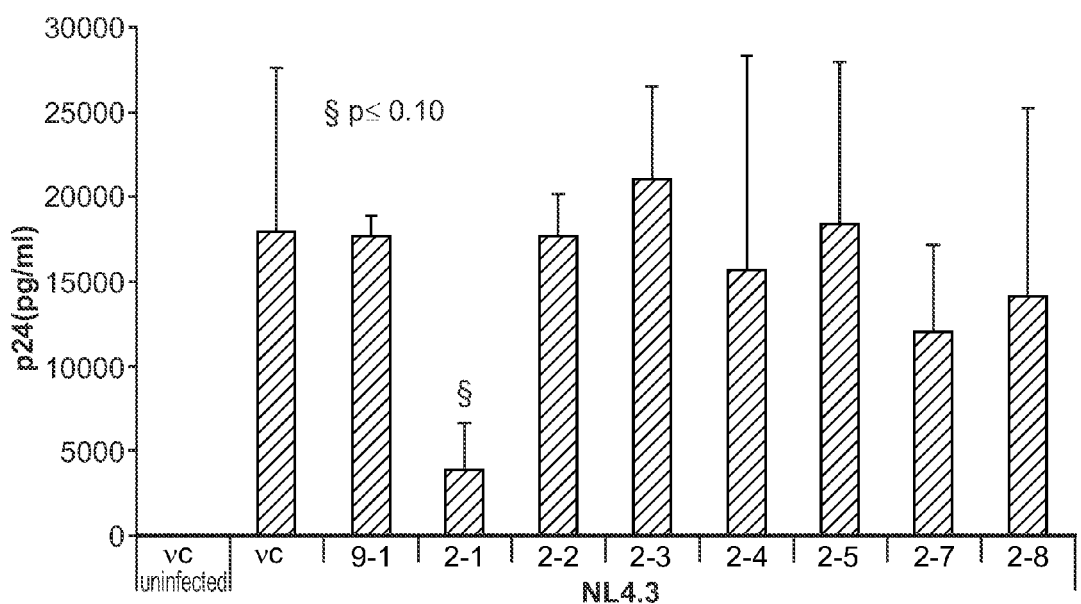
FIG. 26 shows inhibition of HIV replication with compounds.

Compounds for TDP-43 aggregation inhibition also inhibit replication of HIV. Several compounds were assayed to explore inhibition of HIV replication. The assay used was a p24 ELISA assay (*Proc Natl Acad Sci USA*. 2008 May 6; 105(18):6684-9; herein incorporated by reference in its entirety). Inhibition of HIV replication for several compounds (listed on axis) is shown in FIGS. 25 and 26.

REFERENCES

Abhyankar, M. M., C. Urekar, and P. P. Reddi. (2007). A novel CpG-free vertebrate insulator silences the testis-specific SP-10 gene in somatic tissues: role for TDP-43 in insulator function. J Biol Chem, 282, 36143-54.

Anderson, P. and N. Kedersha, Stress granules: the Tao of RNA triage. Trends Biochem Sci, 2008. 33: 141-50.

Ash, P. E., Y. J. Zhang, C. M. Roberts, T. Saldi, H. Hutter, E. Buratti, L. Petrucelli, and C. D. Link. (2010). Neurotoxic effects of TDP-43 overexpression in *C. elegans*. Hum Mol Genet, 19 (16): 3206-3218.

Barmada, S. J., et al., Cytoplasmic mislocalization of TDP-43 is toxic to neurons and enhanced by a mutation associated with familial amyotrophic lateral sclerosis. J Neurosci, 2010. 30: 639-49.

Buratti, E. and F. E. Baralle. (2001). Characterization and functional implications of the RNA binding properties of nuclear factor TDP-43, a novel splicing regulator of CFTR exon 9. J Biol Chem, 276, 36337-43.

Buratti, E., A. Brindisi, M. Giombi, S. Tisminetzky, Y. M. Ayala, and F. E. Baralle. (2005). TDP-43 binds heterogeneous nuclear ribonucleoprotein A/B through its C-terminal tail: an important region for the inhibition of cystic fibrosis transmembrane conductance regulator exon 9 splicing. J Biol Chem, 280, 37572-84.

Chambers, S. M., C. A. Fasano, E. P. Papapetrou, M. Tomishima, M. Sadelain, and L. Studer. (2009). Highly efficient neural conversion of human ES and iPS cells by dual inhibition of SMAD signaling. Nat Biotechnol, 27, 275-80.

Collas, P. and J. A. Dahl. (2008). Chop it, ChIP it, check it: the current status of chromatin immunoprecipitation. Front Biosci, 13, 929-43.

Colombrita, C., et al., Tdp-43 Is Recruited to Stress Granules in Conditions of Oxidative Insult. Neurochem, 2009, 111 (4), 1051-1061.

Del Razo, L. M., B. Quintanilla-Vega, E. Brambila-Colombres, E. S. Calderon-Aranda, M. Manno, and A. Albores. (2001). Stress proteins induced by arsenic. Toxicol Appl Pharmacol, 177, 132-48.

Ebert, A. D., J. Yu, F. F. Rose, Jr., V. B. Mattis, C. L. Lorson, J. A. Thomson, and C. N. Svendsen. (2009). Induced pluripotent stem cells from a spinal muscular atrophy patient. Nature, 457, 277-80.

Elden, A. C., H. J. Kim, M. P. Hart, A. S. Chen-Plotkin, B. S. Johnson, X. Fang, M. Armakola, F. Geser, R. Greene, M. M. Lu, A. Padmanabhan, D. Clay-Falcone, L. McCluskey, L. Elman, D. Juhr, P. J. Gruber, U. Rub, G. Auburger, J. Q. Trojanowski, V. M. Lee, V. M. Van Deerlin, N. M. Bonini, and A. D. Gitler. (2010). Ataxin-2 intermediate-length polyglutamine expansions are associated with increased risk for ALS. Nature, 466, 1069-75.

Frasier, M., M. Walzer, L. McCarthy, D. Magnuson, J. M. Lee, C. Haas, P. Kahle, and B. Wolozin. (2005). Tau phosphorylation increases in symptomatic mice overexpressing A30P alpha-synuclein. Exp Neurol, 192, 274-87.

Gilks, N., N. Kedersha, M. Ayodele, L. Shen, G. Stoecklin, L. M. Dember, and P. Anderson. (2004). Stress granule assembly is mediated by prion-like aggregation of TIA-1. Mol Biol Cell, 15, 5383-98.

Gitcho, M. A., et al., TDP-43 A315T mutation in familial motor neuron disease. Ann Neurol. 2008, 63(4), 535-538.

Glanzer, J., K. Y. Miyashiro, J. Y. Sul, L. Barrett, B. Belt, P. Haydon, and J. Eberwine. (2005). RNA splicing capability of live neuronal dendrites. Proc Natl Acad Sci USA, 102, 16859-64.

Guillily, M., H. Li, J. C. Latourelle, N. Pyenson, L. Richter, G. Raghavan, R. H. Myers, J. J. Collins, and B. Wolozin. (2010). A LRRK2 Network Interaction Map: Identification of genes regulating dopaminergic neruonal survival. Submitted.

Hanson, K. A., S. H. Kim, D. A. Wassarman, and R. S. Tibbetts. (2010). Ubiquilin modifies TDP-43 toxicity in a Drosophila model of amyotrophic lateral sclerosis (ALS). J Biol Chem, 285, 11068-72.

Hsu, C. H., D. Chan, and B. Wolozin, LRRK2 and the Stress Response: Interaction with MKKs and JNK-Interacting Proteins. Neurodegener Dis, 2010. 7: 68-75.

Hsu, C. H., et al., MKK6 binds and regulates expression of Parkinson's disease-related protein LRRK2. J Neurochem, 2010, 112, 6, 1593-1604.

Johnson, B. S., et al., TDP-43 is intrinsically aggregation-prone, and amyotrophic lateral sclerosis-linked mutations accelerate aggregation and increase toxicity. J Biol Chem, 2009. 284: 20329-39.

Kedersha, N. and P. Anderson, Stress granules: sites of mRNA triage that regulate mRNA stability and translatability. Biochem Soc Trans, 2002. 30: 963-9.

Kedersha, N., M. R. Cho, W. Li, P. W. Yacono, S. Chen, N. Gilks, D. E. Golan, and P. Anderson. (2000). Dynamic shuttling of TIA-1 accompanies the recruitment of mRNA to mammalian stress granules. J Cell Biol, 151, 1257-68.

Kedersha, N. L., M. Gupta, W. Li, I. Miller, and P. Anderson. (1999). RNA-binding proteins TIA-1 and TIAR link the phosphorylation of eIF-2 alpha to the assembly of mammalian stress granules. J Cell Biol, 147, 1431-42.

Klein, R. L., R. D. Dayton, N. J. Leidenheimer, K. Jansen, T. E. Golde, and R. M. Zweig. (2006). Efficient neuronal gene transfer with AAV8 leads to neurotoxic levels of tau or green fluorescent proteins. Mol Ther, 13, 517-27.

Lagier-Tourenne, C., M. Polymenidou, and D. W. Cleveland, TDP-43 and FUS/TLS: emerging roles in RNA processing and neurodegeneration. Hum Mol Genet, 2010. 19: R46-64.

Lambrechts, D., E. Storkebaum, and P. Carmeliet, VEGF: necessary to prevent motoneuron degeneration, sufficient to treat ALS? Trends Mol Med, 2004. 10: 275-82

Lawlor, P. A., R. J. Bland, P. Das, R. W. Price, V. Holloway, L. Smithson, B. L. Dicker, M. J. During, D. Young, and T. E. Golde. (2007). Novel rat Alzheimer's disease models based on AAV-mediated gene transfer to selectively increase hippocampal Abeta levels. Mol Neurodegener, 2, 11.

Li, Y., P. Ray, E. J. Rao, C. Shi, W. Guo, X. Chen, E. A. Woodruff, 3rd, K. Fushimi, and J. Y. Wu. (2010). A Drosophila model for TDP-43 proteinopathy. Proc Natl Acad Sci USA. 107(7), 3169-74

Liachko, N. F., C. R. Guthrie, and B. C. Kraemer, Phosphorylation promotes neurotoxicity in a Caenorhabditis elegans model of TDP-43 proteinopathy. J Neurosci, 2010. 30: 16208-19.

Ling, S. C., C. P. Albuquerque, J. S. Han, C. Lagier-Tourenne, S. Tokunaga, H. Zhou, and D. W. Cleveland. (2010). ALS-associated mutations in TDP-43 increase its stability and promote TDP-43 complexes with FUS/TLS. Proc Natl Acad Sci USA, 107, 13318-23.

Liu-Yesucevitz, L., et al., Tar DNA Binding Protein-43 (TDP-43) Associates with Stress Granules: Analysis of Cultured Cells and Pathological Brain Tissue. PLoS ONE, October 2010 5(10), e13250.

Mishra, D. and S. J. Flora. (2008). Differential oxidative stress and DNA damage in rat brain regions and blood following chronic arsenic exposure. Toxicol Ind Health, 24, 247-56.

Mitchell, J. D. and G. D. Borasio, Amyotrophic lateral sclerosis. Lancet, 2007. 369: 2031-41.

Moisse, K., et al., Cytosolic TDP-43 expression following axotomy is associated with caspase 3 activation in NFL−/− mice: support for a role for TDP-43 in the physiological response to neuronal injury. Brain Res, 2009. 1296: 176-86.

Molina, A. J. and O. S. Shirihai. (2009). Monitoring mitochondrial dynamics with photoactivatable [corrected] green fluorescent protein. Methods Enzymol, 457, 289-304.

Nagai, M., et al., Astrocytes expressing ALS-linked mutated SOD1 release factors selectively toxic to motor neurons. Nat Neurosci, 2007. 10: 615-22.

Nakamoto, M., V. Nalavadi, M. P. Epstein, U. Narayanan, G. J. Bassell, and S. T. Warren. (2007). Fragile X mental retardation protein deficiency leads to excessive mGluR5-dependent internalization of AMPA receptors. Proc Natl Acad Sci USA, 104, 15537-42.

Neumann, M., et al., Ubiquitinated TDP-43 in frontotemporal lobar degeneration and amyotrophic lateral sclerosis. Science, 2006. 314: 130-3

Ostrerova, N., L. Petrucelli, M. Farrer, N. Mehta, P. Alexander, P. Choi, J. Palacino, J. Hardy, and B. Wolozin. (1999). -Synuclein shares physical and functional homology with 14-3-3 proteins. J. Neurosci., 19, 5782-91.

Ostrerova-Golts, N., et al., The A53T a-Synuclein Mutation Increases Iron-Dependent Aggregation and Toxicity. J. Neuroscience, 2000. 20: 6048-54.

Petrucelli, L., C. O'Farrell, P. J. Lockhart, M. Baptista, K. Kehoe, L. Vink, P. Choi, B. Wolozin, M. Farrer, J. Hardy, and M. R. Cookson. (2002). Parkin protects against the toxicity associated with mutant alpha-synuclein: proteasome dysfunction selectively affects catecholaminergic neurons. Neuron, 36, 1007-19

Pool, M., et al., NeuriteTracer: a novel ImageJ plugin for automated quantification of neurite outgrowth. J Neurosci Methods, 2008. 168: 134-9.

Raoul, C., et al., Motoneuron death triggered by a specific pathway downstream of Fas. potentiation by ALS-linked SOD1 mutations. Neuron, 2002. 35: 1067-83.

Rideout, H. J., et al., alpha-synuclein is required for the fibrillar nature of ubiquitinated inclusions induced by proteasomal inhibition in primary neurons. J Biol Chem, 2004. 279: 46915-20.

Saha, S., et al., LRRK2 modulates vulnerability to mitochondrial dysfunction in Caenorhabditis elegans. J Neurosci, 2009. 29: 9210-8.

Schnitzler, A. C., I. Lopez-Coviella, and J. K. Blusztajn, Purification and culture of nerve growth factor receptor (p75)-expressing basal forebrain cholinergic neurons. Nat Protoc, 2008. 3: 34-40.

Somers, A., J. C. Jean, C. A. Sommer, A. Omani, C. C. Ford, J. A. Mills, L. Ying, A. G. Sommer, J. M. Jean, B. W. Smith, R. A. Lafyatis, M. F. Demierre, D. J. Weiss, D. L. French, P. Gadue, G. J. Murphy, G. Mostoslaysky, and D. N. Kotton. (2010). Generation of Transgene-Free Lung Disease-Specific Human iPS Cells Using a Single Excisable Lentiviral Stem Cell Cassette. Stem Cells 28 (10), 1728-1740.

Sommer, C. A., M. Stadtfeld, G. J. Murphy, K. Hochedlinger, D. N. Kotton, and G. Mostoslaysky. (2009). Induced pluripotent stem cell generation using a single lentiviral stem cell cassette. Stem Cells, 27, 543-9.

Sreedharan, J., et al., TDP-43 mutations in familial and sporadic amyotrophic lateral sclerosis. Science, 2008. 319: 1668-72.

Stallings, N. R., et al., Progressive motor weakness in transgenic mice expressing human TDP-43. Neurobiol Dis, 2010, 40(2), 404-414.

Tsai, K. J., et al., Elevated expression of TDP-43 in the forebrain of mice is sufficient to cause neurological and pathological phenotypes mimicking FTLD-U. J Exp Med, 2010. 207: 1661-73.

Tsai, N. P., Y. C. Tsui, and L. N. Wei, Dynein motor contributes to stress granule dynamics in primary neurons. Neuroscience, 2009. 159: 647-56.

Tudor, E. L., et al., Amyotrophic lateral sclerosis mutant vesicle-associated membrane protein-associated protein-B transgenic mice develop TAR-DNA-binding protein-43 pathology. Neuroscience, 2010. 167: 774-85.

Ved, R., et al., Similar Patterns of Mitochondrial Vulnerability and Rescue Induced by Genetic Modification of -Synuclein, Parkin and DJ-1 in C. Elegans. J Biol Chem, 2005. 280: 42655-68.

Wang, I. F., N. M. Reddy, and C. K. Shen. (2002). Higher order arrangement of the eukaryotic nuclear bodies. Proc Natl Acad Sci USA, 99, 13583-8.

Winton, M. J., et al., Disturbance of nuclear and cytoplasmic TAR DNA-binding protein (TDP-43) induces disease-like redistribution, sequestration, and aggregate formation. J Biol Chem, 2008. 283: 13302-9.

Wegorzewska, I., et al., TDP-43 mutant transgenic mice develop features of ALS and frontotemporal lobar degeneration. Proc Natl Acad Sci USA, 2009. 106: 18809-14.

Wils, H., et al., TDP-43 transgenic mice develop spastic paralysis and neuronal inclusions characteristic of ALS and frontotemporal lobar degeneration. Proc Natl Acad Sci USA, 2010. 107: 3858-63.

Wolozin, B., K. Iwasaki, P. Vito, K. Ganjei, E. Lacana, T. Sunderland, B. Zhao, J. Kusiak, W. Wasco, and L. D'Adamio. (1996). Participation of presenilin-2 in apoptosis: Enhanced basal activity conferred by Alzheimer mutation. Science, 274, 1710-3.

Xu, Y. F., et al., Wild-type human TDP-43 expression causes TDP-43 phosphorylation, mitochondrial aggregation, motor deficits, and early mortality in transgenic mice. J Neurosci, 2010. 30: 10851-9.

Yadav, R. S., R. K. Shukla, M. L. Sankhwar, D. K. Patel, R. W. Ansari, A. B. Pant, F. Islam, and V. K. Khanna. (2010). Neuroprotective effect of curcumin in arsenic-induced neurotoxicity in rats. Neurotoxicology, 31, 533-9.

Yang, C., et al., The C-terminal TDP-43 fragments have a high aggregation propensity and harm neurons by a dominant-negative mechanism. PLoS One, 2010. 5: e15878.

Zhang, Y. J., Y. F. Xu, C. A. Dickey, E. Buratti, F. Baralle, R. Bailey, S. Pickering-Brown, D. Dickson, and L. Petrucelli. (2007). Progranulin mediates caspase-dependent cleavage of TAR DNA binding protein-43. J Neurosci, 27, 10530-4.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and/or rearranged in various ways within the scope and spirit of the invention to produce further embodiments that are also within the scope of the invention. Those skilled in the art will recognize, or be able to ascertain, using no more than routine experimentation, numerous equivalents to the specific embodiments described specifically in this disclosure. Such equivalents are intended to be encompassed in the scope of the following claims.

The invention claimed is:

1. A method of modulating stress granules comprising contacting a cell with a TDP-43 inclusion inhibiting compound, wherein the compound is selected from the group consisting of:

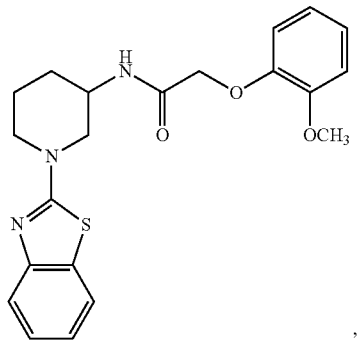

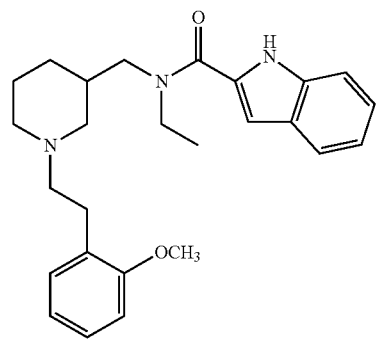

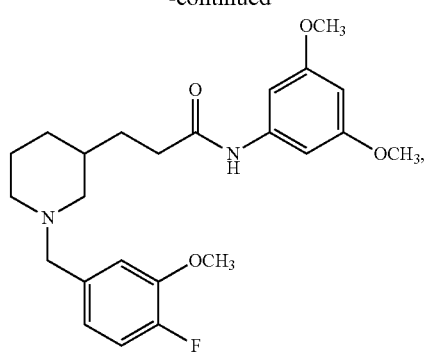
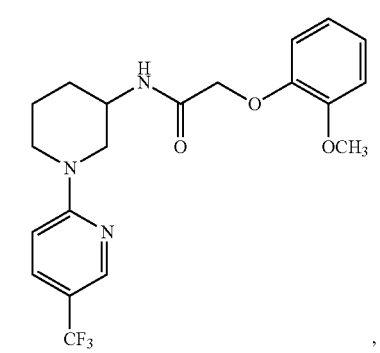
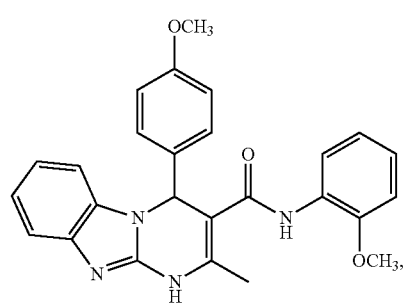
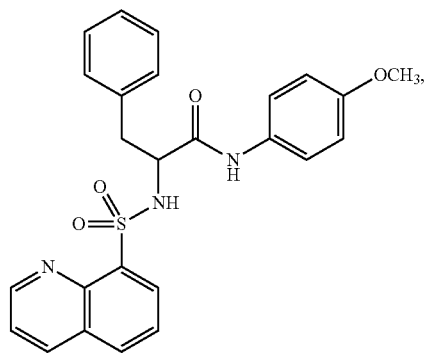
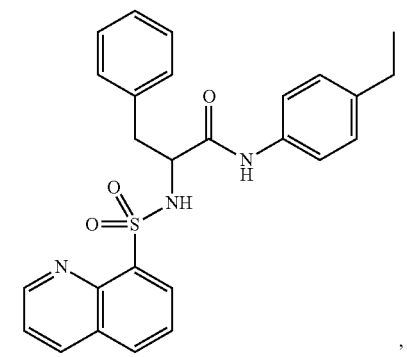
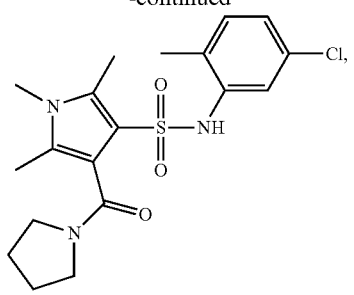
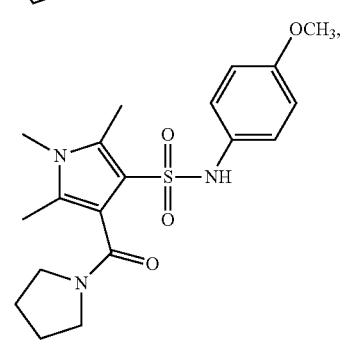
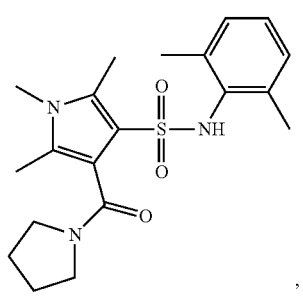
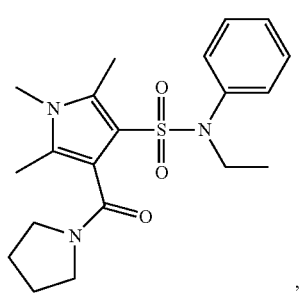
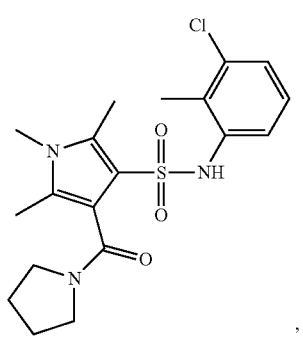

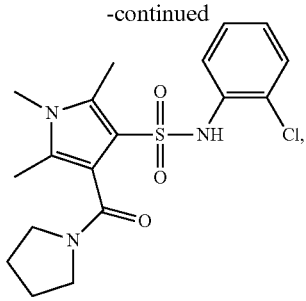
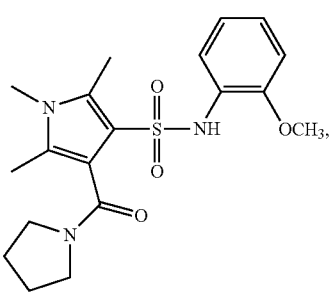
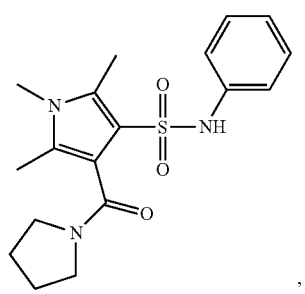
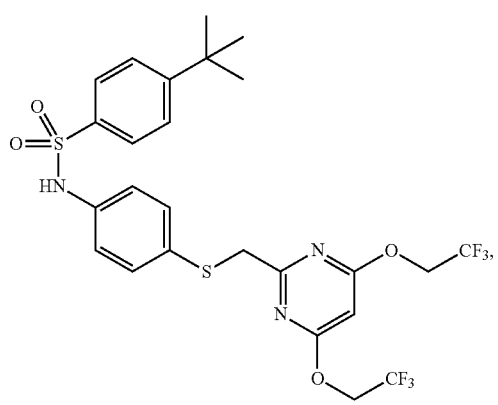
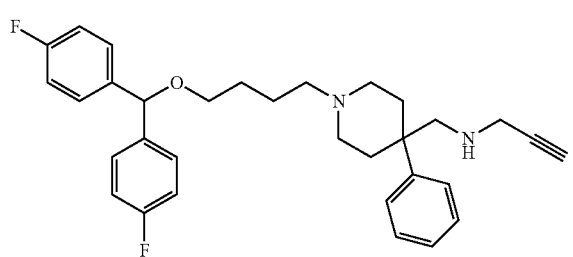
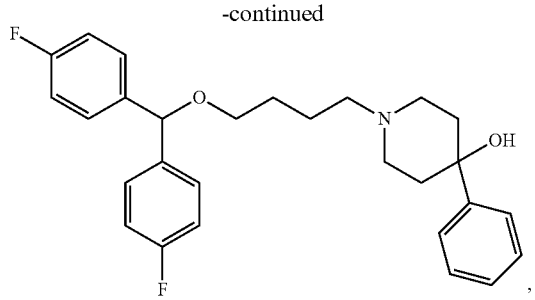
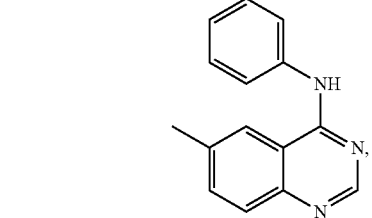
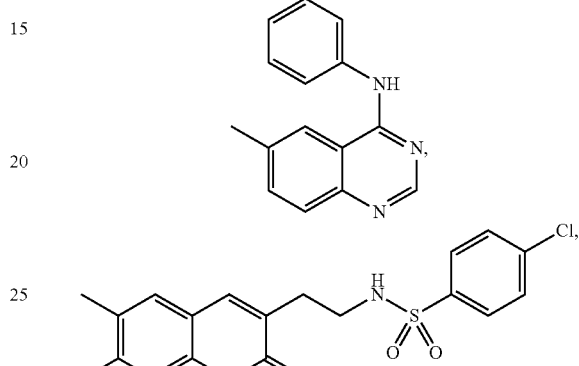
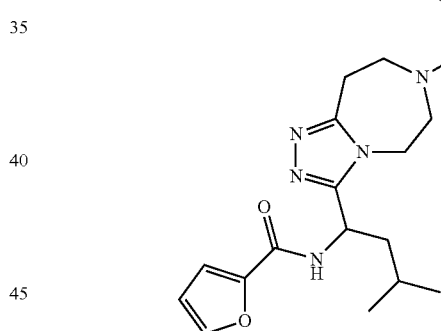
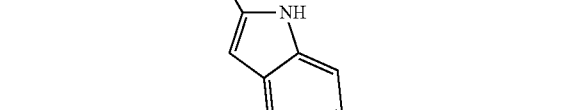
, and
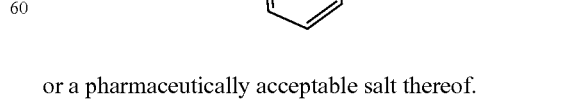
or a pharmaceutically acceptable salt thereof.
2. The method of claim 1, wherein stress granule formation is inhibited.
3. The method of claim 1, wherein stress granule formation is disaggregated.

4. The method of claim 1, wherein stress granule formation is stimulated.

5. The method of claim 1, wherein the stress granule comprises tar DNA binding protein-43 (TDP-43), T-cell intracellular antigen 1 (TIA-1), TIA1 cytotoxic granule-associated RNA binding protein-like 1 (TIAR), GTPase activating protein binding protein 1 (G3BP-1), GTPase activating protein binding protein 2 (G3BP-2), tristetraprolin (TTP), fused in sarcoma (FUS), or fragile X mental retardation protein (FMRP).

6. The method of claim 1, wherein the TDP-43 inclusion inhibiting compound is selected from the group consisting of:

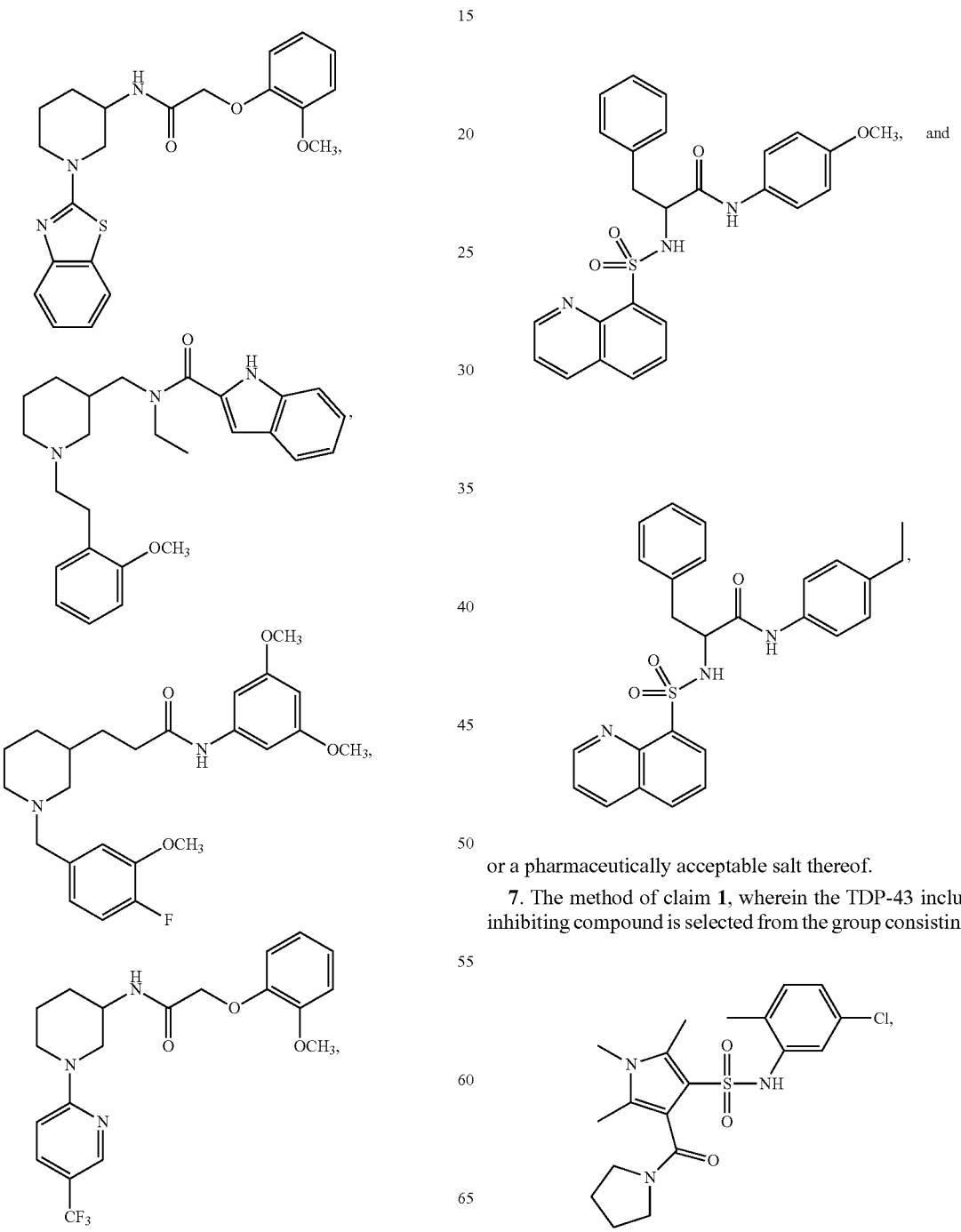

or a pharmaceutically acceptable salt thereof.

7. The method of claim 1, wherein the TDP-43 inclusion inhibiting compound is selected from the group consisting of:

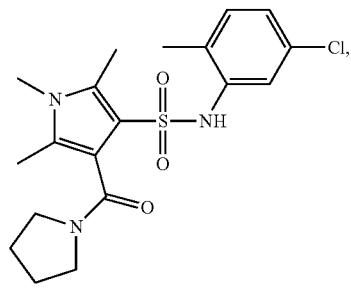

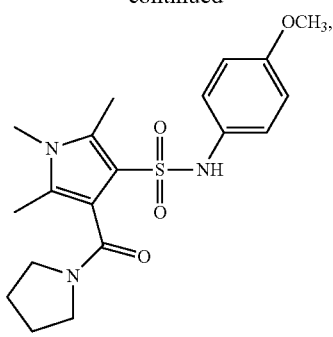
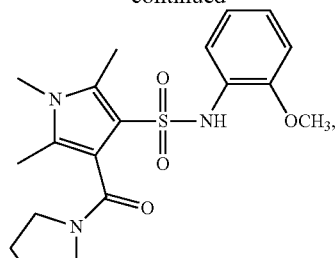
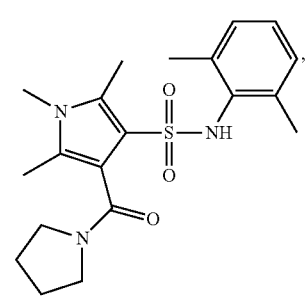
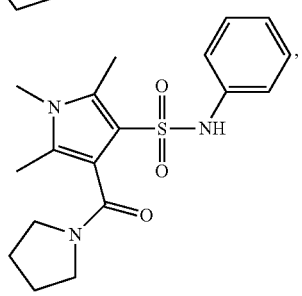
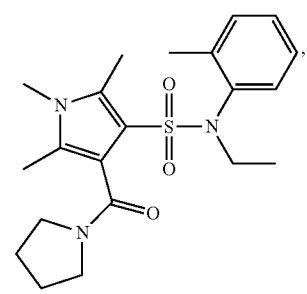
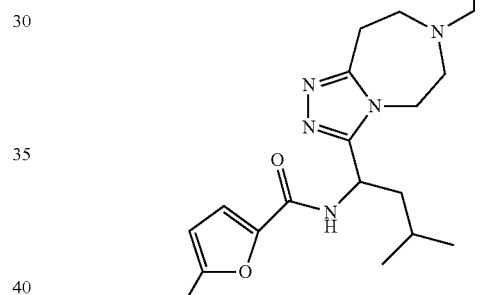
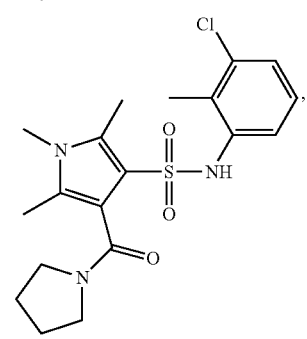
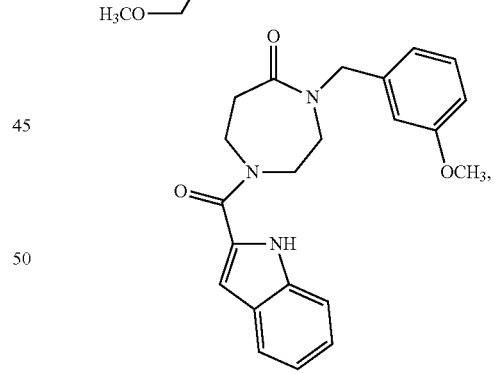
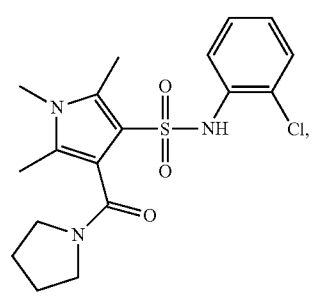

or a pharmaceutically acceptable salt thereof.

8. The method of claim 1, wherein the method is performed in a subject suffering from a neurodegenerative disease or disorder, the method comprising administering the TDP-43 inclusion inhibiting compound to the subject.

9. The method of claim 8, wherein the TDP-43 inclusion inhibiting compound inhibits stress granule formation or disaggregation.

10. The method of claim 8, wherein the TDP-43 inclusion inhibiting compound increases stress granule formation or disaggregation.

11. The method of claim 8, wherein the neurodegenerative disease is selected from the group consisting of Alzheimer's disease, frontotemporal dementia, FTLD-U (a frontotemporal dementia caused by mutations in progranulin protein), amyotrophic lateral sclerosis (ALS), Huntington's chorea, Creutzfeld-Jacob disease, trinucleotide repeat diseases, cerebral degenerative diseases presenile dementia, senile dementia, Parkinsonism linked to chromosome 17 (FTDP-17), progressive supranuclear palsy (PSP), Huntington's disease (HD), Pick's disease, primary progressive aphasia, corticobasal dementia, Parkinson's disease, Parkinson's disease with dementia, dementia with Lewy bodies, Down's syndrome, multiple system atrophy, spinal muscular atrophy (SMA), spinocerebellar ataxia, spinal degenerative disease/motor neuron degenerative diseases, Hallervorden-Spatz syndrome, cerebral infarct, cerebral trauma, chronic traumatic encephalopathy, and transient ischemic attack, or any combination thereof.

12. The method of claim 8, wherein the subject is a mammal.

13. The method of claim 12, wherein the subject is a human.

14. The method of claim 8, comprising further the step of diagnosing the subject for the neurodegenerative disease or disorder prior to the onset of said administration.

15. The method of claim 8, wherein the pathology of said neurodegenerative disease or disorder comprises stress granules.

\* \* \* \* \*